(12) United States Patent
Rothblum Watkins et al.

(10) Patent No.: US 8,598,133 B2
(45) Date of Patent: Dec. 3, 2013

(54) METHODS FOR TREATING PAIN

(75) Inventors: Linda May Rothblum Watkins, Boulder, CO (US); Erin Milligan, Boulder, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

(21) Appl. No.: 12/291,752

(22) Filed: Nov. 13, 2008

(65) Prior Publication Data
US 2009/0136453 A1 May 28, 2009

Related U.S. Application Data

(60) Continuation of application No. 11/215,721, filed on Aug. 29, 2005, now abandoned, which is a division of application No. 10/742,641, filed on Dec. 18, 2003, now Pat. No. 7,261,882.

(60) Provisional application No. 60/504,175, filed on Sep. 18, 2003, provisional application No. 60/480,886, filed on Jun. 23, 2003.

(51) Int. Cl.
*A61K 48/00* (2006.01)
*A01N 63/00* (2006.01)

(52) U.S. Cl.
USPC ........................................ 514/44 R; 424/93.2

(58) Field of Classification Search
USPC ........................................ 514/44 R; 424/93.2
See application file for complete search history.

(56) References Cited

U.S. PATENT DOCUMENTS

| | | | |
|---|---|---|---|
| 5,231,012 | A | 7/1993 | Mosmann et al. |
| 6,018,036 | A | 1/2000 | Mosmann et al. |
| 6,165,754 | A | 12/2000 | Crystal et al. |
| 6,217,857 | B1 | 4/2001 | Mosmann et al. |
| 6,413,942 | B1 | 7/2002 | Felgner et al. |
| 6,428,985 | B1 | 8/2002 | Bromberg et al. |
| 6,652,850 | B1 | 11/2003 | Philip et al. |
| 7,261,882 | B2 | 8/2007 | Watkins |
| 7,749,490 | B2 | 7/2010 | Sommer et al. |
| 2003/0044384 | A1 | 3/2003 | Roberts et al. |
| 2003/0049256 | A1 | 3/2003 | Tobinick |
| 2003/0130221 | A1 | 7/2003 | High et al. |
| 2003/0232781 | A1 | 12/2003 | Wolffe |
| 2004/0142893 | A1 | 7/2004 | Ikeda et al. |
| 2009/0208563 | A1 | 8/2009 | Watkins et al. |
| 2010/0028296 | A1 | 2/2010 | Chavez et al. |

FOREIGN PATENT DOCUMENTS

| | | |
|---|---|---|
| JP | 2003-146909 | 5/2003 |
| WO | WO 99/47157 | 9/1999 |
| WO | WO 99/56784 | 11/1999 |
| WO | WO 2005/000215 | 1/2005 |

OTHER PUBLICATIONS

Cavazzana-Calvo (The Journal of Clinical Investigation, 117(6): 1456-1465, 2007).*
Mata et al (Curr Gene Ther. 8(1): 42-48, 2008).*
Sterry et al (Pharmacological Reviews, 55(2):241-269, 2003).*
Storek et al, (Molecular Pain, 2(4): 1-11, 2006).*
Baron et al (Nature Clinical Practice, Neurology, 12(2): 95-106, 2006).*
Milligan, et al., "Controlling Pathological Pain by Adenovirally Driven Spinal Production of the Anti-Inflammatory Cytokine, Interleukin-10," *Eur J Neurosci* 21:2136-2148 (2005).
Milligan, et al., "Controlling Neuropathic Pain by Adenos-Associated Virus Driven Production of the Anti-Inflammatory Cytokine, Interleukin-10," *Mol Pain* 1:9, http://www.molecularpain.com/content/1/1/9, pp. 1-13 (2005).
Watkins & Maier, "Immune Regulation of Central Nervous System Functions: From Sickness Responses to Pathological Pain," *J Intern Med* 257:139-155 (2005).
Watkins & Maier, "Glia: A Novel Drug Discovery Target for Clinical Pain," *Nat Rev* 2:973-985 (2003).
Adachi, O. et al., "Gene transfer of Fc-fusion cytokine by in vivo electroporation: application to gene therapy for viral myocarditis," *Gene Therapy* 9:577-583 (2002).
Hao, S. et al., "Herpes simplex virus (HSV) vector expressing soluble TNF α—receptor and IL—4 produces persistent antinociception in neuropathic pain" *Washington D.C., Society for Neuroscience*, Program No. 131.8 (2003).
Laughlin et al., "Cytokine involvement in dynorphin-induced allodynia" *Pain* 84:159-167 (2000).
Meuli-Simmen et al., Gene expression along the cerebral-spinal axis after regional gene delivery *Human Gene Therapy* 10:2689-2700 (1999).
Okamoto et al., "Pro- and anti-inflammatory cytokine gene expression in rat sciatic nerve chronic constriction injury model of neuropathic pain" *Experimental Neurology* 169:386-391 (2001).
Plunkett et al., "Effects of interleukin-10 (IL-10) on pain behavior and gene expression following excitotoxic spinal cord injury in the rat" *Experimental Neurology* 168:144-154 (2001).
Yao et al., "Interleukin-2 gene has superior antinociceptive effects when delivered intrathecally" *Clinical Neuroscience and Neuropathology* 13(6):791-794 (2002).
Jiang et al., "Sustained Expression of Fc-Fusion Cytokine Following In Vivo Electroporation and Mouse Strain Differences in Expression Levels," *J. Biochem*, 133:423-427 (2003).
Cua et al., "Central Nervous System Expression of IL-10 Inhibits Autoimmune Encephalomyelitis," J. Immunology, Jan. 2001, vol. 166, pp. 603-608.
Andreansky et al., "Treatment of Intracranial Gliomas in Immunocompetent Mice using Herpes Simplex Viruses that Express Murine Interleukins," Gene Therapy, Jan. 1998, vol. 5, pp. 121-130.
Milligan, et al., (10$^{th}$ Congress on Pain: Abstract 392-P26, 135, Aug. 19, 2002.
Verma et al. (1997) Nature, vol. 389, p. 239.
Pfiefer and Verma (2001) Annu. Rev. Genomics. Hum. Genet. 2:177-211.

(Continued)

Primary Examiner — Marcia S Noble
Assistant Examiner — Magdalene Sgagias
(74) Attorney, Agent, or Firm — Roberta L. Robins; Robins Law Group

(57) ABSTRACT

Methods of treating pain by delivery of anti-inflammatory cytokines, proinflammatory cytokine antagonists, and agents that act to reduce or prevent proinflammatory cytokine actions, to the nervous system are described. These agents can be delivered using gene therapy techniques. Alternatively, the agents can be delivered in protein compositions.

5 Claims, 43 Drawing Sheets

(56) References Cited

OTHER PUBLICATIONS

Johnson-Saliba et al. (2001) Curr. Drug. Targets 2:371-99.
Shoji et al. (2004) Current Pharmaceutical Design 10:785-796.
Chan (2002) Ocular Immun. Inflam. 10:161-186.
Genbank Accession No. P22301 (Aug. 1, 1991).
Milligan, et al., Society for Neuroscience, 2002, Presentation No. 656.19, Neuroscience 2002 Abstract.
Yang et al., "Sustained Expression of Naked Plasmid DNA Encoding Hepatocyte Growth Factor in Mice Promotes Liver and Overall Body Growth," Hepatology, 2001, vol. 33, pp. 848-859.
Choate et al., "Direct Cutaneous Gene Delivery in a Human Genetic Skin Disease," Human Gene Therapy, 1997, vol. 8, pp. 1659-1665.
Zheng et al., "Administration of Noncytolytic IL-10/Fc in Murine Models of Lipopolysaccharide-Induced Septic Shock and Allogeneic Islet Transplantation," J. of Immunol., 1995, vol. 154, No. 10, pp. 5590-5600.
Wagner et al., "Anti-inflammatory interleukin-10 therapy in CCI neuropathy decreases thermal hyperalgesia, macrophage recruitment, and endoneurial TNF-$\alpha$ expression," Pain, 1998, vol. 74, pp. 35-42.
Raghavendra et al., "The Role of Spinal Neuroimmune Activation in Morphine Tolerance/Hyperalgesia in Neuropathic and Sham-Operated Rats," J. of Neuroscience, 2002, vol. 22, No. 22, pp. 9980-9989.
Japanese Office Action mailed Apr. 21, 2010, in Japanese application No. 2006-517161.
Mu et al., "IL-10 Suppresses Chemokines, Inflammation, and Fibrosis in a Model of Chronic Renal Disease," J. Am. Soc. Nephrol., 16:3651-3660 (2005).
Office Action dated Aug. 21, 2012 issued in U.S. Appl. No. 11/920,712.
Office Action dated Jul. 25, 2011 issued in U.S. Appl. No. 11/920,712.
Office Action dated Feb. 15, 2011 issued in U.S. Appl. No. 11/920,712.
Office Action dated Sep. 8, 2010 issued in U.S. Appl. No. 11/920,712.
Office Action dated Apr. 22, 2010 issued in U.S. Appl. No. 11/920,712.
Office Action dated Aug. 21, 2009 issued in U.S. Appl. No. 11/920,711.
Goodman, et al., "Synthesis and Characterization of Rat Interleukin-10 (IL-I0) CDNA Clones From the RNA of Cultured OX8-negative OX22-negative Thoracic Duct T Cells", Biochemical and Biophysical Research Communications, 189(1):1-7 (1992).
Vieira, et al. "Isolation and Expression of Human Cytokine Synthesis Inhibitory Factor CDNA Clones: Homology to Epstein-Barr Virus Open Reading Frame BCRF1", Proceedings of the National Academy of Sciences of USA, National Academy of Science, Washington, DC, US, 88:1172-1176 (1991).
Eck et al., Goodman & Gilman's The Pharmacological Basis of Therapeutics, McGraw-Hill, New York, p. 77-101 (1996).
Gorecki, D., Expert Opin. Emerging Drugs, 6(2):187-198 (2001).
Kodama et al., Current Medicinal Chemistry, 13:2155-2161 (2006).
Nishikawa et al., Human Gene Therapy, 12:861-870 (2001).
Skolnick et al., Trends in Biotech, 18:34-39 (2000).
Tomasinsig et al., Current Protein and Peptide Science, 6:23-34 (2005).
Smallwood et al., Virology, 304:135-145 (2002).
Chattopadhyay et al., Virus Research, 99:139-145 (2004).
Goudy et al., PNAS, 98(24):139-13918 (2001).
Milligan et al., "Repeated Intrathecal Injections of Plasmid DNA Encoding Interleukin-10 Produce Prolonged Reversal of Neuropathic Pain", Pain 126:294-308 (2006).

* cited by examiner

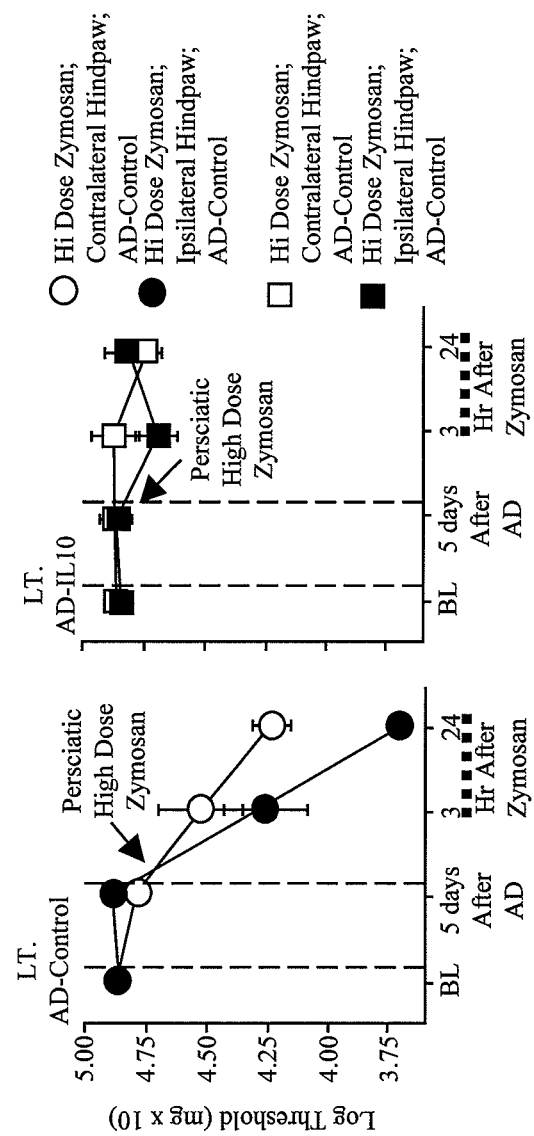

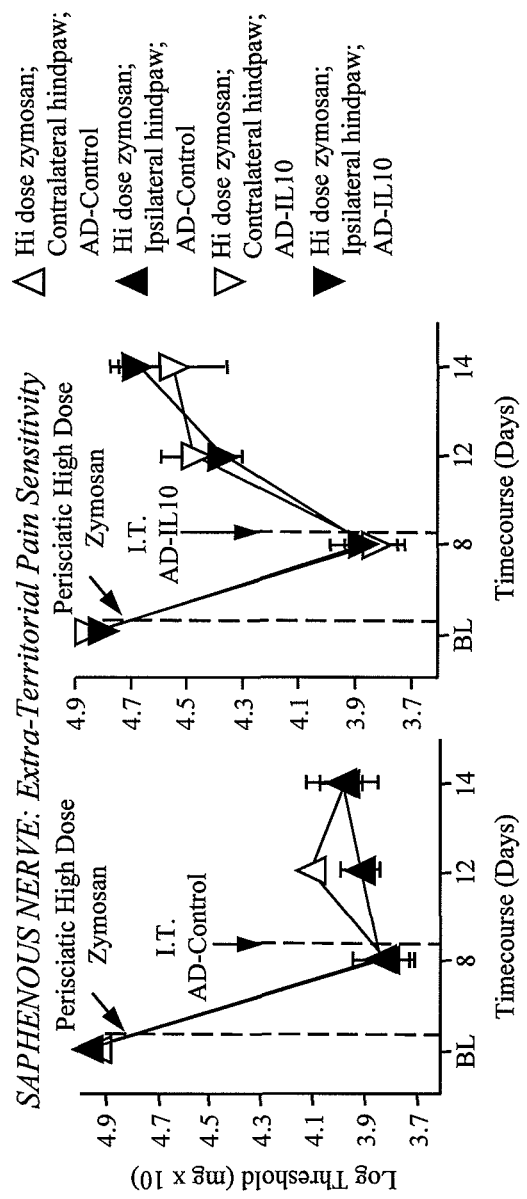

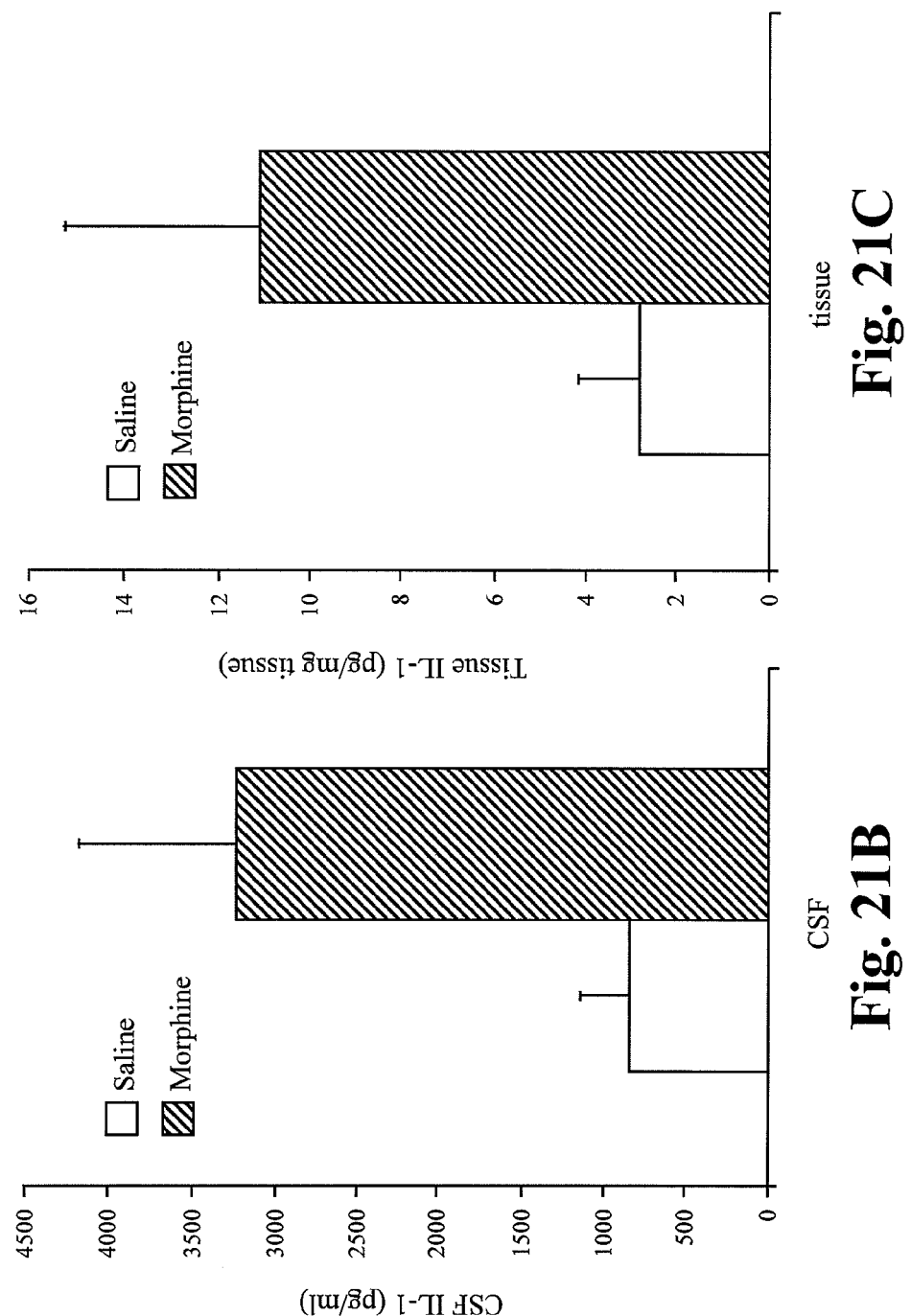

```
hIL-10  SPGQGTQSENSCTHFPGNLPNMLRDLRDAFSRVK
mIL-10  SRGQYSREDNNCTHFPVGQSHMLLELRDLRDAFSQVK
vIL-10  ---QCDNFP--QMLRDLRDAFSRVK
                  1        10        20        30 hIL-10  TFFQMKDQLDNLLLKESLLEDFKGYLGCQALSEMI
mIL-10  TFFQTKDQLDNILLTDSLMQDFKGYLGCQALSEMI
vIL-10  TFFQIKDEVDNLLLKESLLEDFKGYLGCQALSEMI
                 40        50        60 hIL-10  QFYLEEVMPQAENQDPDIKAHVNSLGENLKTLRLR
mIL-10  QFYLVEVMPQAEKHGPELKEHLNSLGEKLKTLRMR
vIL-10  QFYLEEVMPQAENQDPEAKDHVNSLGENLKTLRLR
                 70        80        90       100 hIL-10  LRRCHRFLPCENKSKAVEQVKNAFNKLQEKGIYKA
mIL-10  LRRCHRFLPCENKSKAVEQVKSDFNKLQEKGVYKA
vIL-10  LRRCHRFLPCENKSKAVEQIKNAFNKLQEKGIYKA
                110       120       130 hIL-10  MSEFDIFINYIEAYMTMKIRN
mIL-10  MNEFDIFINCIEAYMTMIKMKS
vIL-10  MSEFDIFINYIEAYMTIKAR
                140       150       160
```

Fig. 31

METHODS FOR TREATING PAIN

CROSS-REFERENCE TO RELATED APPLICATION

This application is a continuation of U.S. application Ser. No. 11/215,721, filed Aug. 29, 2005, which is a divisional of U.S. application Ser. No. 10/742,641, filed Dec. 18, 2003, now U.S. Pat. No. 7,261,882, from which applications priority is claimed under 35 U.S.C. §120. U.S. application Ser. No. 10/742,641 claims the benefit under 35 USC §119(e)(1) to U.S. Provisional Nos. 60/480,886, filed Jun. 23, 2003, and 60/504,175, filed Sep. 18, 2003. All of the foregoing applications are incorporated herein by reference in their entireties.

STATEMENT REGARDING FEDERALLY SPONSORED RESEARCH OR DEVELOPMENT

This invention was made with support under NIH Grants NS38020 and NS40696, from the National Institute of Neurological Diseases and Stroke, and DA15642 DA15656, from the National Institute of Drug Abuse. Accordingly, the United States Government may have certain rights in this invention.

TECHNICAL FIELD

The present invention relates generally to gene delivery methods. In particular, the present invention pertains to methods of treating or preventing pain by delivery of anti-inflammatory molecules that act on proinflammatory cytokines, or nucleic acid encoding the same, to neural tissue.

BACKGROUND

Gene therapy using genetically engineered cells and viruses has undergone impressive development over the past 40 years. Gene therapy techniques have been applied to diverse medical problems and have been used in over 350 clinical trials (Wu et al., *Meth. Strat. Anesthes.* (2001) 94:1119-1132). However, gene therapy has only recently been used in attempts to control pathological pain. Several approaches have been explored. For example, spinal implantation of genetically engineered cells has been used to increase inhibitory transmitters, including GABA (Eaton, M., *J. Peripheral Nerv. Sys.* (2000) 5:59-74), galanin (Eaton et al., *J. Peripheral Nerv. Sys.* (1999) 4:245-257), and beta-endorphin (Ishii et al., *Exp. Neurol.* (2000) 166:90-98). Herpes viruses have been utilized for their ability to be retrogradely transported from peripheral nerve terminals to dorsal root ganglion somas. In this way, elevations in preproenkephalin (Antunes Bras et al., *J. Neurochem.* (1998) 70:1299-1303; Wilson et al., *Proc. Natl. Acad. Sci. USA* (1999) 96:3211-3216) and decreases in CGRP via induced production of CGRP antisense (Lu et al., *Soc. Neurosci. Abs.* (1998) 24:1625) have been produced in sensory neurons. Lastly, adenoviruses have been injected into CSF to achieve virally driven beta-endorphin release from meningeal cells (Finegold et al., *Hum. Gene Ther.* (1999) 10:1251-1257. These gene therapy approaches focus on decreasing the excitability of spinal cord pain transmission neurons to incoming pain signals.

Activated spinal cord microglia and astrocytes appear to contribute to the creation and maintenance of pathological pain. In particular, activated glia appear to do so, at least in part, via their release of the proinflammatory cytokines interleukin-1 (IL1), tumor necrosis factor (TNF), and IL6 (for review, see Watkins et al., *Trends in Neurosci.* (2001) 24:450-455). These proinflammatory cytokines amplify pain by enhancing the release of "pain" neurotransmitters from incoming sensory nerve terminals and by enhancing the excitability of spinal cord dorsal horn pain transmission neurons (Reeve et al., *Eur. J. Pain* (2000) 4:247-257; Watkins et al., *Trends in Neurosci.* (2001) 24:450-455).

Astrocytes and micro glia express receptors for IL-10 (Mizuno et al., *Biochem. Biophys. Res. Commun.* (1994) 205-1907-1915) while spinal cord neurons do not (Ledeboer et al., *J. Neuroimmunol.* (2003) 136:94-103). In vitro studies have shown that IL-10 can selectively suppress proinflammatory cytokine production and signaling in these glial cells (Moore et al., *Ann. Rev. Immunol.* (2001) 19:683-765). In fact, IL-10 is an especially powerful member of the anti-inflammatory cytokine family in that it can suppress all proinflammatory cytokines implicated in pathological pain (IL1, TNF and IL6). IL-10 exerts this effect by inhibiting p38 MAP kinase activation (Strie et al., *Crit. Rev. Immunol.* (2001) 21:427-449); inhibiting NFkappaB activation, translocation and DNA binding (Strie et al., *Crit. Rev. Immunol.* (2001) 21:427-449); inhibiting proinflammatory cytokine transcription (Donnelly et al., *J. Interferon Cytokine Res.* (1999) 19:563-573; inhibiting proinflammatory cytokine mRNA stability and translation (Hamilton et al., *Pathobiology* (1999) 67:241-244; Kontoyiannis et al., *EMBO J.* (2001) 20:3760-3770); and inhibiting proinflammatory cytokine release (Moore et al., *Ann. Rev. Immunol.* (2001) 19:683-765). In addition, IL-10 stabilizes mRNAs of Suppressors of Cytokine Signaling, thereby increasing the production of a family of proteins that further inhibit proinflammatory cytokine production (Strie et al., *Crit. Rev. Immunol.* (2001) 21:427-449). IL-10 also interrupts proinflammatory cytokine signaling by downregulating proinflammatory cytokine receptor expression (Sawada et al., *J. Neurochem.* (1999) 72:1466-1471. Lastly, it upregulates endogenous antagonists of proinflammatory cytokines, including IL1 receptor antagonist and TNF decoy receptors (Foey et al., *J. Immunol.* (1998) 160:920-928; Huber et al., *Shock* (2000) 13:425-434).

The known effects of IL-10 are restricted to suppression of proinflammatory functions of activated immune and glial cells, leaving non-inflammatory aspects of cellular functions unaffected (Moore et al., *Ann. Rev. Immunol.* (2001) 19:683-765). White some neurons express IL-10 receptors, the only known action of IL-10 on neurons is inhibition of cell death (apoptosis) (Bachis et al., *J. Neurosci.* (2001) 21:3104-3112). Laughlin et al. (Laughlin et al., *Pain* (2000) 84:159-167) reported that intrathecal IL-10 blocks the onset of intrathecal dynorphin-induced, IL1-mediated mechanical allodynia. These investigators then tested the effect of IL-10 on pathological pain induced by excitotoxic spinal cord injury, a manipulation that activates astrocytes and microglia at the site of injury (Brewer et al., *Exp. Neurol.* (1999) 159:484-493). IL-10 decreased pathological pain behaviors when given 30 minutes following injury (Plunkett et al., *Exper. Neurol.* (2001) 168:144-154; Yu et al., *J. Pain* (2003) 4:129-140). This is in keeping with the fact that systemic IL-10 can reduce spinal cord proinflammatory cytokine production in response to excitotoxic injury, a manipulation that allows systemic IL-10 to reach the injured spinal cord due to disruption of the blood-brain barrier (Crisi et al., *Eur. J. Immunol.* (1995) 2:3033-3040; Bethea et al., *Neurotrauma* (1999) 16:851-863).

However, delivery of IL-10 systemically to treat CNS disorders is problematic. IL-10 does not cross the intact blood brain barrier in appreciable amounts (Banks, W. A., *J. Neurovirol.* (1999) 5:538-555), has a short half life such that sustainable delivery for prolonged periods would be difficult (Radwanski et al., *Pharm. Res.* (1998) 15:1895-1901), has not been successfully delivered orally, so presents problems for systemic administration, and would disrupt the normal functions of the body's immune system and would be expected to be detrimental to the health of the patient (Xing et al., *Gene Ther.* (1997) 4:140-149; Fedorak et al., *Gastroenterol.* (2000) 119:1473-1482; Tilg et al., *J. Immunol.* (2002) 169:2204-2209). Moreover, previous experimenters found that delivery of IL-10 24 hours after dynorphin-induced allodynia did not reduce the allodynia (Laughlin et al., *Pain* (2000) 84:159-167).

Previous reports have documented that IL-10 gene therapy reduced pneumonia-induced lung injury (Morrison et al., *Infect. Immun.* (2000) 68:4752-4758), decreased the severity of rheumatoid arthritis (Ghivizzani et al., *Clin. Orthop.* (2000) 379 Suppl.: S288-299), decreased inflammatory lung fibrosis (Boehler et al., *Hum. Gene Ther.* (1998) 9:541-551), inhibited cardiac allograft rejection (Brauner et al., *J. Thoracic Cardiovasc. Surg.* (1997) 114:923-933), suppressed endotoxemia (Xing et al., *Gene Ther.* (1997) 4:140-149), prevented and treated colitis (Lindsay et al., *J. Immunol.* (2001) 166:7625-7633), and reduced contact hypersensitivity (Meng et al., *J. Clin. Invest.* (1998) 101:1462-1467).

However, the ability of IL-10 gene therapy to reverse ongoing pain has not been documented prior to the present invention.

SUMMARY OF THE INVENTION

The present invention is based on the surprising discovery that pain can be successfully treated by delivering anti-inflammatory cytokines, such as IL-10 and IL-1ra, using gene therapy techniques, such as by targeting cells and tissues of the nervous system, including the spinal cord glia. In particular, the inventors herein have shown in acceptable pain models that gene delivery of anti-inflammatory cytokines and proinflammatory cytokine antagonists, such as IL-10 and IL-1ra, prevents and reverses pain, such as pathological and neuropathic pain, including thermal hyperalgesia and mechanical allodynia, without affecting basal pain responsivity to thermal or mechanical stimuli. Because these agents appear to selectively inhibit products of glial activation that lead to pathology while leaving basal glial and neuronal functions unaltered, this novel gene therapy approach for the control of pain provides a highly desirable alternative to neuronally focused gene therapies. Moreover, IL-10 and other agents that act on proinflammatory cytokines can be delivered either alone or in conjunction with gene therapy in order to treat existing pain.

Accordingly, in one embodiment, the invention is directed to a method of treating pain, such as neuropathic pain, in a vertebrate subject comprising administering to the nervous system of the subject a recombinant vector comprising a polynucleotide encoding an agent selected from the group consisting of an anti-inflammatory cytokine, a proinflammatory cytokine antagonist, and an agent that acts to reduce or prevent proinflammatory cytokine actions, operably linked to expression control elements, under conditions that result in expression of the polynucleotide in vivo to reduce pain.

In certain embodiments, the agent is one or more agents selected from the group consisting of interleukin-10 (IL-10), interleukin-1 receptor antagonist (IL-1ra), interleukin-4 (IL-4), interleukin-13 (IL-13), tumor necrosis factor soluble receptor (TNFsr), alpha-MSH, and transforming growth factor-beta 1 (TGF-β1).

In yet further embodiments, the vertebrate subject is a human and the anti-inflammatory cytokine is human IL-10.

In any of the above embodiments, the recombinant vector can be a recombinant virus, such as a recombinant adenovirus or a recombinant adeno-associated virion, or plasmid DNA. Moreover, if IL-10 is used, the IL-10 can be stabilized by providing the molecule as a fusion with the Fc portion of an IgG, as described more fully below.

In additional embodiments, the administering is by intraparenchymal, intrathecal or epidural delivery.

In further embodiments, the method further comprises subsequently administering at five days or less, such as three days or less, after the first administration, a recombinant vector comprising a polynucleotide encoding an agent selected from the group consisting of an anti-inflammatory cytokine, a proinflammatory cytokine antagonist, and an agent that acts to reduce or prevent inflammatory cytokine actions, operably linked to expression control elements, under conditions that result in expression of the polynucleotide in vivo to maintain reduced pain.

In additional embodiments, the method further comprises subsequently administering at five days or less, such as at three days or less, after the first administration, a therapeutically effective amount of a composition comprising an agent selected from the group consisting of an anti-inflammatory cytokine, a proinflammatory cytokine antagonist, and an agent that acts to reduce or prevent inflammatory cytokine actions to maintain reduced pain.

In yet another embodiment, the invention is directed to a method of treating pain in a mammalian subject comprising intrathecally administering to the central nervous system of the subject a recombinant virus or plasmid comprising a polynucleotide encoding IL-10, operably linked to expression control elements, under conditions that result in expression of the polynucleotide in vivo to reduce pain.

In certain embodiments, the vertebrate subject is a human and the IL-10 is human IL-10. The IL-10 can be stabilized by providing the molecule as a fusion with the Fc portion of an IgG, as described more fully below.

In additional embodiments, the subject is administered a recombinant virus, such as a recombinant adenovirus or a recombinant adeno-associated virion. In other embodiments, the subject is administered plasmid DNA.

In still further embodiments, the method further comprises subsequently administering at five days or less, such as at three days or less after the first administration, a recombinant vector comprising a polynucleotide encoding IL-10, operably linked to expression control elements, under conditions that result in expression of said polynucleotide in vivo to maintain reduced pain.

In additional embodiments, a therapeutically effective amount of a composition comprising IL-10 is subsequently administered at five days or less, such as three days or less after the first administration, to maintain reduced pain.

In still further embodiments, the invention is directed to a method of treating existing pain in a vertebrate subject comprising intrathecally administering to the subject a therapeutically effective amount of an agent selected from the group consisting of an anti-inflammatory cytokine, a proinflammatory cytokine antagonist, and an agent that acts to reduce or prevent cytokine actions.

In certain embodiments, the agent is one or more agents selected from the group consisting of interleukin-10 (IL-10), interleukin-1 receptor antagonist (IL-1ra), interleukin-4 (IL-4), interleukin-13 (IL-13), tumor necrosis factor soluble receptor (TNFsr), alpha-MSH, and transforming growth factor-beta 1 (TGF-β1).

In additional embodiments, the vertebrate subject is a human and the anti-inflammatory cytokine is human IL-10.

The IL-10 can be stabilized by providing the molecule as a fusion with the Fc portion of an IgG, as described more fully below.

In yet additional embodiments, the method further comprises subsequently administering at five days or less after the first administration, such as at three days or less, a recombinant vector comprising a polynucleotide encoding an agent selected from the group consisting of an anti-inflammatory cytokine, a proinflammatory cytokine antagonist, and an agent that acts to reduce or prevent inflammatory cytokine actions, operably linked to expression control elements, under conditions that result in expression of said polynucleotide in vivo to maintain reduced pain.

In additional embodiments, the method further comprises subsequently administering at five days or less, such as at three days or less after the first administration, a therapeutically effective amount of a composition comprising an agent selected from the group consisting of an anti-inflammatory cytokine, a proinflammatory cytokine antagonist, and an agent that acts to reduce or prevent inflammatory cytokine actions to maintain reduced pain.

In further embodiments, the invention is directed to a method of treating existing pain in a vertebrate subject comprising:

(a) administering to the nervous system of the subject a first composition comprising a therapeutically effective amount of interleukin-10 (IL-10); and (b) administering to the nervous system of the subject a second composition comprising a therapeutically effective amount of IL-10 at five days or less, such as at three days or less, after the first administration.

In certain embodiments, the first composition and the second composition are the same. In other embodiments, the first composition and the second composition are different. The IL-10 in the first composition and/or in the second composition can be fused to the Fc portion of an IgG. Additionally, in certain embodiments, the vertebrate subject is a human and the IL-10 in the first composition and/or the second composition is human IL-10.

In yet further embodiments, the invention is directed to a method of treating existing pain in a vertebrate subject comprising:

(a) administering to the nervous system of the subject a first composition comprising a therapeutically effective amount of interleukin-10 (IL-10); and (b) administering to the nervous system of the subject a second composition comprising a recombinant vector comprising a polynucleotide encoding IL-10, operably linked to expression control elements, under conditions that result in expression of said polynucleotide in vivo, wherein the second composition is administered at five days or less, such as at three days or less, after the first composition is administered.

In certain embodiments of the invention, the IL-10 in the first composition and/or in the second composition is fused to the Fc portion of an IgG. In additional embodiments, the vertebrate subject is a human and the IL-10 in the first compositions and/or the second composition is human IL-10.

In additional embodiments, the invention is directed to a method of treating existing pain in a vertebrate subject, such as neuropathic pain, comprising administering to the subject a therapeutically effective amount of a composition comprising an IL-10 polypeptide. In certain embodiments, the IL-10 polypeptide is fused to the Fc portion of an IgG. In additional embodiments, the vertebrate subject is a human and the anti-inflammatory cytokine is human IL-10.

In yet further embodiments, administering is by intraparenchymal, intrathecal or epidural delivery.

In additional embodiments, the method further comprises subsequently administering at five days or less, such as at three days or less, after the first administration, a recombinant vector comprising a polynucleotide encoding an agent selected from the group consisting of an anti-inflammatory cytokine, a proinflammatory cytokine antagonist, and an agent that acts to reduce or prevent inflammatory cytokine actions, operably linked to expression control elements, under conditions that result in expression of the polynucleotide in vivo to maintain reduced pain.

In further embodiments, the method further comprises subsequently administering at five days or less, such as at three days or less, after the first administration, a therapeutically effective amount of a composition comprising an agent selected from the group consisting of an anti-inflammatory cytokine, a proinflammatory cytokine antagonist, and an agent that acts to reduce or prevent inflammatory cytokine actions to maintain reduced pain.

These and other embodiments of the subject invention will readily occur to those of skill in the art in view of the disclosure herein.

BRIEF DESCRIPTION OF THE FIGURES

FIGS. 4A-4D show that adenoviral-delivered IL-I0 prevents sciatic inflammatory neuropathy (SIN)-induced mechanical allodynias. After predrug (baseline; BL) assessment on the von Frey test, animals were injected intrathecally with either adenovirus encoding for IL-10 (AD-IL10) (FIGS. 4B and 4D) or a control adenovirus that encoded for beta-galactosidase (AD-Control) (FIGS. 4A and 4C). Response thresholds were reassessed 4 days later to test whether either the presence of virus and/or the presence of virally generated human IL-10 affected basal response thresholds. As seen, Day 5 thresholds were not affected, compared to predrug BL. At this time, animals were unilaterally injected peri-sciatically with either 4 (FIGS. 4A and 4B) or 160 (FIGS. 4C and 4D) µg zymosan (yeast cell walls). These doses have previously been shown to produce unilateral (ipsilateral to zymosan injection) and bilateral mechanical allodynia, respectively (Milligan et al., *J. Neurosci*. (2003) 23:1026-1040). Animals receiving intrathecal AD-Control followed by peris-ciatic zymosan developed unilateral (FIG. 4A) and bilateral (FIG. 4C) mechanical allodynia as in previous studies. In contrast, both unilateral and bilateral mechanical allodynias were prevented in animals receiving intrathecal AD-IL10 (FIGS. 4B and 4D).

FIGS. 21A-21C show the effect of morphine administration of pain and IL-1 production. FIG. 21A shows that after repeated injections of morphine, exaggerated pain occurs upon discontinuation of the opiate. Animals given repeated morphine showed exaggerated response sensitivity to touch/pressure stimuli 24 hr after their last of 5 daily doses of intrathecal morphine (black bar, left) compared to rats receiving intrathecal saline instead of morphine (white bar, left). In contrast, when rats received daily IL-1ra, this increase in pain sensitivity was alleviated (black bar, right). FIGS. 21B and 21C show that chronic intrathecal morphine, but not equivolume chronic intrathecal vehicle, increases the production and release of the proinflammatory cytokine interleukin-1 in spinal cord. Rats were either given 5 days of once daily intrathecal injections of 10 µg morphine or equivolume vehicle. Two hours after the last injection, CSF and spinal cord were harvested and analyzed for IL-1 protein content by ELISA. As can be seen for both spinal cord CSF (FIG. 21B) and tissue (FIG. 21C), proinflammatory cytokine content was enhanced by chronic morphine.

FIG. 22A shows the hindpaw on the same side (left side) of the CCI and FIG. 22B shows the hindpaw of the healthy hindleg (right side). After baseline (BL) testing, rats received either CCI or sham surgery. They were retested 3 and 10 days later to verify that CCI (but not sham surgery) induced profound neuropathic pain as measured by mechanical allodynia. On Days 10, 11 and 12 (relative to CCI surgery), rats received an i.t. injection of either IL-10 protein or vehicle. The first injection (on Day 10) was 50 ng IL-10; the second (on Day 11) and third (on Day 12) injections were 500 ng IL-10. As seen in FIGS. 22A and 22B, 50 ng only partially reversed allodynia, a bit larger reversal was seen with 10 times that amount. Strikingly, the reversals were very short lived (less than 24 hr) and no increasing effectiveness was observed with repeated injections.

FIG. 23A shows the hindpaw on the same side (left side) of the CCI and FIG. 23B shows the hindpaw of the healthy hindleg (right side). It should be noted that CCI only produces pathological pain changes in the leg on the side of the nerve damage (that is, the left paw). The data from the right paw are included for completeness and to show that IL-10 and vehicle injections had no effect on the behaviors elicited from this control paw. After baseline (BL) testing, rats received either CCI or sham surgery. They were retested 3 and 10 days later to verify that CCI (but not sham surgery) induced profound neuropathic pain as measured by mechanical allodynia. On Days 10, 11 and 12 (relative to CCI surgery), rats received an i.t. injection of either IL-10 protein or vehicle. The first injection (on Day 10) was 50 ng IL-10; the second (on Day 11) and third (on Day 12) injections were 500 ng IL-10. As seen in FIG. 23A, 50 ng had no effect. A transient reversal was seen with 10 times that amount. The reversals were very short lived (less than 24 hr) and no increasing effectiveness was observed with repeated injections.

Figure 27:
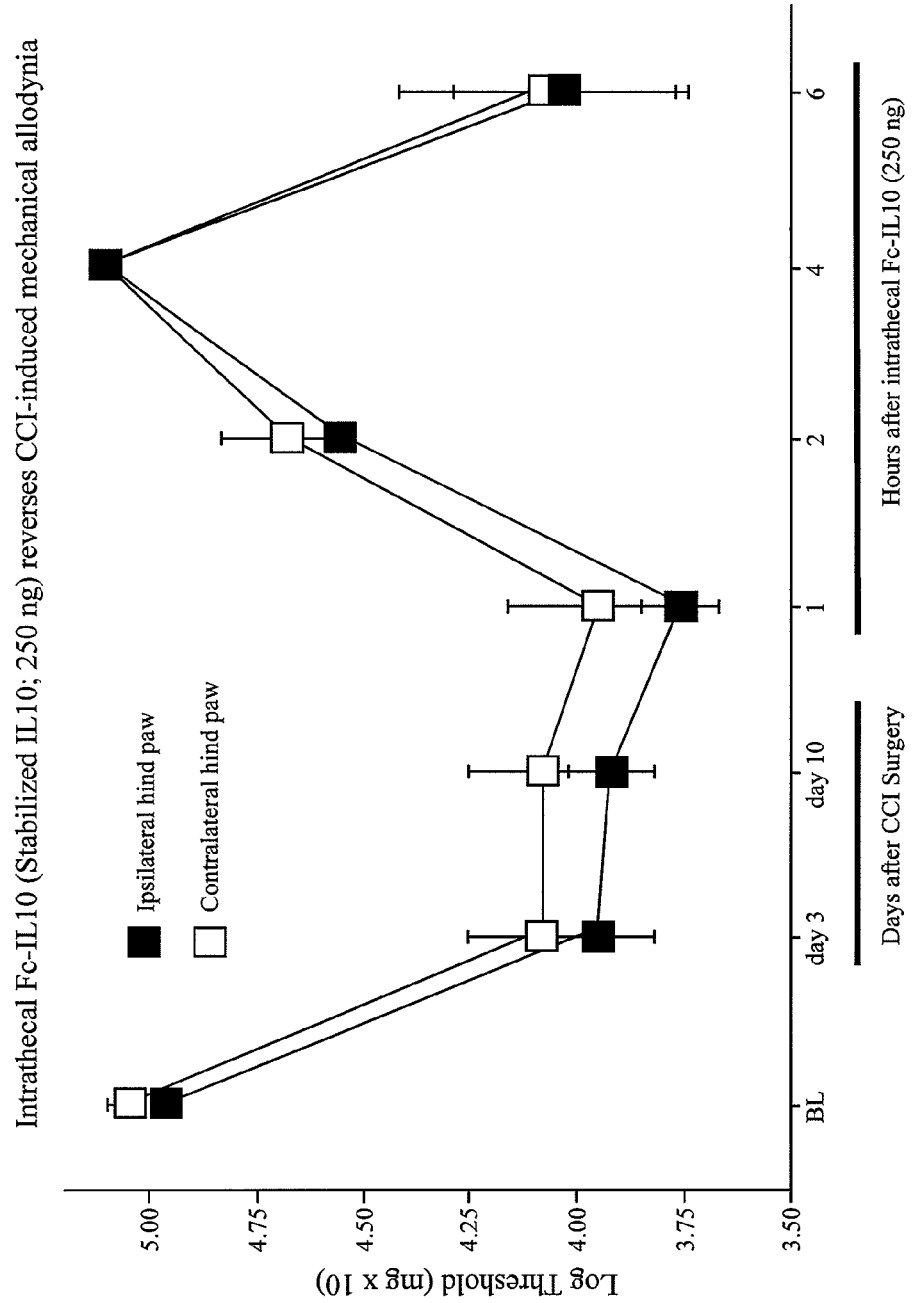

FIG. 27 shows that FcIL-10, delivered intrathecally, is effective in reversing mechanical allodynia induced by CCI. After baseline (BL) testing, rats received CCI surgery. They were re-tested 3 and 10 days later to verify that CCI induced profound neuropathic pain on both measures. After the Day 10 test, rats were injected i.t. with a stabilized variant of IL-10 (FcIL-10) plus a plasmid encoding for IL-10. Since plasmid has no effect on behavior until one day later, effects observed shortly after this injection procedure reflect actions by FcIL-10 itself. As can be seen in FIG. 27 mechanical allodynia was transiently reversed by FcIL-10 treatment.

Figure 28:
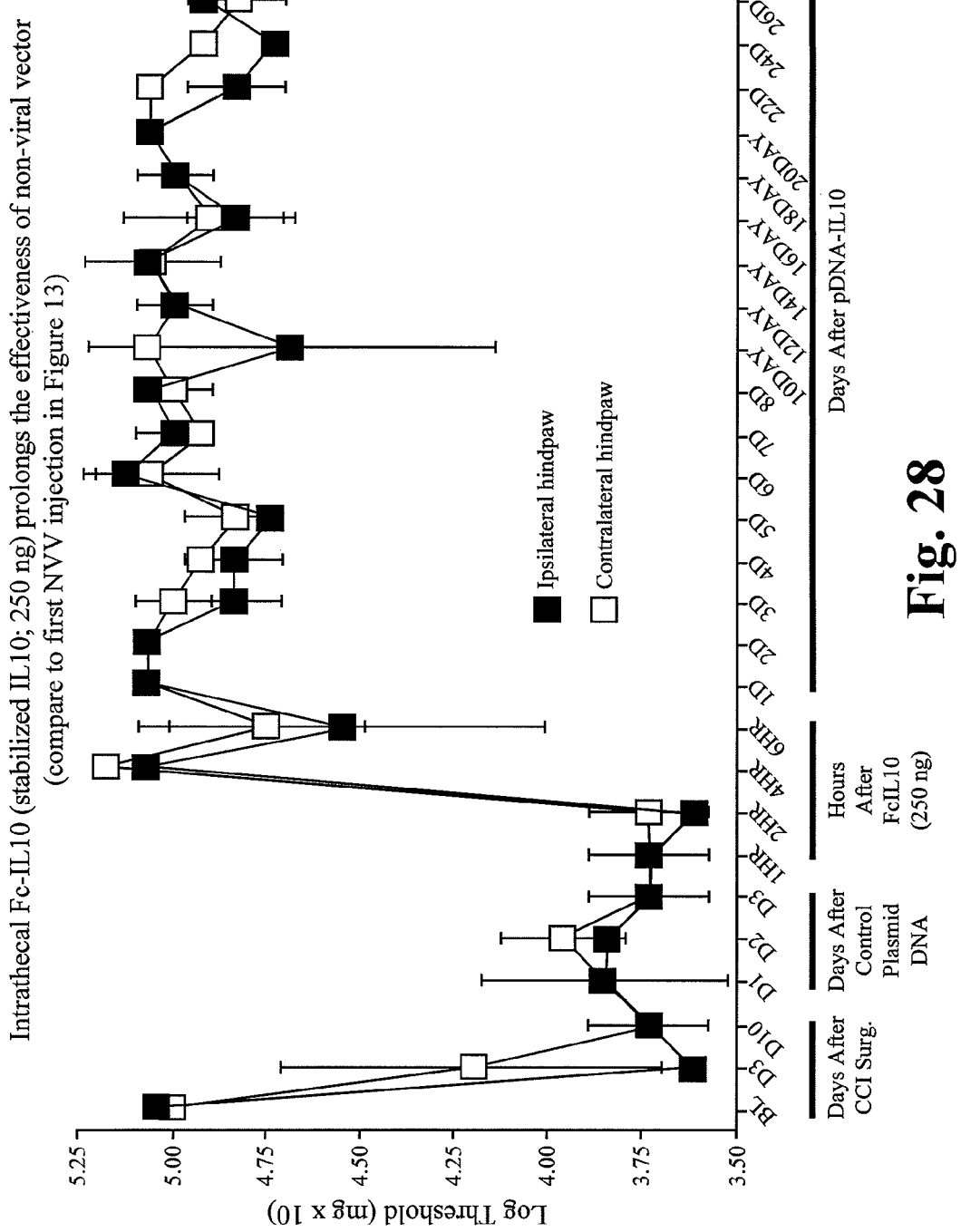

FIG. 28 shows that FcIL-10 is effective in enhancing reversal of mechanical allodynia when co-administered with a gene therapy vector, here shown with a plasmid encoding for IL-10. After baseline (BL) testing, rats received CCI surgery. They were re-tested 3 and 10 days later to verify that CCI induced profound neuropathic pain on both measures. After the Day 10 test, rats were injected i.t. with a control plasmid that did not encode IL-10; rather, it encoded for an inert intracellular protein (GFP). The presence of inert plasmid DNA did not affect behaviors tested the subsequent days. After the Day 13 test, rats were injected with either: (a) only plasmid encoding for IL-10 or (b) an equal amount of plasmid encoding for IL-10 plus a stabilized variant of IL-10 (FcIL-10) to test whether the presence of FcIL-10 would enhance vector efficacy. Indeed it does. Mechanical allodynia was reversed by plasmid-IL-10 alone for approximately 4 days. In contrast, the co-treatment with FcIL-10 remarkably enhanced both the onset and duration of plasmid-IL-10 efficacy on mechanical allodynia.

Figure 29A:
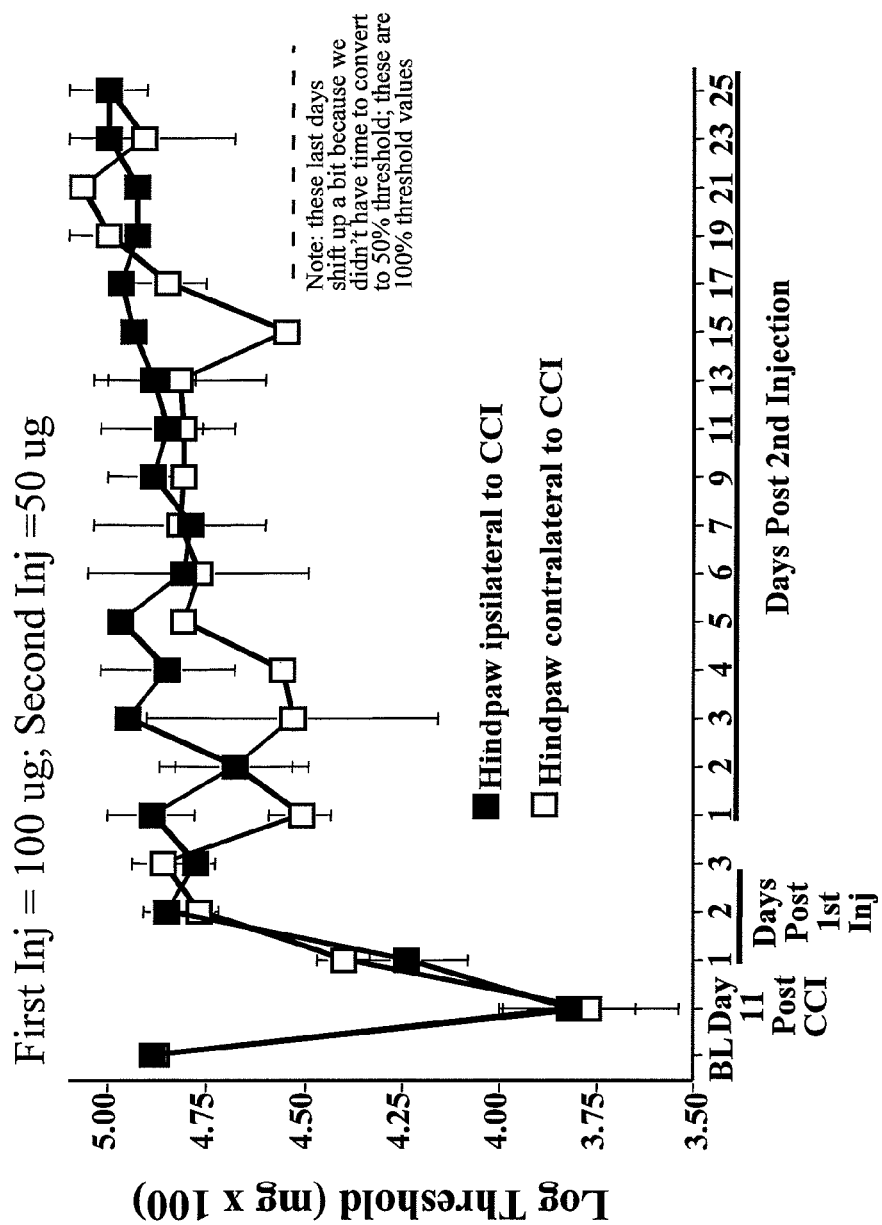
Figure 29B:
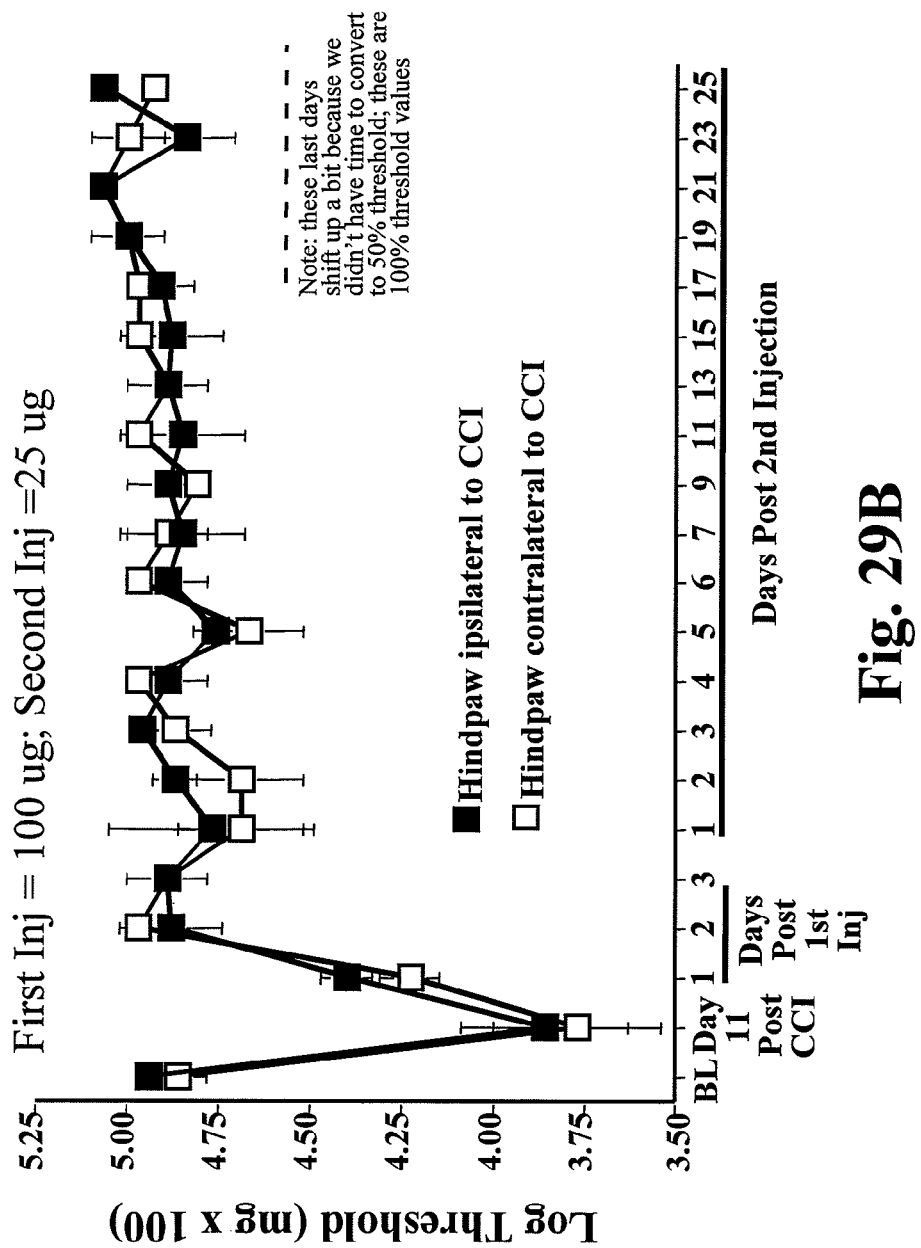
Figure 29C:
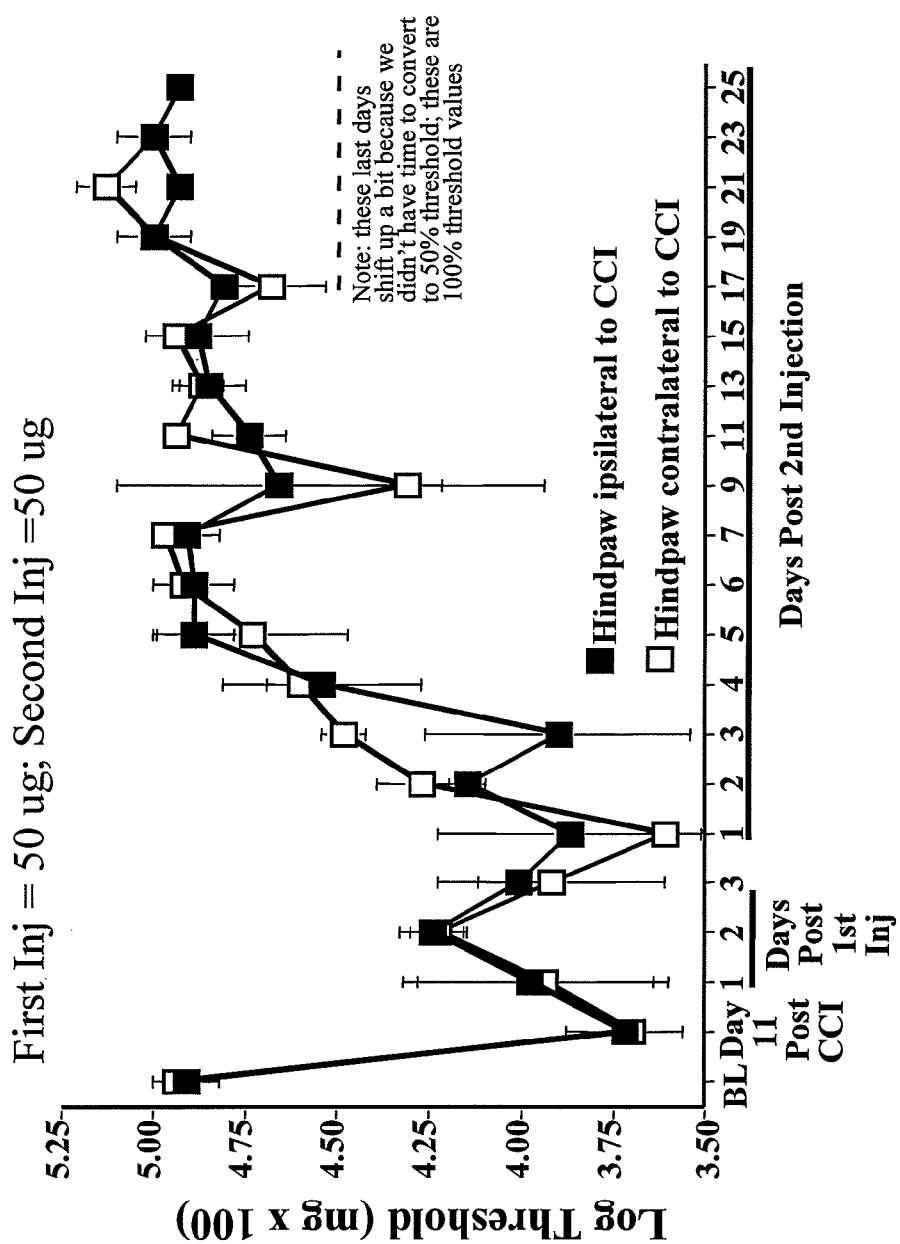

FIGS. 29A, 29B and 29C show that lower doses and dose combinations of plasmid IL-10 gene therapy effectively reverse CCI-induced mechanical allodynia. After baseline (BL) testing, rats received CCI surgery. They were re-tested 3 and 10 days later to verify that CCI induced profound neuropathic pain. Rats were then injected with either: (a) 100 μg plasmid encoding IL-10 (Day 10) followed by 50 μg plasmid encoding IL-10 (Day 13) (FIG. 29A); (b) 100 μg plasmid encoding IL-10 (Day 10) followed by 25 μg plasmid encoding IL-10 (Day 13) (FIG. 29B); or (c) 50 μg plasmid encoding IL-10 (Day 10) followed by 50 μg plasmid encoding IL-10 (Day 13) (FIG. 29C). Each led to reversal of mechanical allodynia over time.

Figure 30A:
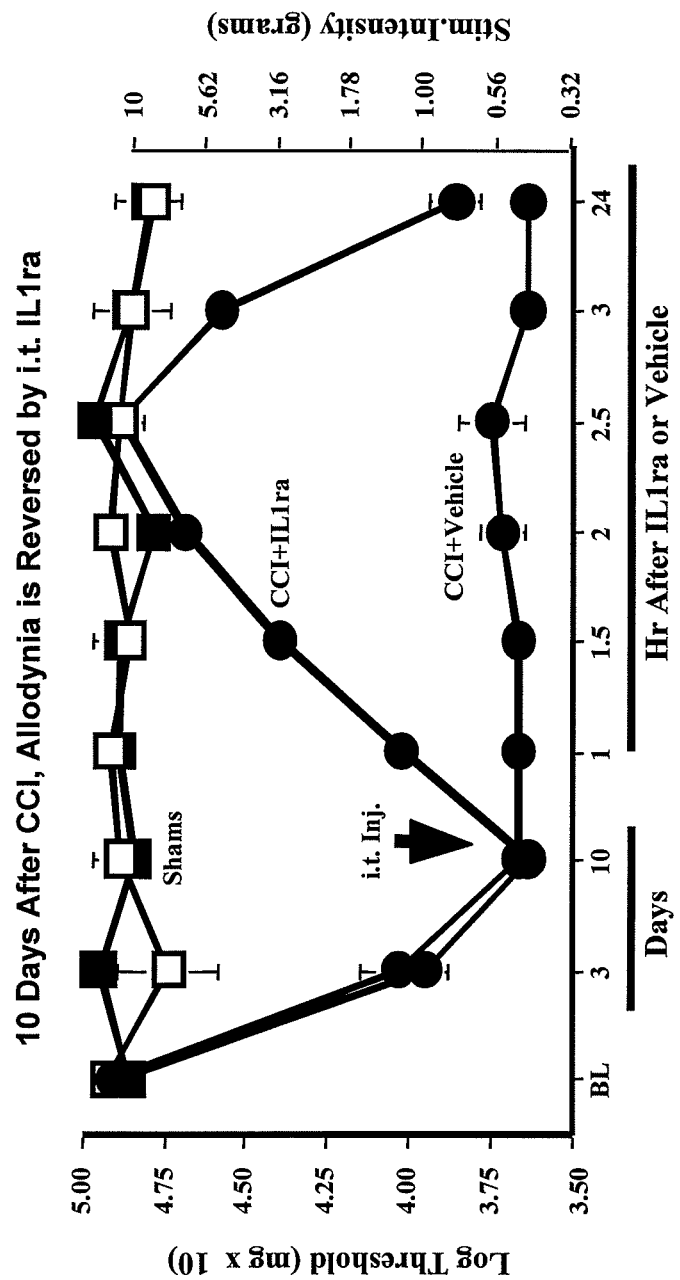
Figure 30B:
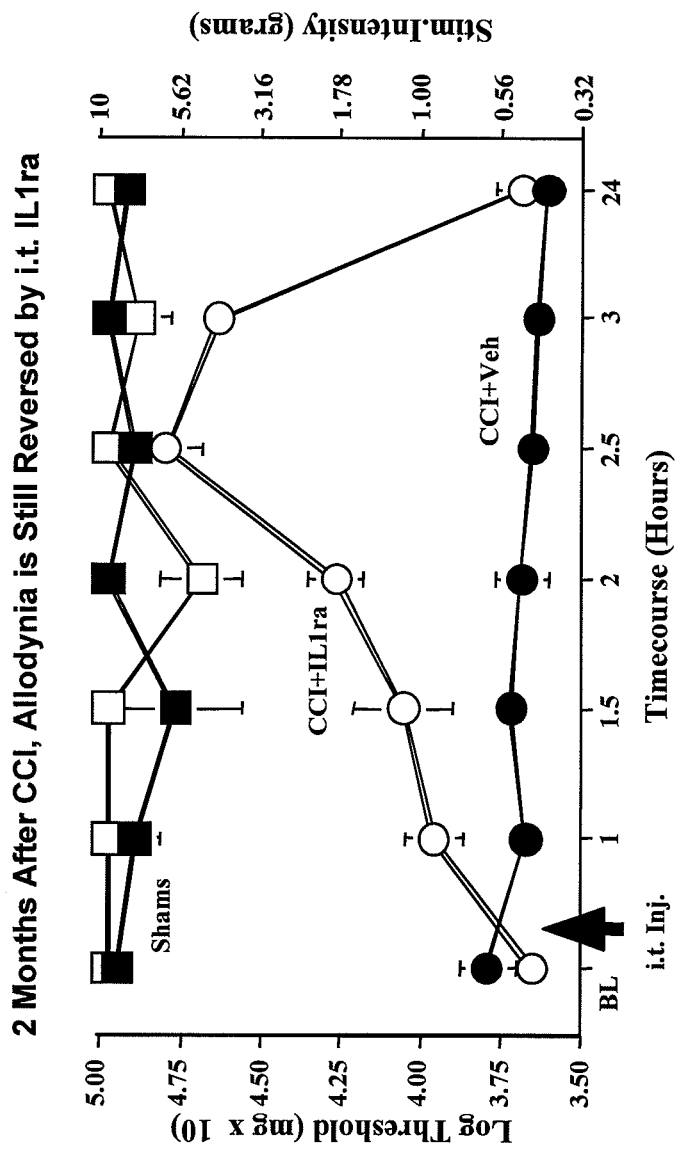

FIGS. 30A and 30B show that gene therapy with IL-10 is likely reversing CCI, because CCI is mediated by proinflammatory cytokines. After baseline assessment on the von Frey test (BL), CCI or sham surgery was performed, and behavior reassessed 3 and 10 days later to verify surgical efficacy. In FIG. 30A, rats then received either intrathecal interleukin-1 receptor antagonist or equivolume vehicle and were tested over time. In FIG. 30B, the identical procedure was carried out except that the drug injections were administered 2 months after surgery. As can be seen, IL-1ra transiently reversed CCI-induced enhanced pain at both times tested, supporting that proinflammatory cytokine are enduring mediators of neuropathic pain in particular, and pathological pain more generally enduring mediators of neuropathic pain in particular, and pathological pain more generally.

FIG. 31 shows a comparison of the amino acid sequences of mature secreted forms of human IL-10 (hIL-10) (SEQ ID NO:1), mouse IL-10 (mIL-10) (SEQ ID NO:2) and a viral form of IL-10 (vIL-10) (SEQ ID NO:3). Amino acid residues differing from the human sequence are boxed.

DETAILED DESCRIPTION OF THE INVENTION

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an anti-inflammatory cytokine" includes a mixture of two or more such cytokines, and the like.

By "pathological pain" is meant any pain resulting from a pathology, such as from functional disturbances and/or pathological changes, injuries, lesions, burns and the like. One form of pathological pain is "neuropathic pain." The term "neuropathic pain" as used herein refers to pain caused by, but not limited to, a neuropathy, an encephalopathy and/or a myelopathy (i.e., functional disturbances or pathological states of the peripheral nervous system, brain and spinal cord, respectively). Neuropathic pain can be caused by nerve damage, injury such as spinal cord injury, neuritis, inflammation, noninflammatory lesions, electrical injuries, headaches, and the like. Neuropathic pain can also be caused by complications of various diseases, including without limitation, demyelinating diseases, diabetes, amyloid diseases, porphyric diseases, Lyme disease, leprosy, acromegaly, rheumatoid arthritis, autoimmune diseases, metabolic diseases, cancer, and viral infection. Such pain can also be caused by toxic states, such as but not limited to, toxic states caused by arsenic, isoniazid, lead and nitrofurantoin. Examples of neuropathic pain include, but are not limited to, thermal or mechanical hyperalgesia, thermal or mechanical allodynia, diabetic pain, pain arising from irritable bowel or other internal organ disorders, endometriosis pain, phantom limb pain, complex regional pain syndromes, fibromyalgia, low back pain, cancer pain, pain arising from infection, inflammation or trauma to peripheral nerves or the central nervous system, multiple sclerosis pain, entrapment pain, pain from HIV infection, herpesvirus infection, and the like.

"Hyperalgesia" means an abnormally increased pain sense, such as pain that results from an excessive sensitiveness or sensitivity.

"Hypalgesia" (or "hypoalgesia") means the decreased pain sense.

"Allodynia" means pain that results from a non-noxious stimulus to the skin. Examples of allodynia include, but are not limited to, cold allodynia, tactile allodynia, and the like.

"Nociception" is defined herein as pain sense. "Nociceptor" herein refers to a structure that mediates nociception. The nociception may be the result of a physical stimulus, such as, mechanical, electrical, thermal, or a chemical stimulus. Nociceptors are present in virtually all tissues of the body.

"Analgesia" is defined herein as the relief of pain without the loss of consciousness. An "analgesic" is an agent or drug useful for relieving pain, again, without the loss of consciousness.

The term "nervous system" includes both the central nervous system and the peripheral nervous system." The term "central nervous system" or "CNS" includes all cells and tissue of the brain and spinal cord of a vertebrate. The term "peripheral nervous system" refers to all cells and tissue of the portion of the nervous system outside the brain and spinal cord. Thus, the term "nervous system" includes, but is not limited to, neuronal cells, glial cells, astrocytes, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue, cells in the epineurium, perineurium, endoneurium, funiculi, fasciculi, and the like.

The term "anti-inflammatory cytokine" as used herein refers to a protein that decreases the action or production of one or more proinflammatory cytokines or proteins produced by nerves, neurons, glial cells, endothelial cells, fibroblasts, muscle, immune cells or other cell types. Such inflammatory cytokines and proteins include, without limitation, interleukin-1 beta (IL-1β), tumor necrosis factor-alpha (TNF-α), interleukin-6 (IL6), inducible nitric oxide synthetase (iNOS) and the like. Non-limiting examples of anti-inflammatory cytokines include interleukin-10 (IL-10) including viral IL-10, interleukin-4 (IL-4), interleukin-13 (IL-13), alpha-MSH, transforming growth factor-beta 1 (TGF-β1), and the like. All of these anti-inflammatory cytokines, as well as active fragments, and active analogs thereof, which retain the ability to decrease pain as measured in any of the known pain models including those described further herein, are intended for use with the present invention.

Thus, the full-length proteins and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70...80...85...90...95...98...99% etc. identity that retain the ability to reduce pain, are contemplated for use herein.

By "proinflammatory cytokine antagonist" is meant any molecule that blocks or antagonizes the biologic action of a proinflammatory cytokine, such as by binding or interacting with a proinflammatory cytokine receptor thereby reducing or inhibiting the production of the proinflammatory cytokine. The terms "antagonist", "inhibitor", and "blocker" are used interchangeably herein. Non-limiting examples of such antagonists include interleukin-1 receptor antagonist (IL-1ra); KINERET (recombinant IL-1ra, Amgen); tumor necrosis factor soluble receptor (TNFsr); soluble TNF receptor Type I (Amgen); pegylated soluble TNF receptor Type I (PEGs TNF-R1) (Amgen); TNP decoy receptors; ETANERCEPT (ENBREL, Amgen); INFLIXIMAB (REMICADE, Johnson & Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; ONERCEPT, a recombinant TNF binding protein (r-TBP-1) (Serono); IL1-Receptor Type 2 (Amgen), AMG719 (Amgen) and IL-1 Trap (Regeneron).

All of these proinflammatory cytokine antagonists, as well as active fragments, and active analogs thereof, which retain the ability to decrease pain as measured in any of the known pain models including those described further herein, are intended for use with the present invention.

Thus, the full-length molecules and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70...80...85...90...95...98...99% etc. identity that retain the ability to reduce pain, are contemplated for use herein.

By "an agent that acts to reduce inflammatory cytokine actions" is meant an agent that induces anti-inflammatory cytokine production. Such agents include, without limitation, IL-9, Hsp27 (see, U.S. Patent Publication No. 2001/0049357).

All of these agents, as well as active fragments, and active analogs thereof, which retain the ability to decrease pain as measured in any of the known pain models including those described further herein, are intended for use with the present invention.

Thus, the full-length molecules and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70...80...85...90...95...98...99% etc. identity that retain the ability to reduce pain, are contemplated for use herein.

The term "analog" refers to biologically active derivatives of the reference molecule, or fragments of such derivatives, that retain the ability to reduce pain. In general, the term "analog" refers to compounds having a native polypeptide sequence and structure with one or more amino acid additions, substitutions and/or deletions, relative to the native molecule. Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, argime, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any number between 5-50, so long as the desired function of the molecule remains intact.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression in vivo.

By "recombinant virus" is meant a virus that has been genetically altered, e.g., by the addition or insertion of a heterologous nucleic acid construct into the particle.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methyl aminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3 prime (3')" or "5 prime (5')" relative to another sequence, it is to be understood that it is the position of the sequences in the "sense" or "coding" strand of a DNA molecule that is being referred to as is conventional in the art.

The terms "subject", "individual" or "patient" are used interchangeably herein and refer to a vertebrate, preferably a mammal. Mammals include, but are not limited to, murines, rodents, simians, humans, farm animals, sport animals and pets.

The terms "effective amount" or "therapeutically effective amount" of a composition or agent, as provided herein, refer to a nontoxic but sufficient amount of the composition or agent to provide the desired response, such as a reduction or reversal of pain. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

"Treatment" or "treating" pain includes: (1) preventing pain, i.e. causing pain not to develop or to occur with less intensity in a subject that may be exposed to or predisposed to pain but does not yet experience or display pain, (2) inhibiting pain, i.e., arresting the development or reversing pain, or (3) relieving pain, i.e., decreasing the amount of pain experienced by the subject.

By "treating existing pain" is meant relieving or reversing pain in a subject that has been experiencing pain for at least 24 hours, such as for 24-96 hours or more, such as 25 . . . 30 . . . 35 . . . 40 . . . 45 . . . 48 . . . 50 . . . 55 . . . 65 . . . 72 . . . 80 . . . 90 . . . 96 . . . 100, etc. hours. The term also intends treating pain that has been occurring long-term, such as for weeks, months or even years.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that gene therapy using genes encoding anti-inflammatory cytokines, proinflammatory cytokine antagonists, and other agents that act to reduce or prevent proinflammatory cytokine actions, serves to reduce pain in vertebrate subjects. Advantages to this approach to pain control are numerous. First, basal pain responsivity to at least heat and mechanical stimuli is not altered. Thus, normal pain processing does not appear to be noticeably influenced by the presence of the effective dose of the anti-inflammatory cytokine such as IL-10. Second, anti-inflammatory cytokines such as IL-10 appear to target a pathological aspect of glial activation, suppressing the pronociceptive influences that activated glia exert on pain modulatory systems. Third, the agents not only prevent pathological pain from developing, but can also decrease and/or reverse already established pathological pain states.

Gene therapy techniques can be used alone or in conjunction with traditional drug and protein delivery techniques. Alternatively, agents that act on proinflammatory cytokines, such as any of the anti-inflammatory cytokines and proinflammatory cytokine antagonists described herein, can be administered alone, without gene delivery, to treat subjects with existing pain.

In order to further an understanding of the invention, a more detailed discussion is provided below regarding anti-inflammatory cytokines, as well as various gene delivery methods for use with the present invention.

Anti-Inflammatory Cytokines, Proinflammatory Cytokine Antagonists and Agents that Act to Reduce or Prevent Inflammatory Cytokine Action As explained above, the present invention makes use of anti-inflammatory cytokines, proinflammatory cytokine antagonists and agents that act to reduce or prevent inflammatory cytokine action, to treat pain, such as pathological and neuropathic pain. Particularly preferred anti-inflammatory cytokines and antagonists for use with the present invention include, without limitation, interleukin-10 (IL-10), interleukin-1 receptor antagonist (IL-1ra), interleukin-4 (IL-4), interleukin-13 (IL-13), tumor necrosis factor soluble receptor (TNFsr), alpha-MSH and transforming growth factor-beta 1 (TGF-β1). The native molecules, as well as fragments and analogs thereof, which retain the ability to decrease pain as measured in any of the known pain models including those described further herein, are in tended for use with the present invention. One particularly preferred IL-10 molecule for use herein includes a fusion of IL-10 to the Fc portion of an IgG, described in more detail below. Moreover, sequences derived from any of numerous species can be used with the present invention, depending on the animal to be treated.

For example, a number of sequences related to IL-10, as well as IL-10 fragments, variants and agonists, which function to reduce pain will also find use herein. For example, sequences related to IL-10 are described in, e.g., International Publication Nos. WO 00/65027; WO 98/28425; WO 95/24425 (immunomodulator *Trichinella* substances). International Publication No. WO 95/03411 describes shortened IL-10 sequences, variants and agonists of IL-10 having amino acid substitutions or deletions at the carboxyl and/or amino terminus of mature human sequence; U.S. Pat. No. 6,428,985 describes IL-10 variants with a substitution of Ile at position 87 of the mature human IL-10 sequence with Ala or Gly; U.S. Pat. No. 6,159,937 describes an IL-10 fragment with the sequence Ala-Tyr-Met-Thr-Met-Lys-Ile-Arg-Asn) (SEQ ID NO:4); International Publication No. WO 97/26778 describes IL-10 variants with the sequence X1-X2-X3-Thr-X4-Lys-X5-Arg-X6 (SEQ ID NO:5) where X1=Ala or Gly; X2=Tyr or Phe; X3, X4 and X5 are independently selected from Met, Ile, Leu and Val; and X6=Asp, Gln or Gly.

Nucleotide and amino acid sequences of anti-inflammatory cytokines, proinflammatory cytokine antagonists and agents that act to reduce or prevent inflammatory cytokine action, and variants thereof, from several animal species are well known. For example, IL-10 has been isolated from a number of animal and viral species. IL-10 for use herein includes IL-10 from any of these various species. Non-limiting examples of viral IL-10 include the IL-10 homologues isolated from the herpesviruses such as from Epstein-Barr virus (see, e.g., Moore et al., *Science* (1990) 248:1230-1234; Hsu et al., *Science* (1990) 250:830-832; Suzuki et al., *J. Exp. Med.* (1995) 182:477-486), Cytomegalovirus (see, e.g., Lockridge et al., *Virol.* (2000) 268:272-280; Kotenko et al., *Proc. Natl. Acad. Sci. USA* (2000) 97:1695-1700; International Publication No. WO 01/16153), and equine herpesvirus (see, e.g., Rode et al., *Virus Genes* (1993) 7:111-116), as well as the IL-10 homologue from the OrF virus (see, e.g., Imlach et al., *J. Gen. Virol.* (2002) 83:1049-1058 and Fleming et al., *Virus Genes* (2000) 21:85-95). See, also, FIG. 31 herein depicting the amino acid sequence of a mature, secreted form of viral IL-10. Representative, non-limiting examples of other IL-10 sequences for use with the present invention include the sequences described in NCBI accession numbers NM000572, U63015, AF418271, AF247603, AF247604, AF247606, AF247605, AY029171, UL16720 (all human sequences), and FIG. 31 herein depicting the amino acid sequence of a mature secreted form of human IL-10; NM012854, L02926, X60675 (rat); NM010548, AF307012, M37897, M84340 (all mouse sequences), and FIG. 31 herein depicting the amino acid sequence of a mature secreted form of mouse IL-10; U38200 (equine); U39569, AF060520 (feline sequences); U00799 (bovine); U11421, Z29362 (ovine sequences); L26031, L26029 (macaque sequences); AF294758 (monkey); U33843 (canine); AF088887, AF068058 (rabbit sequences); AF012909, AF120030 (woodchuck sequences); AF026277 (possum); AF097510 (guinea pig); U11767 (deer); L37781 (gerbil); AB107649 (llama and camel).

Non-limiting examples of IL-1ra sequences for use with the present invention include the sequences described in NCBI accession numbers NM173843, NM173842, NM173841, NM000577, AY196903, BC009745, AJ005835, X64532, M63099, X77090, X52015, M55646 (all human sequences); NM174357, AB005148 (bovine sequences); NM031167, S64082, M57525, M644044 (mouse sequences); D21832, 568977, M57526 (rabbit sequences); SEG AB045625S, M63101 (rat sequences); AF216526, AY026462 (canine sequences); U92482, D83714 (equine sequences); AB038268 (dolphin).

Non-limiting examples of IL-4 sequences for use with the present invention include the sequences described in NCBI accession numbers NM172348, AF395008, AB015021, X16710, A00076, M13982, NM000589 (all human sequences); BC027514, NM021283, AF352783, M25892 (mouse sequences); NM173921, AH003241, M84745, M77120 (bovine sequences); AY130260 (chimp); AF097321, L26027 (monkey); AY096800, AF172168, Z11897, M96845 (ovine sequences); AF035404, AF305617 (equine sequences); AF239917, AF187322, AF054833, AF104245 (canine sequences); X16058 (rat); AF046213 (hamster); L07081 (cervine); U39634, X87408 (feline); X68330, L12991 (porcine sequences); U34273 (goat); AB020732 (dolphin); L37779 (gerbil); AF068058, AF169169 (rabbit sequences); AB107648 (llama and camel).

Non-limiting examples of IL-13 sequences for use with the present invention include the sequences described in NCBI accession numbers NM002188, U10307, AF377331, X69079 (all human sequences); NM053828, L26913 (rat sequences); AF385626, AF385625 (porcine sequences); AF244915 (canine); NM174089 (bovine); AY244790 (monkey); NM008355 (mouse); AB107658 (camel); AB107650 (llama).

Non-limiting examples of TGF-β1 sequences for use with the present invention include the sequences described in NCBI accession numbers NM000660, BD0097505, BD0097504, BD0097503, BD0097502 (all human sequences); NM021578, X52498 (rat sequences); AJ009862, NM011577, BC013738, M57902 (mouse sequences); AF461808, X12373, M23703 (porcine sequences);

AF175709, X99438 (equine sequences); X76916 (ovine); X60296 (hamster); L34956 (canine).

Non-limiting examples of alpha-MSH sequences for use with the present invention include the sequences described in NCBI accession number NM 000939 (human); NM17451 (bovine); NM 008895 (mouse); and M 11346 (xenopus).

Non-limiting examples of TNF receptor sequences for use with the present invention include the sequences described in NCBI accession numbers X55313, M60275, M63121, NM152942, NM001242, NM152877, NM152876, NM152875, NM152874, NM152873, NM152872, NM152871, NM000043, NM 001065, NM001066, NM148974, NM148973, NM148972, NM148971, NM148970, NM148969, NM148968, NM148967, NM148966, NM148965, NM003790, NM032945, NM003823, NM001243, NM152854, NM001250 (all human sequences); NM013091, M651122 (rat sequences).

Non-limiting examples of IL-9 sequences for use with the present invention include the sequences described in NCBI accession numbers NM000590 (human) and NM008373 (mouse).

Polynucleotides encoding the desired anti-inflammatory cytokine, proinflammatory cytokine antagonist and agents that act to reduce or prevent inflammatory cytokine for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. The gene of interest can also be produced synthetically, rather than cloned, based on the known sequences. The molecules can be designed with appropriate codons for the particular sequence. The complete sequence is then assembled from overlapping oligonucleotides prepared by standard methods and assembled into a complete coding sequence. See, e.g., Edge, *Nature* (1981) 292:756; Nambair et al., *Science* (1984) 223:1299; and Jay et al., *J. Biol. Chem.* (1984) 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., *Proc. Natl. Acad. Sci. USA* (1991) 88:4084-4088. Additionally, oligonucleotide-directed synthesis (Jones et al., *Nature* (1986) 54:75-82), oligonucleotide directed mutagenesis of preexisting nucleotide regions (Riechmann et al., *Nature* (1988) 332:323-327 and Verhoeyen et al., *Science* (1988) 239:1534-1536), and enzymatic filling-in of gapped oligonucleotides using $T_4$ DNA polymerase (Queen et al., *Proc. Natl. Acad. Sci. USA* (1989) 86:10029-10033) can be used to provide molecules for use in the subject methods.

Gene Delivery Techniques

Anti-inflammatory genes as described above, are delivered to the subject in question using any of several gene-delivery techniques. Several methods for gene delivery are known in the art. As described further below, genes can be delivered either directly to the mammalian subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described. See, e.g., U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Replication-defective murine retroviral vectors are widely utilized gene transfer vectors. Murine leukemia retroviruses include a single strand RNA complexed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells provided that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476). Adenovirus vectors for use in the subject methods are described in more detail below.

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875. AAV vector systems are also described in further detail below.

Additional viral vectors which will find use for delivering the nucleic acid molecules of interest include those derived from the pox family of viruses, including vaccinia virus and avian poxvirus. By way of example, vaccinia virus recombinants expressing the genes can be constructed as follows. The DNA encoding the particular polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the protein into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as but not limited to vectors derived from the Sindbis and Semliki Forest viruses, will also find use as viral vectors for delivering the anti-inflammatory cytokine gene. For a description of Sinbus-virus derived vectors useful for the practice of the instant methods, see, Dubensky et al., *J. Virol.* (1996) 70:508-519; and International Publication Nos. WO 95/07995 and WO 96/17072.

Alternatively, the anti-inflammatory cytokines can be delivered without the use of viral vectors, such as by using plasmid-based nucleic acid delivery systems as described in U.S. Pat. Nos. 6,413,942; 6,214,804; 5,580,859; 5,589,466; 5,763,270; and 5,693,622, all incorporated herein by reference in their entireties. Plasmids will include the gene of interest operably linked to control elements that direct the expression of the protein product in vivo. Such control elements are well known in the art.

Plasmid Gene Delivery Systems

As explained above, the gene of interest can be introduced into the subject or cells of the subject using non-viral vectors, such as plasmids, and any of the several plasmid delivery techniques well-known in the art. For example, vectors can be introduced without delivery agents, as described in, e.g., U.S. Pat. Nos. 6,413,942, 6,214,804 and 5,580,859, all incorporated by reference herein in their entireties.

Alternatively, the vectors encoding the gene of interest can be packaged in liposomes prior to delivery to the subject or to cells derived therefrom, such as described in U.S. Pat. Nos. 5,580,859; 5,549,127; 5,264,618; 5,703,055, all incorporated herein by reference in their entireties. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527. The DNA can also be delivered in cochleate lipid compositions similar to those described by Papahadjopoulos et al., *Biochem. Biophys. Acta.* (1975) 394:483-491. See, also, U.S. Pat. Nos. 4,663,161 and 4,871,488, incorporated herein by reference in their entireties.

The vectors may also be encapsulated, adsorbed to, or associated with, particulate carriers, well known in the art. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

Moreover, plasmid DNA can be guided by a nuclear localization signal or like modification.

Additionally, biolistic delivery systems employing particulate carriers such as gold and tungsten, are useful for delivering genes of interest. The particles are coated with the gene to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744, all incorporated herein by reference in their entireties.

A wide variety of other methods can be used to deliver the vectors. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, peptoid delivery, or microinjection. See, e.g., Sambrook et al., supra, for a discussion of techniques for transforming cells of interest; and Felgner, P. L., *Advanced Drug Delivery Reviews* (1990) 5:163-187, for a review of delivery systems useful for gene transfer. Methods of delivering DNA using electroporation are described in, e.g., U.S. Pat. Nos. 6,132,419; 6,451,002, 6,418,341, 6233, 483, U.S. Patent Publication No. 2002/0146831; and International Publication No. WO/0045823, all of which are incorporated herein by reference in their entireties.

It may also be desirable to fuse the plasmid encoding the gene of interest to immunoglobulin molecules in order to provide for sustained expression. One convenient technique is to fuse the plasmid encoding the agent of interest to the Fc portion of a mouse IgG2a with a noncytolytic mutation. Moreover, the IL-10 gene can be present in the form of a fusion protein, fused to the Fc portion of an IgG. Such a technique has been shown to provide for sustained expression of cytokines, such as IL-10, especially when combined with electroporation. See, e.g., Jiang et al., *J. Biochem.* (2003) 133:423-427; and Adachi et al., *Gene Ther.* (2002) 9:577-583.

Adenovirus Gene Delivery Systems

In a preferred embodiment of the subject invention, a nucleotide sequence encoding the anti-inflammatory cytokine is inserted into an adenovirus-based expression vector. The adenovirus genome is a linear double-stranded DNA molecule of approximately 36,000 base pairs with the 55-kDa terminal protein covalently bound to the 5' terminus of each strand. Adenoviral ("Ad") DNA contains identical Inverted Terminal Repeats ("ITRs") of about 100 base pairs with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single-stranded and can form a "panhandle" intermediate, which allows replication initiation and generation of a daughter duplex molecule. Alternatively, replication can proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins. During the late phase, late viral gene products are expressed in addition to the early gene products and host cell DNA and protein synthesis are shut off. Consequently, the cell becomes dedicated to the production of viral DNA and of viral structural proteins.

The E1 region of adenovirus is the first region expressed after infection of the target cell. This region consists of two transcriptional units, the E1A and E1B genes. The main functions of the E1A gene products are to induce quiescent cells to enter the cell cycle and resume cellular DNA synthesis, and to transcriptionally activate the E1B gene and the other early regions (E2, E3, E4). Transfection of primary cells with the E1A gene alone can induce unlimited proliferation (immortalization), but does not result in complete transformation. However, expression of E1A in most cases results in induction of programmed cell death (apoptosis), and only occasionally immortalization. Coexpression of the E1B gene is required to prevent induction of apoptosis and for complete morphological transformation to occur. In established immortal cell lines, high level expression of E1A can cause complete transformation in the absence of E1B.

The E1B-encoded proteins assist E1A in redirecting the cellular functions to allow viral replication. The E1B 55 kD and E433 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed.

Adenoviral-based vectors express gene product peptides at high levels. Adenoviral vectors have high efficiencies of infectivity, even with low titers of virus. Additionally, the virus is fully infective as a cell-free virion so injection of producer cell lines are not necessary. Adenoviral vectors achieve long-term expression of heterologous genes in vivo. Adenovirus is not associated with severe human pathology, the virus can infect a wide variety of cells and has a broad host-range, the virus can be produced in large quantities with relative ease, and the virus can be rendered replication defective by deletions in the early-region 1 ("E1") of the viral genome. Thus, vectors derived from human adenoviruses, in which at least the E1 region has been deleted and replaced by a gene of interest, have been used extensively for gene therapy experiments in the pre-clinical and clinical phase.

Adenoviral vectors for use with the present invention are derived from any of the various adenoviral serotypes, including, without limitation, any of the over 40 serotype strains of adenovirus, such as serotypes 2, 5, 12, 40, and 41. The adenoviral vectors used herein are replication-deficient and contain the gene of interest under the control of a suitable promoter, such as any of the promoters discussed below with reference to adeno-associated virus. For example, U.S. Pat. No. 6,048,551, incorporated herein by reference in its entirety, describes replication-deficient adenoviral vectors that include the human gene for the anti-inflammatory cytokine IL-10, as well as vectors that include the gene for the anti-inflammatory cytokine IL-1ra, under the control of the Rous Sarcoma Virus (RSV) promoter, termed Ad.RSVIL-10 and Ad.RSVIL-1ra, respectively.

Other recombinant adenoviruses, derived from any of the adenoviral serotypes, and with different promoter systems, can be used by those skilled in the art. For example, U.S. Pat. No. 6,306,652, incorporated herein by reference in its entirety, describes adenovirus vectors with E2A sequences, containing the hr mutation and the ts125 mutation, termed ts400, to prevent cell death by E2A overexpression, as well as vectors with E2A sequences, containing only the hr mutation, under the control of an inducible promoter, and vectors with E2A sequences, containing the hr mutation and the ts125 mutation (ts400), under the control of an inducible promoter.

Moreover, "minimal" adenovirus vectors as described in U.S. Pat. No. 6,306,652 will find use with the present invention. Such vectors retain at least a portion of the viral genome that is required for encapsidation of the genome into virus particles (the encapsidation signal), as well as at least one copy of at least a functional part or a derivative of the ITR. Packaging of the minimal adenovirus vector can be achieved by co-infection with a helper virus or, alternatively, with a packaging-deficient replicating helper system as described in U.S. Pat. No. 6,306,652.

Other useful adenovirus-based vectors for delivery of anti-inflammatory cytokines include the "gutless" (helper-dependent) adenovirus in which the vast majority of the viral genome has been removed (Wu et al., *Anesthes.* (2001) 94:1119-1132). Such "gutless" adenoviral vectors essentially create no viral proteins, thus allowing virally driven gene therapy to successfully ensue for over a year after a single administration (Parks, R. J., *Clin. Genet.* (2000) 58:1-11; Tsai et al., *Curr. Opin. Mol. Ther.* (2000) 2:515-523) and eliminates interference by the immune system. In addition, removal of the viral genome creates space for insertion of control sequences that provide expression regulation by systemically administered drugs (Burcin et al., *Proc. Natl. Acad. Sci. USA* (1999) 96:355-360), adding both safety and control of virally driven protein expression. These and other recombinant adenoviruses will find use with the present methods.

Adeno-Associated Virus Gene Delivery Systems

Adeno-associated virus (AAV) has been used with success to deliver genes for gene therapy. The AAV genome is a linear, single-stranded DNA molecule containing about 4681 nucleotides. The AAV genome generally comprises an internal, nonrepeating genome flanked on each end by inverted terminal repeats (ITRs). The ITRs are approximately 145 base pairs (bp) in length. The ITRs have multiple functions, including providing origins of DNA replication, and packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV has been engineered to deliver genes of interest by deleting the internal nonrepeating portion of the AAV genome (i.e., the rep and cap genes) and inserting a heterologous gene (in this case, the gene encoding the anti-inflammatory cytokine) between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

AAV is a helper-dependent virus; that is, it requires coinfection with a helper virus (e.g., adenovirus, herpesvirus or vaccinia), in order to form AAV virions. In the absence of coinfection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells coinfected with a canine adenovirus.

Recombinant AAV virions comprising the anti-inflammatory cytokine coding sequence may be produced using a variety of art-recognized techniques described more fully below. Wild-type AAV and helper viruses may be used to provide the necessary replicative functions for producing rAAV virions (see, e.g., U.S. Pat. No. 5,139,941, incorporated herein by reference in its entirety). Alternatively, a plasmid, containing helper function genes, in combination with infection by one of the well-known helper viruses can be used as the source of replicative functions (see e.g., U.S. Pat. No. 5,622,856 and U.S. Pat. No. 5,139,941, both incorporated herein by reference in their entireties). Similarly, a plasmid, containing accessory function genes can be used in combination with infection by wild-type AAV, to provide the necessary replicative functions. These three approaches, when used in combination with a rAAV vector, are each sufficient to produce rAAV virions. Other approaches, well known in the art, can also be employed by the skilled artisan to produce rAAV virions.

In a preferred embodiment of the present invention, a triple transfection method (described in detail in U.S. Pat. No. 6,001,650, incorporated by reference herein in its entirety) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations.

As explained herein, the AAV helper function vector encodes the "AAV helper function" sequences (i.e., rep and cap), which function in trans for productive AAV replication and encapsidation. Preferably, the AAV helper function vector supports efficient AAV vector production without generating any detectable wt AAV virions (i.e., AAV virions containing functional rep and cap genes). An example of such a vector, pHLP19, is described in U.S. Pat. No. 6,001,650, incorporated herein by reference in its entirety. The rep and cap genes of the AAV helper function vector can be derived from any of the known AAV serotypes, as explained above. For example, the AAV helper function vector may have a rep gene derived from AAV-2 and a cap gene derived from AAV-6; one of skill in the art will recognize that other rep and cap gene combinations are possible, the defining feature being the ability to support rAAV virion production.

The accessory function vector encodes nucleotide sequences for non-AAV-derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus (other than herpes simplex virus type-1), and vaccinia virus. In a preferred embodiment, the accessory function plasmid pLadeno5 is used (details regarding pLadeno5 are described in U.S. Pat. No. 6,004,797, incorporated herein by reference in its entirety). This plasmid provides a complete set of adenovirus accessory functions for AAV vector production, but lacks the components necessary to form replication-competent adenovirus.

In order to further an understanding of AAV, a more detailed discussion is provided below regarding recombinant AAV expression vectors and AAV helper and accessory functions Recombinant AAV Expression Vectors Recombinant AAV (rAAV) expression vectors are constructed using known techniques to at least provide as operatively linked components in the direction of transcription, control elements including a transcriptional initiation region, the anti-inflammatory polynucleotide of interest and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793-801; Bems, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable polynucleotide molecules for use in AAV vectors will be less than about 5 kilobases (kb) in size. The selected polynucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

The AAV expression vector which harbors the polynucleotide molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.* 158:97-129; Kotin (1994) *Human Gene Therapy* 5:793-801; Shelling and Smith (1994) *Gene Therapy* 1:165-169; and Zhou et al. (1994) *J. Exp. Med.* 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

For the purposes of the invention, suitable host cells for producing rAAV virions from the AAV expression vectors include microorganisms, yeast cells, insect cells, and mammalian cells, that can be, or have been, used as recipients of a heterologous DNA molecule and that are capable of growth in, for example, suspension culture, a bioreactor, or the like. The term includes the progeny of the original cell which has been transfected. Thus, a "host cell" as used herein generally refers to a cell which has been-transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly, Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241-247; McPherson et al. (1985) *Virology* 147:217-222; Schlehofer et al. (1986) *Virology* 152:110-117.

Alternatively, accessory functions can be provided using an accessory function vector as defined above. See, e.g., U.S. Pat. No. 6,004,797 and International Publication No. WO 01/83797, incorporated herein by reference in its entirety. Nucleic acid sequences providing the accessory functions can be obtained from natural sources, such as from the genome of an adenovirus particle, or constructed using recombinant or synthetic methods known in the art. As explained above, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions*, in I CRC *Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, recently reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions. A "recombinant AAV virion," or "rAAV virion" is defined herein as an infectious, replication-defective virus including an AAV protein shell, encapsidating a heterologous nucleotide sequence of interest which is flanked on both sides by AAV ITRs.

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60*C. for, e.g., 20 minutes or more. This treatment effectively inactivates only the helper virus since AAV is extremely heat stable while the helper adenovirus is heat labile.

The resulting rAAV virions containing the nucleotide sequence of interest can then be used for gene delivery using the techniques described below.

Compositions and Delivery

A. Compositions

Once produced, the vectors (or virions) encoding the anti-inflammatory cytokine, will be formulated into compositions suitable for delivery. Compositions will comprise sufficient genetic material to produce a therapeutically effective amount of the anti-inflammatory cytokine of interest, i.e., an amount sufficient to reduce or ameliorate pain. The compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

One particularly useful formulation comprises the vector or virion of interest in combination with one or more dihydric or polyhydric alcohols, and, optionally, a detergent, such as a sorbitan ester. See, for example, International Publication No. WO 00/32233.

As is apparent to those skilled in the art in view of the teachings of this specification, an effective amount can be empirically determined. Representative doses are detailed below. Administration can be effected in one dose, continuously or intermittently throughout the course of treatment. Methods of determining the most effective means and dosages of administration are well known to those of skill in the art and will vary with the vector, the composition of the therapy, the target cells, and the subject being treated. Single and multiple administrations can be carried out with the dose level and pattern being selected by the treating physician.

As shown in the examples below, one particularly effective way to produce long-term alleviation of pain involves administering two or more doses of IL-10 at close intervals, e.g., at less than 10 days apart, preferably less than 5 days apart, more preferably less than 4 days apart, such as at 3 . . . 2 . . . 1 . . . etc. and any amount of time within the stated ranges.

If multiple doses are administered, the first formulation administered can be the same or different than the subsequent formulations. Thus, for example, the first administration can be in the form of an adenovirus vector and the second administration in the form of an adenovirus vector, plasmid DNA, an AAV virion, a subunit vaccine composition, or the like. Moreover, subsequent delivery can also be the same or different than the second mode of delivery.

It should be understood that more than one transgene can be expressed by the delivered recombinant vector. For example, the recombinant vectors can encode more than one anti-inflammatory cytokine. Alternatively, separate vectors, each expressing one or more different transgenes, can also be delivered to the nervous system as described herein. Thus, multiple anti-inflammatory cytokines can be delivered concurrently or sequentially. Furthermore, it is also intended that the vectors delivered by the methods of the present invention be combined with other suitable compositions and therapies. For instance, other pain alleviators and analgesics, such as anti-prostaglandins, including, without limitation, cyclooxygenase-2 (COX-2) inhibitors, 5-lipoxygenase (5-LOX) inhibitors, and the like, can be coadministered with the compositions of the invention. Other compounds for delivery include agents used in the treatment of neuropathic pain such as, but not limited to, tricyclic antidepressants (e.g., amitriptyline, imipramine, desipramine), anti-convulsants (e.g., gabapentin, carbamazepine, phenyloin) and local anesthetics (e.g., mexiletine, lidocaine); and agents used in the treatment of inflammatory pain including, but not limited to, NSAIDs (e.g., ibuprofen, naprosyn sodium, aspirin, diclofenac sodium, indomethacin, toletin), steroids (e.g., methylprednisone, prednisone), analgesics (e.g., acetaminophen), and opiates (e.g., tramadol, demerol, darvon, vicodin, fentanyl).

B. Delivery

The recombinant vectors may be introduced into the nervous system, including into any cell or tissue of the CNS or peripheral nervous system, or cells or tissues in close proximity thereto. Thus, delivery can be, for example, into any neural tissue including, without limitation, peripheral nerves, the retina, dorsal root ganglia, neuromuscular junction, as well as the CNS, e.g., to target spinal cord glial cells, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue. The recombinant vectors be introduced either in vivo or in vitro (also termed ex vivo) to treat preexisting neuronal damage, neuropathies and other causes of neuropathic pain as defined above. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject. Additionally, neural progenitor cells can be transduced in vitro and then delivered to the CNS.

Suitable methods for the delivery and introduction of transduced cells into a subject have been described. For example, cells can be transduced in vitro by combining recombinant vectors with cells to be transduced in appropriate media, and those cells harboring the DNA of interest can be screened using conventional techniques such as Southern blots and/or PCR, or by using selectable markers. Transduced cells can then be formulated into pharmaceutical compositions, as described above, and the composition introduced into the subject by various techniques as described below, in one or more doses.

For in vivo delivery, the recombinant vectors will be formulated into pharmaceutical compositions and one or more dosages may be administered directly in the indicated manner. Therapeutically effective doses can be readily determined by one of skill in the art and will depend on the particular delivery system used. For AAV-delivered anti-inflammatory cytokines, a therapeutically effective dose will include on the order of from about $10^6$ to $10^{15}$ of the rAAV virions, more preferably $10^7$ to $10^{12}$, and even more preferably about $10^8$ to $10^{10}$ of the rAAV virions (or viral genomes, also termed "vg"), or any value within these ranges. For adenovirus-delivered anti-inflammatory cytokines, a therapeutically effective dose will include about $1\times10^6$ plaque forming units (PFU) to $1\times10^{12}$ PFU, preferably about $1\times10^7$ PFU to about $1\times10^{10}$ PFU, or any dose within these ranges which is sufficient to alleviate pain.

Generally, from 1 µl to 1 ml of composition will be delivered, such as from 0.01 to about 0.5 ml, for example about 0.05 to about 0.3 ml, such as 0.08, 0.09, 0.1, 0.2, etc. and any number within these ranges, of composition will be delivered.

Recombinant vectors, or cells transduced in vitro, may be delivered directly to neural tissue such as peripheral nerves, the retina, dorsal root ganglia, neuromuscular junction, as well as the CNS, e.g., to target spinal cord glial cells, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue, and the like, by injection into, e.g., the ventricular region, as well as to the striatum (e.g., the caudate nucleus or putamen of the striatum), spinal cord and neuromuscular junction, into the interstitial space, with a needle, catheter or related device, using techniques known in the art, such as by stereotactic injection (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000), epidural delivery, etc.

A particularly preferred method for targeting the nervous system, such as spinal cord glia, is by intrathecal delivery, rather than into the cord tissue itself. Such delivery presents many advantages. The targeted protein is released into the surrounding CSF and/or tissues and unlike viruses, released proteins can penetrate into the spinal cord parenchyma, just as after acute intrathecal injections. Indeed, intrathecal delivery of viral vectors can keep expression local. Moreover, in the case of IL-10, its brief half-life also serves to keep it local following intrathecal gene therapy; that is, its rapid degradation keeps the active protein concentrated close to its site of release. An additional advantage of intrathecal gene therapy is that the intrathecal route mimics lumbar puncture administration (i.e., spinal tap) already in routine use in humans.

Another method for delivery is by administration into the epidural space. The epidural space occupies the vertebral canal between the periosteum lining the canal and the dura. The epidural space is readily approached through the lumbar area. Generally, a needle, catheter or the like is inserted in the midline and passes through the skin, fascia, supraspinous and interspinous ligaments, and the ligamentum flavum prior to reaching the extradural space. However, administration can also be through the thoracic area. Methods for delivering agents epidurally are well known in the art. See, e.g., *Textbook of Surgery*, (D. C. Sabiston, ed.) W.B. Saunders Company.

Another preferred method for administering the recombinant vectors or transduced cells is by delivery to dorsal root ganglia (DRG) neurons, e.g., by injection into the epidural space with subsequent diffusion to DRG. For example, the recombinant vectors or transduced cells can be delivered via intrathecal cannulation under conditions where the protein is diffused to DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a convection-enhanced delivery (CED) system. In this way, recombinant vectors can be delivered to many cells over large areas of the CNS. Moreover, the delivered vectors efficiently express transgenes in CNS cells (e.g., glial cells). Any convection-enhanced delivery device may be appropriate for delivery of recombinant vectors. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, a recombinant vector is delivered via CED devices as follows. A catheter, cannula or other injection device is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target. Moreover, because the methods described herein can be practiced such that relatively large areas of the subject take up the recombinant vectors, fewer infusion cannula are needed. Since surgical complications are related to the number of penetrations, this mode of delivery serves to reduce the side-effects seen with conventional delivery techniques. For a detailed description regarding CED delivery, see U.S. Pat. No. 6,309,634, incorporated herein by reference in its entirety.

Protein Delivery Techniques

As explained above, agents that act on proinflammatory cytokines, such as any of the anti-inflammatory cytokines and proinflammatory cytokine antagonists described herein, can be administered alone, without gene delivery, or in conjunction with gene therapy, to treat or prevent pain. Thus, for example, one or more of IL-10 (including viral IL-10), IL-1ra, IL-4, IL-13, TNFsr, alpha-MSH, TGF-β1, proinflammatory cytokine antagonists and/or other agents that act on proinflammatory cytokines, can be formulated into compositions and delivered to subjects prior to, concurrent with or subsequent to gene delivery of one or more of these agents. Alternatively, these agents can be delivered alone, without the genes, to subjects with existing pain.

Compositions will comprise a therapeutically effective amount of the agent such that pain is reduced or reversed. The compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991). The pharmaceutical compositions may comprise the compound or its pharmaceutically acceptable salt or hydrate as the active component.

In general, the agents will be formulated into compositions for oral (including buccal and sub-lingual), rectal, nasal, topical, pulmonary, vaginal or parenteral (including intramuscular, intraarterial, intrathecal, epidural, subcutaneous and intravenous) administration or in a form suitable for administration by inhalation or insufflation. The preferred manner of administration is into the nervous system, for example into any neural tissue including, without limitation, peripheral nerves, the retina, dorsal root ganglia, neuromuscular junction, as well as the CNS, e.g., to target spinal cord glial cells, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue, using any of the techniques described above with reference to recombinant vectors.

Preferably, the compositions are formulated in order to improve stability and extend the half-life of the active agent. For example, the active agent, such as IL-10, can be derivatized with polyethlene glycol (PEG). Pegylation techniques are well known in the art and include, for example, site-specific pegylation (see, e.g., Yamamoto et al., *Nat. Biotech.* (2003) 21:546-552; Manjula et al., *Bioconjug. Chem.* (2003) 14:464-472; Goodson and Katre, *Biotechnology* (1990) 8:343-346; U.S. Pat. No. 6,310,180 incorporated herein by reference in its entirety), pegylation using size exclusion reaction chromatography (see, e.g., Fee, C. J., *Biotechnol. Bioeng.* (2003) 82:200-206), and pegylation using solid phase (see, e.g., Lu and Felix, *Pept. Res.* (1993) 6:140-146). For other methods of pegylation see, e.g., International Publication No. WO 02/26265, U.S. Pat. Nos. 5,206,344 and 6,423,685, all incorporated herein by reference in their entireties, as well as reviews by Harris and Chess, *Nat. Rev. Drug. Discov.* (2003) 2:214-221; Greenwald et al., *Adv. Drug. Deliv. Rev.* (2003) 55:217-256; and Delgado et al., *Crit. Rev. Ther. Drug Carrier Syst.* (1992) 2:249-304.

Moreover, the active agent may be fused to antibodies or peptides, to improve stability and extend half-life, using techniques well known in the art. For example, the active agent may be fused to immunoglobulin molecules in order to provide for sustained release. One convenient technique is to fuse the agent of interest to the Fc portion of an IgG such as a human or mouse IgG2a with a noncytolytic mutation. See, e.g., Jiang et al., *J. Biochem.* (2003) 133:423-427; Adachi et al., *Gene Ther.* (2002) 9:577-583; and U.S. Pat. No. 6,410,008, incorporated herein by reference in its entirety. A non-lytic recombinant human IL-10/Fc chimera is commercially available from Sigma Chemical Co. (St. Louis, Mo.).

Additionally, the active agent can be fused to an enzymatically inactive polypeptide, such as albumin, as well as enzymes that have enzymatic activity in an organism other than the organism to which the agent will be delivered. For example, useful polypeptides include plant enzymes, porcine or rodent glycosyltransferases, and α-1,3-galactosyltransferases. See, e.g., Sandrin et al., *Proc. Natl. Acad. Sci. USA* (1993) 90:11391 and U.S. Pat. No. 6,403,077, incorporated herein by reference in its entirety. Other methods for stabilizing the agent of interest is to make the protein larger or less accessible to proteases, such as by introducing glycosylation sites and/or removing sites involved in activation (e.g., that target the protein for degradation).

Additionally, the active agent may be delivered in sustained-release formulations. Controlled or sustained-release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, the active agent can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

As explained above, administration can be effected in one dose, continuously or intermittently throughout the course of treatment. Methods of determining the most effective means and dosages of administration are well known to those of skill in the art and will vary with the formulation, the composition of the therapy, the target cells, and the subject being treated. Single and multiple administrations can be carried out with the dose level and pattern being selected by the treating physician.

One particularly effective way to produce long-term alleviation of pain involves administering two or more doses of IL-10 at close intervals, e.g., at less than 10 days apart, preferably less than 5 days apart, more preferably less than 4 days apart, such as at 3 ... 2 ... 1 ... etc. and any amount of time within the stated ranges.

If multiple doses are administered, the first formulation administered can be the same or different than the subsequent formulations. Thus, for example, the first administration can be in the form of a subunit vaccine composition, and the second administration in the form of a subunit vaccine composition, an adenovirus vector, an AAV virion, a DNA plasmid, etc. Moreover, subsequent delivery can also be the same or different than the second mode of delivery.

Pain Models

The ability of an anti-inflammatory cytokine to treat pain can be evaluated by any of the accepted pain models known in the art. Examples of such models are as follows.

Tail Flick Model: The tail-flick test (D'Amour et al., *J. Pharmacol. Exp. and Ther.* (1941) 72:74-79) is a model of acute pain. A gently-restrained rat is placed on a test stage such that a focused light source beams on the dorsal or ventral surface of the rat's tail. A photosensor is present on the test stage located opposite the light source. To begin the test, the rat's tail blocks the light, thus preventing the light reaching the photosensor. Latency measurement begins with the activation of the light source. When a rat moves or flicks its tail, the photosensor detects the light source and stops the measurement. The test measures the period of time (duration) that the rat's tail remains immobile (latent). Rats are tested prior to administration thereto of a compound of interest and then at various times after such administration.

Rat Tail Immersion Model:

The rat tail immersion assay is also a model of acute pain. A rat is loosely held in hand while covered with a small folded thin cotton towel with its tail exposed. The tip of the tail is dipped into a, e.g., 52° C. water bath to a depth of two inches. The rat responds by either wiggling of the tail or withdrawal of the tail from the water; either response is scored as the behavioral end-point. Rats are tested for a tail response latency (TRL) score prior to administration thereto of a compound of interest and then retested for TRL at various times after such administration.

Carrageenan-induced Paw Hyperalgesia Model:

The carrageenan paw hyperalgesia test is a model of inflammatory pain. A subcutaneous injection of carrageenan is made into the left hindpaws of rats. The rats are treated with a selected agent before, e.g., 30 minutes, the carrageenan injection or after, e.g., two hours after, the carrageenan injection. Paw pressure sensitivity for each animal is tested with an analgesymeter three hours after the carrageenan injection. See, Randall et al., *Arch. Int. Pharmacodyn.* (1957) 111:409-419.

The effects of selected agents on carrageenan-induced paw edema can also be examined. This test (see, Vinegar et al., *J. Phamacol. Exp. Ther.* (1969) 166:96-103) allows an assessment of the ability of a compound to reverse or prevent the formation of edema evoked by paw carrageenan injection. The paw edema test is carried out using a plethysmometer for paw measurements. After administration of a selected agent, a carrageenan solution is injected subcutaneously into the lateral foot pad on the plantar surface of the left hind paw. At three hours post-carrageenan treatment, the volume of the treated paw (left) and the un-treated paw (right) is measured using a plethysmometer.

Formalin Behavioral Response Model:

The formalin test is a model of acute, persistent pain. Response to formalin treatment is biphasic (Dubuisson et al., *Pain* (1977) 4:161-174). The Phase I response is indicative of a pure nociceptive response to the irritant. Phase 2, typically beginning 20 to 60 minutes following injection of formalin, is thought to reflect increased sensitization of the spinal cord.

Von frey Filament Test:

The effect of compounds on mechanical allodynia can be determined by the von Frey filament test in rats with a tight ligation of the L-5 spinal nerve: a model of painful peripheral neuropathy. The surgical procedure is performed as described by Kim et al., *Pain* (1992) 50:355-363. A calibrated series of von Frey filaments are used to assess mechanical allodynia (Chaplan et al., *J. Neurosci. Methods* (1994) 53:55-63). Filaments of increasing stiffness are applied perpendicular to the midplantar surface in the sciatic nerve distribution of the left hindpaw. The filaments are slowly depressed until bending occurred and are then held for 4-6 seconds. The filament application order and number of trials were determined by the up-down method of Dixon (Chaplan et al., supra). Flinching and licking of the paw and paw withdrawal on the ligated side are considered positive responses.

Chronic Constriction Injury:

Heat and cold allodynia responses can be evaluated as described below in rats having a chronic constriction injury (CCI). A unilateral mononeuropathy is produced in rats using the chronic constriction injury model described in Bennett et al., *Pain* (1988) 33:87-107. CCI is produced in anesthetized rats as follows. The lateral aspect of each rat's hind limb is shaved and scrubbed with Nolvasan. Using aseptic techniques, an incision is made on the lateral aspect of the hind limb at the mid-thigh level. The biceps femoris is bluntly dissected to expose the sciatic nerve. On the right hind limb of each rat, four loosely tied ligatures (for example, Chromic gut 4.0; Ethicon, Johnson and Johnson, Somerville, N.J.) are made around the sciatic nerve approximately 1-2 mm apart. On the left side of each rat, an identical dissection is performed except that the sciatic nerve is not ligated (sham). The muscle is closed with a continuous suture pattern with, e.g., 4-0 Vicryl (Johnson and Johnson, Somerville, N.J.) and the overlying skin is closed with wound clips. The rats are ear-tagged for identification purposes and returned to animal housing.

The Hargreaves Test:

The Hargreaves test (Hargreaves et al., *Pain* (1998) 32:77-88) is also a radiant heat model for pain. CCI rats are tested for thermal hyperalgesia at least 10 days post-op. The test apparatus consists of an elevated heated (80-82° F.) glass platform. Eight rats at a time, representing all testing groups, are confined individually in inverted plastic cages on the glass floor of the platform at least 15 minutes before testing. A radiant heat source placed underneath the glass is aimed at the plantar hind paw of each rat. The application of heat is continued until the paw is withdrawn (withdrawal latency) or the time elapsed is 20 seconds. This trial is also applied to the sham operated leg. Two to four trials are conducted on each paw, alternately, with at least 5 minutes interval between trials. The average of these values represents the withdrawal latency.

Cold Allodynia Model:

The test apparatus and methods of behavioral testing is described in Gogas et al., *Analgesia* (1997) 3:111-118. The apparatus for testing cold allodynia in neuropathic (CCI) rats consists of a Plexiglass chamber with a metal plate 6 cm from the bottom of the chamber. The chamber is filled with ice and water to a depth of 2.5 cm above the metal plate, with the temperature of the bath maintained at 0-4° C. throughout the test. Each rat is placed into the chamber individually, a timer started, and the animal's response latency was measured to the nearest tenth of a second. A "response" is defined as a rapid withdrawal of the right ligated hindpaw completely out of the water when the animal is stationary and not pivoting. An exaggerated limp while the animal is walking and turning is not scored as a response. The animals' baseline scores for withdrawal of the ligated leg from the water typically range from 7-13 seconds. The maximum immersion time is 20 seconds with a 20-minute interval between trials.

2. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Subjects

Pathogen-free adult male Sprague-Dawley rats (300-450 g; Harlan Labs, Madison, Wis.) were used in all experiments. Rats were housed in temperature- and light-controlled rooms with standard rodent chow and water available ad libitum. Behavioral testing was performed during the light cycle.

Drugs

Sterile aliquots of recombinant gp120 (1 µg/µl; product #1021; lot #8D159M2; ImmunoDiagnostics, Bedford, Mass.) were stored at −75° C. At the time of testing, gp120 was slowly thawed and maintained on crushed ice. Each aliquot of gp120 was used within 30 min of thawing. The gp120 was diluted to a concentration of 0.5 µg/µl in a 0.1% rat serum albumen vehicle (RSA; Life Technologies, Gaithersburg, Md., in Dulbecco's Phosphate Buffered Saline (DPBS, 1×), 0.10 m pore-filtered, pH 7.2, cat#14190-144; Gibco, Invitrogen Corp, Grand Island, N.Y.) as described previously (Milligan et al., *J. Neurosci.* (2001) 21:2808-2819).

Zymosan (yeast cell walls; Sigma Chemical Co., St. Louis, Mo.) was made fresh daily by suspension in a vehicle of incomplete Freund's adjuvant (Sigma Chemical Co., St. Louis, Mo.). The final concentrations were 0, 0.08, or 3.2 µg/µl as described previously (Milligan et al., *J. Neurosci.* (2003) 23:1026-1040).

For experiments using adenovirus, a replication-defective adenovirus expression vector containing the cDNA encoding for human IL-10 (AD-IL10) driven by the Rous Sarcoma Virus (RSV) promoter was used and is described in U.S. Pat. No. 6,048,551. The control adenovirus (AD-Control) was an analogous adenovirus expression vector in which the RSV promoter directed the expression of the *E. coli* beta-galactosidase gene. Recombinant adenoviruses were grown by infecting 36 100-mm plates of Human Embryonic Kidney 293 (HEK293) cells ($5 \times 10^6$ cells/plate) at a multiplicity of 25 plaque-forming units/cell. The infected cells were collected after 48 hr, concentrated by low speed centrifugation, and resuspended in 20 ml of growth media (DMEM, 10% calf serum). After 4 freeze-thaw cycles, the cell lysates were layered on cesium chloride step gradients (1 ml of 1.4 g/ml cesium chloride/PBS cushion, 1.5 ml 1.25 g/ml cesium chloride/PBS step) and centrifuged in a Beckman SW 40 rotor for 1 hr at 36K rpm. Viral bands were harvested and further purified in isopycnic gradients consisting of 1.35 g/ml cesium chloride/PBS in a Beckman VTi65 rotor centrifuged for 2 hrs at 65K rpm. Mature viral particles were isolated and dialyzed for 1 hr against DPBS (Ix) and twice each for 2 hr against DPBS-3% sucrose. Dialysed virus preparations were stored as 10 µl aliquots at −80° C. Viral titers were determined by viral plaque assay as previously described (Schaack et al., *J. Virol.* (1995) 69:3920-3923).

For experiments with AAV, an AAV expression vector was produced (packaged and purified) as previously described (Zolotukhin et al., *Gene Ther.* (1999) 6:973-985). In brief, cotransfection of the proviral cassette with plasmid (pDG) that provides the AAV rep and cap genes in trans as well as adenoviral genes E2a, E4 and VA was conducted. The E1a and E1b genes were in the complimentary cell line, HEK 293. The vector cassette containing the cDNA encoding rat IL-10 (AAV-IL10) was driven by the hybrid CMV enhancer/chicken beta actin promoter/hybrid intron (pTR2-CB-rIL-10). The control AAV (AAV-Control) was an analogous AAV expression vector in which the CMV enhancer/chicken beta actin promoter directs the expression of the reporter gene UF11 encoding Jellyfish green florescent protein (GFP). Viral titers were determined by infectious center assay as previously described (Zolotukhin et al., *Gene Ther.* (1999) 6:973-985). Here, viral titers for rat IL-10 and UF11 of $2.6 \times 10^{13}$ physical particles (Dot blot)/ml and $1.32 \times 10^{13}$ physical particles/ml, respectively, were achieved. These titers correspond to $1.7 \times 10^{11}$ infectious particles/ml and $1.69 \times 10^{11}$ infectious particles/ml for rat IL-10 and UF11 (GFP), respectively.

For experiments using plasmid or "naked" DNA, free plasmid DNA was the identical plasmid engineered for transfection of AAV described above. In these studies, plasmid DNA encoding IL-10 (pTR2-CB-rIL-10) or GFP (pTR2-CB-GFP-TK-NEO (UF11)) was subcloned and purified similar to procedures described previously (Sambrook, J, Fritsch, E. R., Maniatis, T. *Molecular cloning*, $2^{nd}$ ed., Cold Spring Harbor Press, pp 1.38-1.39, 1989). After isolation procedures, plasmids (pDNA) were dialyzed for 1 hr against DPBS (1×) and twice each for 2 hr against DPBS-3% sucrose. Dialysed pDNA preparations were stored as 300 µl aliquots at −80° C. The concentration of the pDNA-IL10 and pDNA-UF11 preparations were determined by 260 nm adsorption and were 4.2 µg/µl and 5.6 µg/µl respectively. Animals were given 100

μg pDNA for each injection day. There were a total of four injections during the 77 day experiment.

Behavioral Measures von Frey Test. The von Frey test (Chaplan et al., *J. Neurosci Meth.* (1994) 53:55-63) was performed within the sciatic and saphenous innervation area of the hindpaws as previously described (Milligan et al., *Brain Res.* (2000) 861:105-116; Chacur et al., *Pain* (2001) 94:231-244; Gazda et al., *J. Peripheral Nerv. Sys.* (2001) 6:111-129; Milligan et al., *J. Neurosci.* (2001) 21:2808-2819. Briefly, a logarithmic series of 10 calibrated Semmes-Weinstein monofilaments (von Frey hairs; Stoelting, Wood Dale, Ill.) was applied randomly to the left and right hind paws to determine the stimulus intensity threshold stiffness required to elicit a paw withdrawal response. Log stiffness of the hairs is determined by log 10 (milligrams×10). The 10 stimuli had the following log-stiffness values (values in milligrams are given in parenthesis): 3.61 (407 mg), 3.84 (692 mg), 4.08 (1202 mg), 4.17 (1479 mg), 4.31 (2041 mg), 4.56 (3630 mg), 4.74 (5495 mg), 4.93 (8511 mg), 5.07 (11,749 mg), and 5.18 (15,136 mg). The range of monofilaments used in these experiments (0.407-15.136 gm) produces a logarithmically graded slope when interpolating a 50% response threshold of stimulus intensity [expressed as log 10 (milligrams×10)] (Chaplan et al., *J Neurosci Meth*. (1994) 53:55-63). Assessments were made prior to (baseline) and at specific times after peri-sciatic and intrathecal drug administration, as detailed below for each experiment. Behavioral testing was performed blind with respect to drug administration. The behavioral responses were used to calculate the 50% paw withdrawal threshold (absolute threshold), by fitting a Gaussian integral psychometric function using a maximum-likelihood fitting method (Harvey, *Behav. Res. Meth. Instrum. Comput.* (1986) 18:623-632; Treutwein and Strasburger, *Percept. Psycholphys.* (1999) 61:87-106), as described in detail previously (Milligan et al., *Brain Res.* (2000) 861:105-116). This fitting method allows parametric statistical analyses (Milligan et al., *Brain Res.* (2000) 861:105-116).

Hargreaves Test.

Thresholds for behavioral response to heat stimuli applied to each hind paw were assessed using the Hargreaves test (Hargreaves et al., *Pain* (1998) 32:77-88), as previously described (Milligan et al., *Brain Res.* (2000) 861:105-116). Briefly, baseline (BL) paw withdrawal values were calculated from an average of 3-6 consecutive withdrawal latencies of both the left and right hind paws measured during a 1 hr period. Voltage to the heat source was adjusted to yield BL latencies ranging 8-12 sec and a cut off time of 20 sec was imposed to avoid tissue damage. This procedure was followed by intrathecal injections and a timecourse of post-drug behavioral assessments, as described below. Behavioral testing was performed blind with respect to drug administration. The order of paw testing varied randomly.

Surgery and Microinjections

Chronic Intrathecal Catheters.

Lumbosacral intrathecal (intrathecal) catheters were constructed and implanted by lumbar approach as previously described in detail (Milligan et al., *J. Neurosci. Meth.* (1999) 90:81-86; Milligan et al., (2003) in Pain Research Methods and Protocols: Methods of Molecular Medicine (Luo D., ed.), in press. New York: Humana Press). The indwelling catheters were used to microinject recombinant adenovirus, recombinant AAV, gp120, or vehicle into the CSF space surrounding the lumbosacral spinal cord. All intrathecal microinjections were performed as detailed previously, using an 8 μl void volume to ensure complete drug delivery (Milligan et al., *J. Neurosci. Meth.* (1999) 90:81-86). All catheter placements were verified upon completion of behavioral testing by visual inspection. Data were only analyzed from animals with catheters verified as having the catheter tip within the CSF space at the lumbosacral spinal level.

Chronic Peri-Sciatic Catheters.

Peri-sciatic catheters were constructed and implanted at mid-thigh level of the left hindleg as previously described (Chacur et al., *Pain* (2001) 94:231-244; Gazda et al., *J. Peripheral Nerv. Sys.* (2001) 6:111-129; Milligan et al., (2003) in Pain Research Methods and Protocols: Methods of Molecular Medicine (Luo D., ed.), in press. New York: Humana Press). This method allowed multi-day recovery of the animal from isoflurane anesthesia prior to unilateral microinjection of an immune activator around the sciatic nerve. This avoids the deleterious effects of anesthetics on the function of both immune (Lockwood et al., *Anesthes. Analg.* (1993) 77:769-774; Sato et al., *Masui*. (1995) 44:971-975; Miller et al., *Int. J. Microcirc. Clin. Exp.* (1996) 16:147-154) and glial cells (Feinstein et al., *J. Neurosurg. Anesthesiol.* 13:99-105; Tas et al., *Proc. Natl. Acad. Sci. USA* (1987) 84:5972-5975; Mantz et al., *Anesthesiology* (1993) 78:892-901; Miyazaki et al., *Anesthesiology* (1997) 86:1359-1366). In addition, this indwelling catheter method allowed peri-sciatic immune activation to be either acute (single injection of an immune activator) or chronic (repeated injections across weeks) (Milligan et al., *J. Neurosci.* (2003) 23:1026-1040). Both methods were used in the present experiments in awake, unrestrained rats. These acute and chronic peri-sciatic microinjections over the left sciatic nerve were performed as previously described (Chacur et al., *Pain* (2001) 94:231-244; Milligan et al., (2003) in Pain Research Methods and Protocols: Methods of Molecular Medicine (Luo D., ed.), in press. New York: Humana Press). Catheters were verified at sacrifice by visual inspection. Data were only analyzed from confirmed sites.

Chronic Constriction Injury (CCI).

CCI was created at mid-thigh level of the left hindleg as previously described (Bennett and Xie, *Pain* (1988) 33:87-107). Four sterile, absorbable surgical chromic gut sutures (cuticular 4-0, chromic gut, 27", cutting FS-2; Ethicon, Somerville, N.J.) were loosely tied around the gently isolated sciatic nerve under isoflurane anesthesia (Phoenix Pharm., St. Joseph, Mo.). The sciatic nerves of sham-operated rats were identically exposed but not ligated. Suture placements were verified at sacrifice by visual inspection. Data were only analyzed from confirmed sites.

Intrathecal Microinjection of AAV into Lumbosacral Spinal Cord.

For experiments injecting either AAV or pDNA, no chronic indwelling catheters were used. Instead, an acute catheter application method under brief isoflurane anesthesia (2% vol in oxygen) was employed. Here, a 25 cm PE-10 catheter, attached by a 30-gauge, 0.5-inch sterile needle to a sterile, 50 μl glass Hamilton syringe, was marked with black permanent ink at 7.7-7.8 cm from the open end and placed in a sterile, dry container until the time of injection. Rats were lightly anesthetized, the lower dorsal pelvic area was shaved and lightly swabbed with 70% alcohol. An 18-gauge sterile needle with the plastic hub removed was inserted between lumbar vertebrae L5 and L6. The open end of the PE-10 catheter was inserted into the 18-gauge needle and threaded to the 7.7 cm mark allowing for intrathecal PE-10 catheter-tip placement at the level of the lumbosacral enlargement. Drugs were injected with a 1 μl pre- and post 0.9% sterile, isotonic saline solution flush for 1 min. The PE-10 catheter was immediately withdrawn and the 18-gauge needle was removed from the L5-L6 inter-vertebral space. This acute injection method took 2-3 min to complete, and rats showed full recovery from anesthesia within 10 min. No abnormal motor behavior was observed in 100% of injections.

Cerebrospinal Fluid (CSF) Collection & Analysis

Immediately upon completion of behavioral testing in Examples 2 and 3, rats were overdosed with sodium pentobarbital (Abbot Laboratories, North Chicago, Ill.). Cervical and lumbosacral CSF were collected as previously described (Milligan et al., *J. Neurosci.* (2001) 21:2808-2819). These samples were flash frozen in liquid nitrogen and stored at −80° C. until analyzed by an enzyme linked immunosorbant assay (ELISA) to detect IL-10. As noted above, the IL-10 used was the human protein. This allowed virally driven IL-10 production to be assessed unconfounded by rat IL-10 by use of the R & D (Minneapolis, Minn.) human IL-10 ELISA kit (Cat # D1000) that detects human IL-10 but not rat IL-10 (manufacturer's information). CSF sample preparation was as previously described (Milligan et al., *J. Neurosci.* (2001) 21:2808-2819). The ELISAs were performed according to manufacturer's instructions.

Similarly, for the for the AAV and pDNA experiments, rats were treated with sodium pentobarbital as above, cervical and lumbosacral CSF collected as described above and samples were flash frozen until analysis using an ELISA to detect rat IL-10. Rat IL-10 was measured using the R & D (Minneapolis, Minn.) rat IL-10 ELISA kit. CSF sample preparation was as previously described (Milligan et al., *J. Neurosci.* (2001) 21:2808-2819). The ELISAs were performed according to manufacturer's instructions.

Dorsal Root Ganglion and Spinal Cord Tissue Collection & Analysis.

Immediately following collection of CSF in the AAV and pDNA experiments, L4-L6 dorsal root ganglia and lumbosacral spinal cord were collected ipsilateral and contralateral to CCI as well as bilateral cervical spinal cord according to methods previously described (Milligan et al., *J. Neurosci.* (2001) 21:2808-2819). These samples were quickly frozen on dry ice, transferred to pre-cooled labeled tubes and stored at −80° C. until analyzed by real time polymerase chain reaction to detect rat IL-10 mRNA, using techniques well known in the art. See, e.g., Giulietti et al., *Methods* (2001) 25:386-401.

Data Analysis

All statistical comparisons were computed using Statview 5.0.1 for the Macintosh. Data from the von Frey test were analyzed as the interpolated 50% threshold (absolute threshold) in log base 10 of stimulus intensity (monofilament stiffness in milligrams×10). Baseline measures for both the von Frey and Hargreaves tests, and dose response effects, were analyzed by one-way ANOVA. Timecourse measures for each behavioral test were analyzed by repeated measures ANOVAs followed by Fisher's protected least significant difference posthoc comparisons, where appropriate. Cervical and lumbosacral CSF IL-10 contents were analyzed by 2×2 ANOVA, followed by Fisher's protected least significant difference posthoc comparisons, where appropriate.

Example 1

Dose Response Characterization of Intrathecal Adenovirus Effects on Behavioral Sensitivity to Calibrated Touch/Pressure Stimuli The following experiment was conducted in order to define a range of adenovirus doses that produced no apparent change in threshold responses to calibrated touch/pressure stimuli. After assessment of baseline von Frey responses, rats were intrathecally injected with either 0 (n=7), 5 (n=5), 10 (n=5), 60 (n=2), 80 (n=7), 160 (n=4), 300 (n=2), or 600 (n=2)×$10^7$ plaque forming units (PFU) of adenovirus. Testing of 1200×$10^7$ PFU was attempted but terminated upon observing vestibulomotor effects of this dose. Rats injected intrathecally with adenovirus were assessed on the von Frey test 24 hr later.

Figure 1:
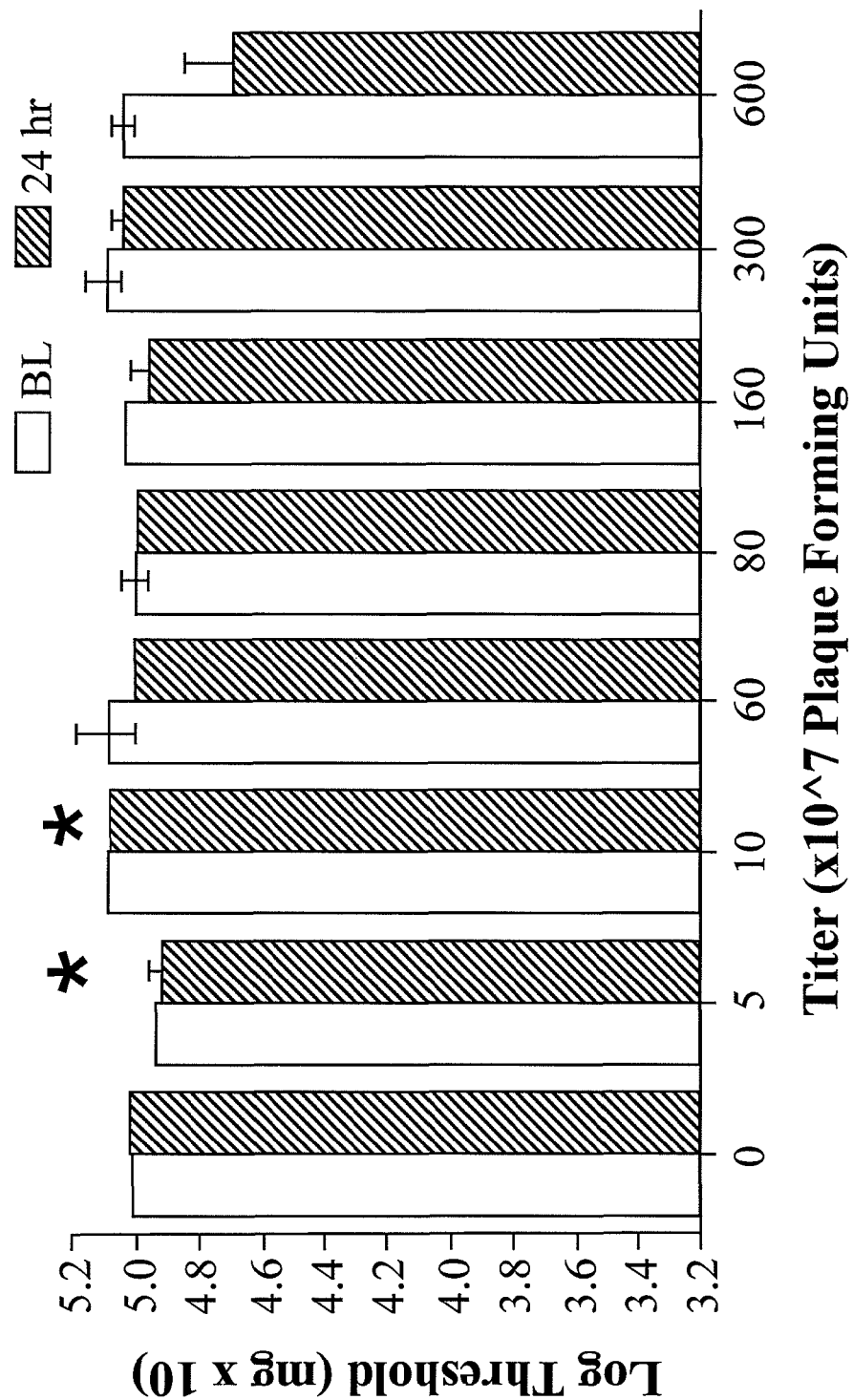
FIG. 1 shows the effect of increasing doses of intrathecal adenovirus on response threshold to calibrated touch/pressure stimuli. Lower doses of adenovirus had no detectable effect on response thresholds to calibrated touch/pressure stimuli as assessed by the von Frey test. The highest doses lowered the response threshold. The asterisks indicate the doses used in the remaining experiments. In this and all subsequent figures of data generated by the von Frey test, the y-axis represents the log transformation used for data analysis. The log transformation (followed by its mg force in parenthesis) of the stimuli used in the test were as follows: 3.61 (407 mg), 3.84 (692 mg), 4.08 (1,202 mg), 4.17 (1,479 mg), 4.31 (2,041 mg), 4.56 (3,630 mg), 4.74 (5,495 mg), 4.93 (8,511 mg), 5.07 (11,749 mg), and 5.18 (15,136 mg).

While doses of adenovirus up to 300×$10^7$ PFU had no reliable effect on responses to calibrated touch/pressure stimuli compared to vehicle controls, the highest dose (600×$10^7$ PFU) lowered the response threshold (FIG. 1). Pre-viral-injected BL values showed no reliable differences between groups ($F_{7,26}$=1.1715, p>0.14). One-Way ANOVA revealed a reliable effect of viral dose ($F_{7,26}$=5.694, p<0.005). Posthoc analysis revealed that only the 600×$10^7$ PFU adenovirus dose decreased response thresholds compared to controls (p<0.002). Adenovirus doses employed in subsequent experiments were restricted to the lower end of the dose range (see asterisks in FIG. 1) so to minimize the chances of virally induced alterations in pain sensitivity.

Example 2

Prevention of Intrathecal HIV-1 gp120 Induced Mechanical Allodynia by Intrathecal AD-IL10

It has previously been shown that spinal immune activation induced by intrathecal delivery of gp120, an envelope glycoprotein of human immunodeficiency virus-1, lowers the response threshold to touch/pressure stimuli (Milligan et al., *Brain Res.* (2000) 861:105-116; Milligan et al., *J. Neurosci.* (2001) 21:2808-2819). This pain response is the result of spinal cord glial activation and the release of the glial proinflammatory cytokines IL1 and TNF (Milligan et al., *Brain Res.* (2000) 861:105-116; Milligan et al., *J. Neurosci.* (2001) 21:2808-2819). Hence the ability of AD-IL10 to prevent this glially-driven mechanical allodynia was examined.

Based on pilot studies of adenoviral doses within the range defined in Example 1, 10×$10^7$ PFU of AD-IL10 in 10 μl was chosen for study. An equal volume of AD-Control (16×$10^7$ PFU in 10 μl) was administered to the control group. Rats were first assessed for their responses to the von Frey test prior to (baseline; BL) and on Days 4 and 5 after intrathecal AD-IL10 or AD-Control injection (n=8/group). Based on prior studies of this AD-IL10 vector, near maximal levels of virally directed IL-10 should be induced by this time (Gudmundsson et al., *Amer. J. Resp. Cell & Molec. Biol.* (1998) 19:812-818). The behavioral tests on Days 4 and 5 were performed to verify that neither this intrathecal adenoviral dose nor virally directed IL10 release had any observable confounding effect on this measure. Upon completion of the Day 5 test, all rats were injected with 3 μg gp120. This gp120 dose has previously been shown to produce mechanical allodynia as measured by the von Frey test (Milligan et al., *Brain Res.* (2000) 861:105-116; Milligan et al., *J. Neurosci.* (2001) 21:2808-2819; Milligan et al., *J. Pain* (2001) 6:326-333). Vehicle-injected controls were not included as it has repeatedly been demonstrated that this procedure has no effect on this behavioral measure (Milligan et al., *Brain Res.* (2000) 861:105-116; Milligan et al., *J. Pain* (2001) 6:326-333; Milligan et al., *J. Neurosci.* (2001) 21:2808-2819). Following gp120 injections, responses to touch/pressure stimuli were reassessed each 20 min for 120 min, in accordance with prior publications (Milligan et al., *Brain Res.* (2000) 861:105-116; Milligan et al., *J. Pain* (2001) 6:326-333; Milligan et al., *J. Neurosci.* (2001) 21:2808-2819). Upon completion of testing, cervical and lumbosacral CSF samples were collected for IL-10 analyses.

Figure 2:
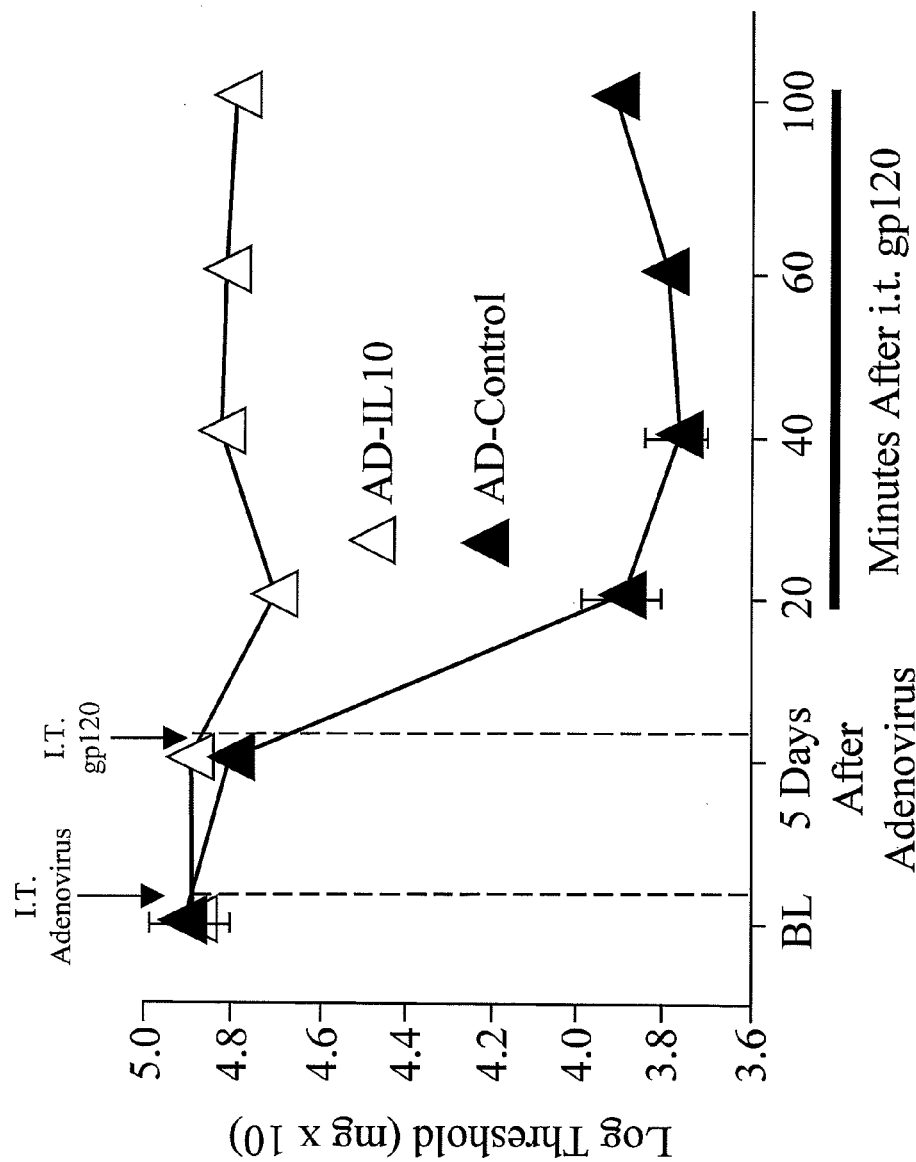
FIG. 2 shows that adenoviral-delivered IL-10 prevents intrathecal HIV-1 gp120-induced mechanical allodynia. After predrug (baseline; BL) assessment on the von Frey test, animals were injected intrathecally with either adenovirus encoding for IL-10 (AD-IL10) or a control adenovirus that encoded for beta-galactosidase (AD-Control). Response thresholds were reassessed 4 and 5 days later to test whether either the presence of virus and/or the presence of virally generated human IL-10 affected basal response thresholds. As seen, the Day 4 and Day 5 thresholds were not affected, compared to predrug BL. At this time, animals were injected intrathecally with HIV-gp120 at a dose (3 μg) previously shown to produce mechanical allodynia (Milligan et al., *Brain Res.* (2000) 861:105-116; Milligan et al., *J. Neurosci.* (2001) 21:2808-2819). Animals receiving intrathecal AD-Control followed by intrathecal gp120 developed mechanical allodynia as in previous experiments. In contrast, mechanical allodynia was prevented in animals receiving intrathecal AD-IL10.

Intrathecal administration of $10 \times 10^7$ AD-IL10 and AD-Control had no reliable effect on behavioral responses on the von Frey test compared to BL ($F_{1,21}=1.385$, p>0.25) (FIG. 2). Thus neither IL-10 released by the adenovirus nor the presence of this dose of adenovirus itself altered basal pain responsivity. As in previous studies (Milligan et al., *Brain Res.* (2000) 861:105-116; Milligan et al., *J. Neurosci.* (2001) 21:2808-2819), intrathecal gp120 produced robust mechanical allodynia in AD-Controls. In contrast, no mechanical allodynia developed in the AD-IL10 treated animals. Repeated measures ANOVA revealed a reliable main effect of IL-10 ($F_{1,21}=235.694$, p<0.0001).

Figure 3:
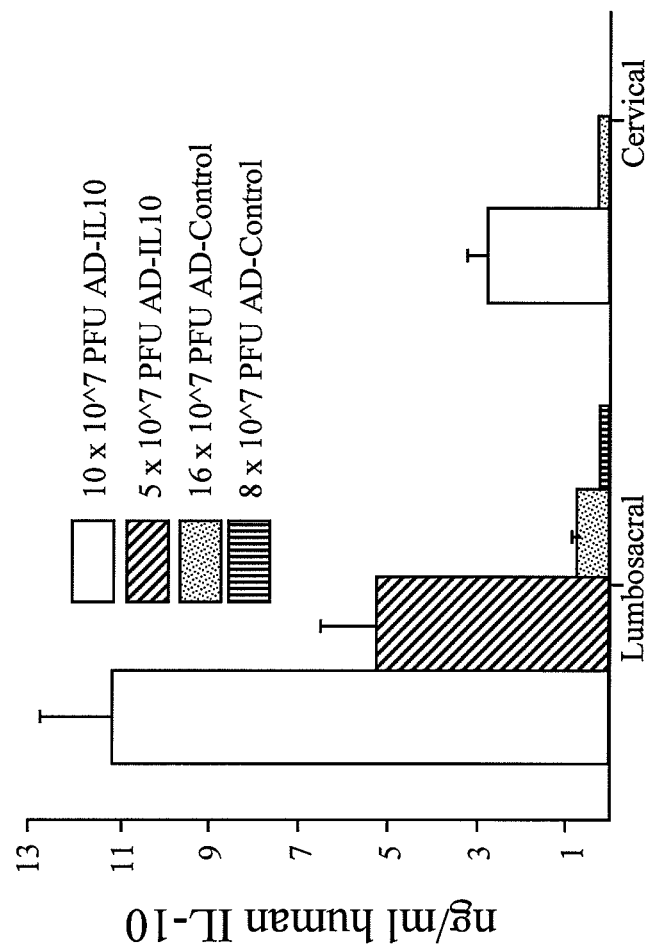
FIG. 3 shows human IL-10 levels in lumbosacral and cervical cerebrospinal fluid following lumbosacral adenovirus administration. Upon completion of behavioral testing (Day 5 after AD administration), lumbosacral and cervical CSF were collected from animals in Examples 2 and 3. These samples were assayed by ELISA for human IL-10. Since this ELISA does not detect rat IL-10, this allows virally induced IL-10 to be detected independent of rat IL-10. The $10\times10^7$ plaque forming units (PFU) injected in Experiment 2 for prevention of gp120-induced allodynia (see FIG. 2) produced far greater levels of human IL-10 in lumbosacral CSF than cervical CSF, indicating site specific effects of the virus. Comparable doses of AD-Control produced low values on this commercial ELISA test. The $5\times10^7$ PFU injected in Example 3 for prevention of sciatic inflammatory neuropathy (see FIG. 4) appears to have produced lower levels of human IL-10.

CSF collected upon completion of behavioral testing supported that AD-IL110 induced the release of human IL-10, concentrated at the lumbosacral level (FIG. 3). ANOVA revealed reliable main effects of IL-10 ($F_{1,21}=37.430$, p<0.0001) and site of CSF collection (lumbosacral vs. cervical; $F_{1,21}=46.240$, p>0.0001) and an interaction between ILI0 and site of CSF collection ($F_{1,21}=36.577$, p<0.0001), supporting that AD-ILI0 caused a greater site-specific effect of IL-10 concentrations at lumbosacral than cervical levels.

Example 3

Prevention of Sciatic Inflammatory Neuropathy (SIN) Induced Mechanical Allodynia by Intrathecal AD-IL10

The purpose of Examples 3 through 5 was to extend the results of Example 2 by examining the effect of AD-IL10 on neuropathic pain. Neuropathic pain arises as a consequence of inflammation and/or trauma of peripheral nerves. Neuropathic pain is poorly managed by currently available drugs developed to target neurons (for review, see (Watkins and Maier, *Physiol. Rev.* (2002) 82:981-1011).

AD-IL10 was tested for its ability to prevent mechanical allodynia induced by sciatic inflammatory neuropathy (SIN) as follows. Based on pilot studies of adenoviral doses within the range defined in Example 1, $5 \times 10^7$ PFU of AD-IL10 in 5 μl was chosen for study. An equal volume of AD-Control ($8 \times 10^7$ PFU in 5 μl) was administered to the control group. Rats were first assessed for their responses to the von Frey test prior to (BL) and again on Day 4 after intrathecal AD-ILI0 or AD-Control injection. As noted above, near maximal levels of virally directed IL-10 are expected by this time (Gudmundsson et al., *Amer. J. Resp. Cell & Molec. Biol.* (1998) 19:812-818). The behavioral test on Day 4 was performed to verify that neither this intrathecal adenoviral dose nor virally directed IL-10 release had any observable confounding effect on this measure. Immediately upon completion of the Day 4 test, all rats were peri-sciatically injected with either 4 or 160 μg zymosan (n=5-6/group). Peri-sciatic vehicle injected controls were not included as it has repeatedly been demonstrated that this procedure has no effect on this behavioral measure (Chacur et al., *Pain* (2001) 94:231-244; Gazda et al., *J. Peripheral Nerv. Sys.* (2001) 6:111-129; Milligan et al., *J. Neurosci.* (2003) 23:1026-1040). The 4 and 160 μg zymosan doses have previously been shown to induce unilateral and bilateral mechanical allodynia, respectively, in intrathecal catheterized rats (Milligan et al., *J. Neurosci.* (2003) 23:1026-1040). Behavioral. responses on the von Frey test were reassessed 3 and 24 hr later, in accordance with prior studies (Chacur et al., *Pain* (2001) 94:231-244; Gazda et al., *J. Peripheral Nerv. Sys.* (2001) 6:111-129; Milligan et al., *J. Neurosci.* (2003) 23:1026-1040). Upon completion of testing, cervical and lumbosacral CSF samples were collected for IL-10 analyses.

Figures 4A, 4B:
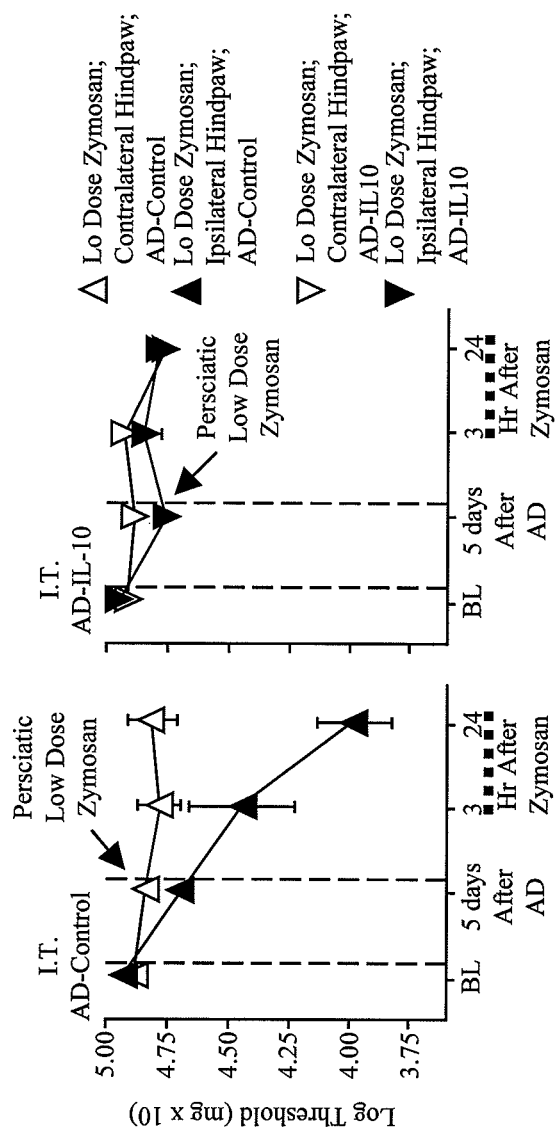

It was found that intrathecally administered AD-IL10 (a) successfully induced the site-specific release of human IL-10 into CSF and (b) prevented mechanical allodynia created in response to spinal cord immune activation. ANOVA revealed that AD-ILI0 and AD-Control had no effect on mechanical response thresholds measured 5 days after virus delivery, compared to BL ($F_{7,88}=0.686$, p>0.68) (FIG. 4). Hence, neither the presence of IL10 nor adenovirus had measurable effects on basal pain responses. As in our previous studies (Milligan et al., *J. Neurosci.* (2003) 23:1026-1040), low dose zymosan induced a unilateral allodynia (FIG. 4A) while higher dose zymosan induced a bilateral allodynia (FIG. 4C), compared to BL measures. Repeated measures ANOVA revealed reliable main effects of peri-sciatic zymosan dose ($F_{1,40}=12.093$, p<0.002), intrathecal IL-10 ($F_{1,40}=69.829$, p<0.0001), laterality ($F_{1,40}=22.315$, p<0.0001) and time after peri-sciatic zymosan application ($F_{1,40}=13.029$, p<0.001), and interactions between zymosan dose and intrathecal IL-10 ($F_{1,40}=6.161$, p<0.02) and between intrathecal IL-10 and laterality ($F_{1,40}=15.412$, p<0.001). Post hoc means comparison revealed that 4 μg zymosan induced mechanical allodynia in the left (ipsilateral) hindpaw compared to the right (contralateral) hindpaw in AD-control treated animals (p<0.0001). Mechanical response of the right hindpaw after 4 μg peri-sciatic zymosan did not differ from that at BL, indicating that 4 μg zymosan induced only a unilateral allodynia ipsilateral to the site of injection (p>0.45). In addition, posthoc analyses revealed that bilateral mechanical allodynia occurred in response to 160 μg peri-sciatic zymosan in AD-Control treated animals. That is, the thresholds for both the left and right paws were reliably different from BL measures (p<0.0001). Both ipsilateral (p>0.05) {FIG. 4B) and bilateral (p>0.15) (FIG. 4D) allodynias were blocked by AD-ILI0 as von Frey responses after peri-sciatic zymosan did not differ from BL.

Lumbosacral CSF collected upon completion of behavioral testing indicated that AD-ILI0 induced the release of human IL-10 (FIG. 3). One-way ANOVA revealed a reliable main effect of AD-ILI0 ($F_{1,10}=8.362$, p<0.02). FIG. 3 suggests a dose-dependent effect of $5 \times 10^7$ PFU AD-ILI0 (this example) compared to $10 \times 10^7$ PFU ILI0 (Example 2). As these assays were performed at separate times with different kits, these values were not statistically compared.

Example 4

Reversal of Sciatic Inflammatory Neuropathy (SIN) Induced Mechanical Allodynia by Intrathecal AD-ILI0

Example 3 revealed that intrathecal AD-IL10 prevented SIN-induced mechanical allodynia. In this example, the chronic SIN method (Milligan et al., *J. Neurosci.* (2003) 23:1026-1040) was used to test whether AD-ILI0 could reverse established SIN-induced mechanical allodynia. The dose of AD-ILI0 chosen for study was identical to that in Example 3 ($5 \times 10^7$ PFU of adenovirus in 5 μl). An equal volume of AD-Control ($8 \times 10^7$ PFU in 5 μl) was administered to the control group. Rats were assessed for their responses to the von Frey test prior to (BL) initiation of chronic SIN. Unilateral and bilateral chronic SIN were created as described previously (Milligan et al., *J. Neurosci.* (2003) 23:1026-1040). Peri-sciatic microinjection of zymosan (either 4 or 160 μg) was delivered immediately after BL (Day 0) and 2, 4, 6, 8, 10, and 12 days later. Von Frey tests were again performed on Days 1, 4, 8, 9, 10, 12 and 14. When behavioral testing and peri-sciatic injections occurred on the same day, behavioral testing preceded the peri-sciatic injection. The Day 8 behavioral assessment provided verification that the 4 μg and 160 μg chronic zymosan regimens produced unilateral and bilateral allodynia, respectively. Intrathecal adenovirus (either AD-IL10 or AD-Control) was delivered immediately after the Day 8 test (n=5-6/group). The Day 9-14 behavioral assessments allowed assessment of the ability of AD-IL10 to reverse well-established inflammatory neuropathy pain.

To examine whether ipsilateral territorial (skin innervated by the sciatic nerve), ipsilateral extra-territorial (skin innervated by the saphenous nerve), mirror-image territorial, and mirror-image extra-territorial allodynias were comparably affected by intrathecal ILI0 gene therapy, sciatic and saphenous innervation zones were separately tested at BL, Day 8 (prior to AD administration), and Days 12 and 14 (4 and 6 days after AD administration) in rats chronically administered 160 μg peri-sciatic zymosan.

Figures 5A, 5B:
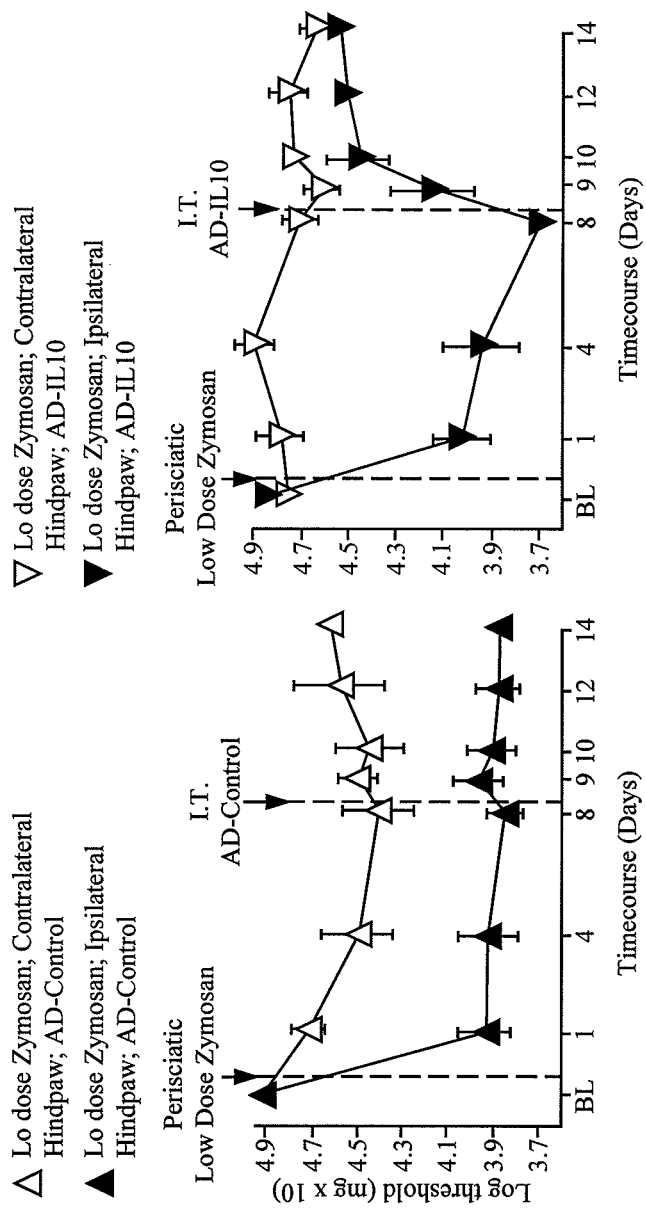
FIG. 5 shows that adenoviral IL-10 reverses chronic sciatic inflammatory neuropathy (SIN)-induced mechanical allodynias. After predrug (baseline; BL) assessment on the von Frey test, animals were repeatedly injected with either 4 or 160 µg zymosan to chronically induce unilateral (Panels A & B) or bilateral (Panels C and D) allodynia, respectively. These peri-sciatic zymosan injections continued throughout the behavioral testing time-course. After behavioral verification of allodynia on Day 8, all rats were injected intrathecally with either AD-Control (Panels A and C) or AD-IL10 (Panels B and D). Rats receiving AD-Control remained unilaterally (Panel A) or bilaterally (Panel C) allodynic throughout the assessment time-course. In contrast, both unilateral (Panel B) and bilateral (Panel D) allodynia were reversed by intrathecal AD-IL10.
Figures 5C, 5D:
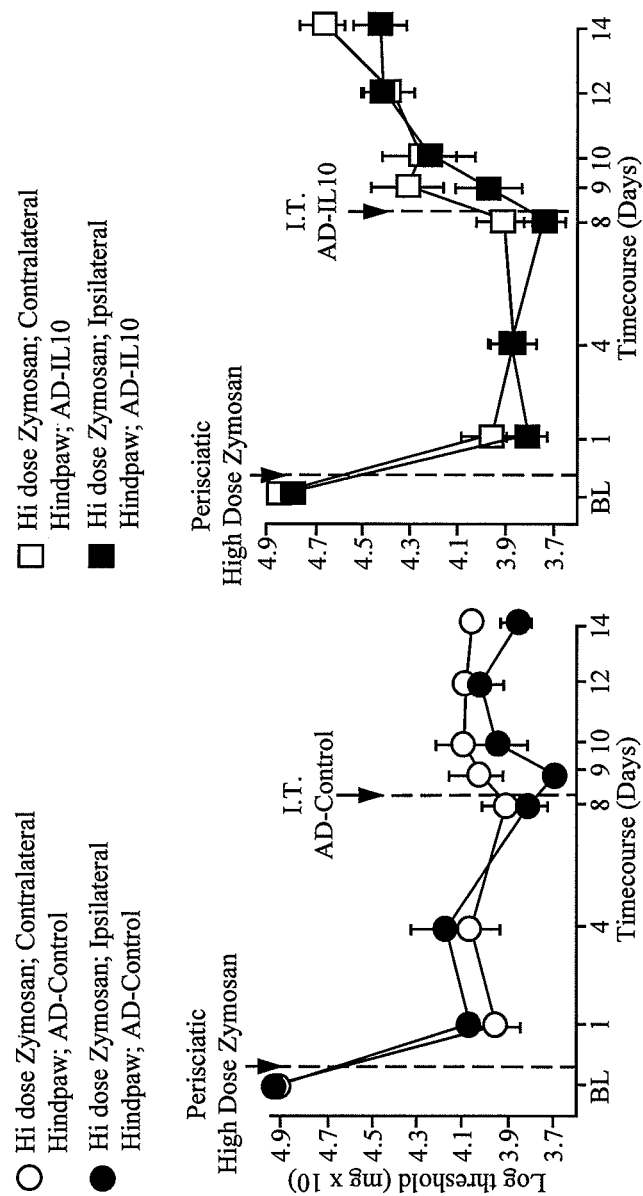

As previously reported (Milligan et al., *J. Neurosci.* (2003) 23:1026-1040), the repeated low (4 μg) and high (160 μg) zymosan protocols produced chronic unilateral and bilateral allodynia, respectively (FIG. 5). Eight days after initiation of zymosan administration, prior to adenoviral administration, ANOVA revealed reliable main effects of zymosan dose ($F_{1,36}=35.049$, $p<0.0001$) and laterality ($F_{1,36}=41.634$, $p<0.0001$) and time after peri-sciatic zymosan application ($F_{2,72}=7.537$, $p<0.001$), and interactions between zymosan dose and laterality ($F_{1,36}=35.919$, $p<0.0001$). Post hoc means comparison revealed that 4 μg zymosan induced mechanical allodynia in the left (ipsilateral) hindpaw compared to the right (contralateral) hindpaw in IL-10- and control virus-treated groups ($p<0.0001$). Mechanical responses of the right hindpaw after 4 μg peri-sciatic zymosan did not differ from that at BL ($p>0.66$), supporting that 4 μg zymosan induced only a unilateral allodynia ipsilateral to the site of injection. In addition, posthoc analyses supported that bilateral mechanical allodynia occurred in response to 160 μg peri-sciatic zymosan. That is, the thresholds of the left and right hindpaw did not differ ($p>0.29$) but the thresholds for both the left and right paws were reliably different from BL ($p<0.0001$).

After intrathecal adenoviral administration, AD-IL10 reversed these ongoing pathological pain states. That is, AD-IL10 reversed both ipsilateral and bilateral allodynias induced by peri-sciatic zymosan. ANOVA revealed reliable main effects of zymosan dose ($F_{1,36}=22.724$, $p<0.0001$), IL10 ($F_{1,36}=50.044$, $p<0.0001$), laterality ($F_{1,36}=35.532$, $p<0.0001$) and time after intrathecal adenoviral administration ($F_{3,108}=6.301$, $p<0.001$), and interactions between IL-10 and laterality ($F_{1,36}=35.919$, $p<0.05$). Posthoc means comparisons supported that IL-10 attenuated the allodynic effects of 4 μg zymosan in the ipsilateral hindpaw ($p<0.0001$, comparing ipsilateral hindpaw responses on day 8 vs. ipsilateral hindpaw responses on day 14 in the AD-IL10 group), whereas AD-control group hindpaw responses remained allodynic through day 14 ($p>0.8$, comparing ipsilateral hindpaw responses on day 8 vs. ipsilateral hindpaw responses on day 14 in the AD-control group).

IL-10 also attenuated allodynic effects of 1.60 μg zymosan in the contralateral hindpaw ($p<0.0001$, comparing contralateral hindpaw responses on day 8 vs. contralateral hindpaw responses on day 14 in the AD-IL10 group), whereas virus alone did not alter ongoing mirror image allodyma ($p>0.2$, comparing contralateral hindpaw responses on day 8 vs. contralateral hind paw responses on day 14 in the AD-control group)

Figures 6A, 6B:
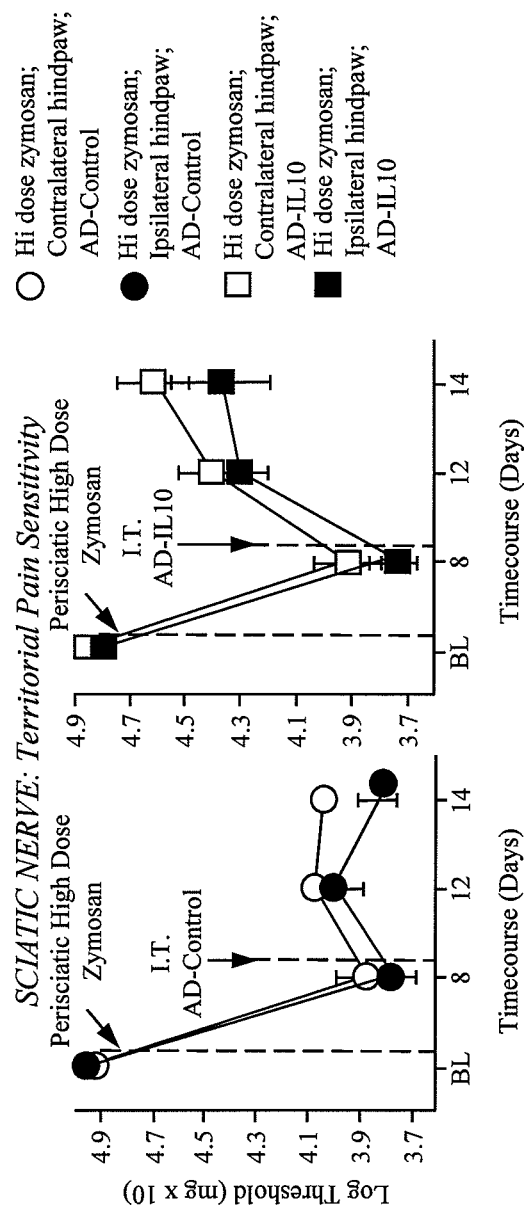
FIG. 6 shows that adenoviral IL-10 reverses both ipsilateral and mirror-image territorial and extra-territorial allodynias. Sciatic (territorial; Panels A and B) and saphenous (extra-territorial; Panels C and D) nerve innervation areas were separately tested prior to (baseline; BL) and after (Days 8, 12 and 14) chronic peri-sciatic 160 µg zymosan to induce bilateral mechanical allodynia. After the Day 8 assessment, AD-Control (Panels A and C) or AD-IL10 (Panels B and D) was administered. Comparable reversal by AD-IL10 was observed on Days 12 and 14 (4 and 6 days after AD, respectively) for ipsilateral and mirror image allodynias in both sciatic (Panel B) and saphenous innervation areas (Panel D) compared to AD-Control.

Differential testing of sciatic nerve (territorial) and saphenous nerve (extra-territorial) innervation areas of the ipsilateral and contralateral hind paws at BL ($F_{1,50}=1.352$, $p>0.90$) and at 8 days ($F_{1,50}=0.170$, $p>0.89$) after chronic peri-sciatic 160 μg zymosan (prior to AD administration) revealed no differences between groups (FIG. 6). At Day 8 (compared to BL), territorial and extraterritorial mechanical allodynia was observed in both the ipsilateral and mirror-image hind paws. ANOVA revealed main effect of time (BL vs. Day 8) after peri-sciatic zymosan ($F_{1,38}=22.398$, $p<0.0001$). Chronic peri-sciatic 160 μg zymosan produced reliable bilateral allodynia in both the territorial and extraterritorial innervation areas of both hind paws. ANOVA revealed no differences between the saphenous versus sciatic territories ($F_{1,36}=0.008$, $p>0.92$). In addition, no differences were found between ipsilateral vs. contralateral hindpaw responses ($F_{1,36}=0.716$, $p>0.40$). AD-ILI0 reliably reversed bilateral mechanical allodynia produced by peri-sciatic zymosan in both the territorial and extra-territorial innervation areas of both hindpaws. Repeated measures ANOVA revealed reliable main effects of IL-10 ($F_{1,32}=45.174$, $p<0.0001$) and time after viral treatment ($F_{2,64}=37.354$, $p<0.0001$), and an interaction between time after viral treatment and IL-10 ($F_{2,64}=15.265$, $p<0.0001$). Posthoc analyses revealed that AD-IL10 reliably reversed ipsilateral territorial ($p<0.05$), ipsilateral extraterritorial ($p<0.001$), mirror-image territorial ($p<0.01$), and mirror-image extraterritorial ($p<0.01$) allodynias compared to AD-Control treated animals. The degree of reversal of each of these allodynias was comparable at both Days 12 (4 days after AD-ILI0; $p<0.02$ comparing AD-ILI0 ipsilateral and contralateral saphenous and sciatic terrirotires to respective AD-Controls) and 14 (6 days after AD-IL10; $p<0.005$ comparing AD-IL10 ipsilateral and contralateral saphenous and sciatic terrirotires to respective AD-Controls).

Example 5

Reversal of Chronic Constriction Injury (CCI) Induced Mechanical Allodynia and Thermal Hyperalgesia by Intrathecal AD-ILI0

Example 4 revealed that adenoviral IL-10 can fully reverse SIN-induced pathological pain changes as measured by the von Frey test. While approximately 50% of clinical neuropathies are infective/inflammatory in nature, the rest involve peripheral nerve trauma (Said and Hontebeyrie-Joskowicz, *Res. Immunol* (1992) 143:589-599). Hence, it was important to determine whether adenoviral IL-10 could reverse traumatic neuropathy induced pain changes, in addition to its effectiveness on inflammatory neuropathy. A classic partial nerve injury model was used for study; namely, chronic constriction injury (CCI) (Bennett and Xie, *Pain* (1988) 33:87-107). The dose of AD-IL-10 chosen for study was identical to that in Examples 3 and 4 ($5\times10^7$ PFU of adenovirus in 5 μl). An equal volume of AD-Control ($8\times10^7$ PFU in 5 μl) was administered to the control group. Rats were assessed for their responses to the von Frey test and Hargreaves test prior to (BL) and again on Day 10 after CCI or sham surgery. This latter test allowed verification of the development of mechanical allodynia and thermal hyperalgesia in CCI rats, compared to controls. Immediately after the test on Day 10, all rats received intrathecal AD-IL10 or AD-Control (n=6/group). Von Frey and Hargreaves tests were again performed on Days 3, 5, 7, 14, 18, and 21 after viral administration. This corresponds to Days 13, 15, 17, 24, 28, and 31 after CCI or Sham surgery. These tests allowed assessment of (a) the ability of AD-IL10 to reverse well-established traumatic neuropathy pain and (b) the duration of AD-IL10 effectiveness.

Figures 7A, 7B:
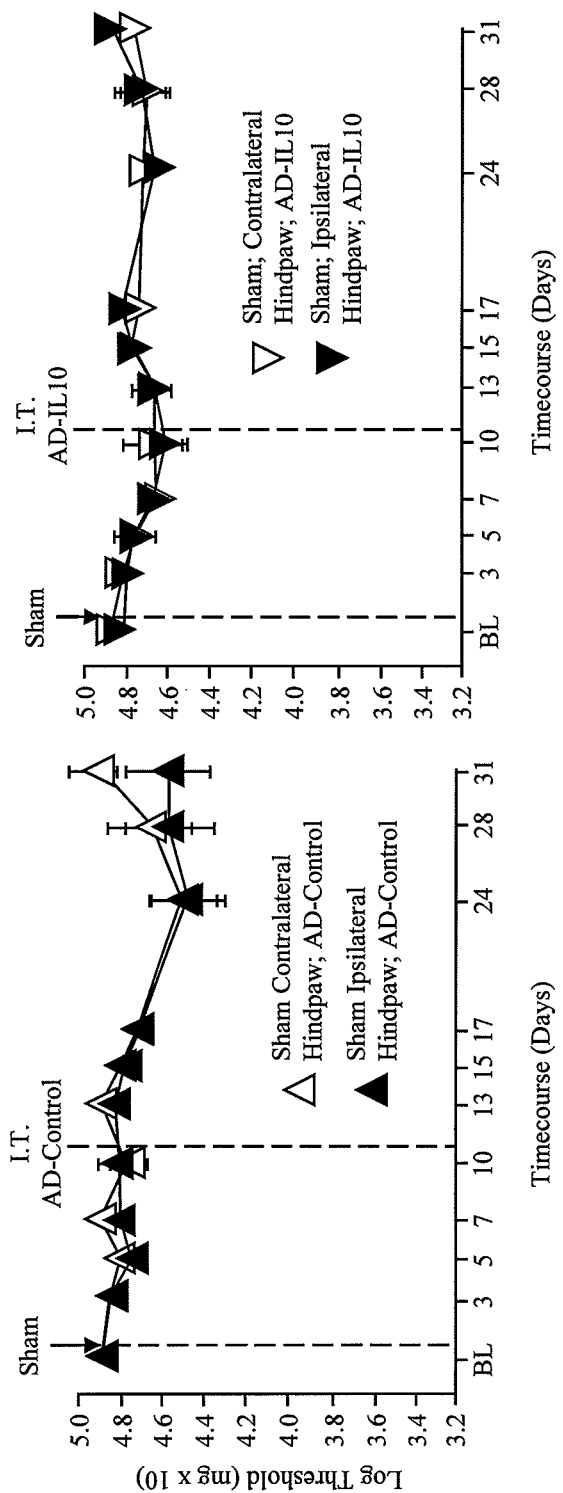
FIG. 7 shows adenoviral IL-10 attenuates sciatic chronic constriction injury (CCI)-induced mechanical allodynias. After predrug (baseline; BL) assessment on the von Frey test, sham (Panels A and B) or CCI (Panels C and D) surgery was performed. Behavioral assessments were recorded on Days 3, 5, 7 and 10 to document the lack of allodynia in sham-operated rats and progressive development of bilateral allodynia in CCI groups. After the Day 10 assessment, rats received intrathecal injections of either AD-Control (Panels A and C) or AD-IL10 (Panels B and D). Behavioral assessments were again recorded on Days 13, 15, 17, 24, 28, and 31; that is, Days 3, 5, 7, 14, 18, and 21 days after AD. While neither AD-Control nor AD-IL10 exerted marked effects in sham-operated animals, AD-IL10 transiently attenuated bilateral CCI allodynia (Panel D) compared to CCI operated AD-Control treated animals (Panel C).
Figures 7C, 7D:
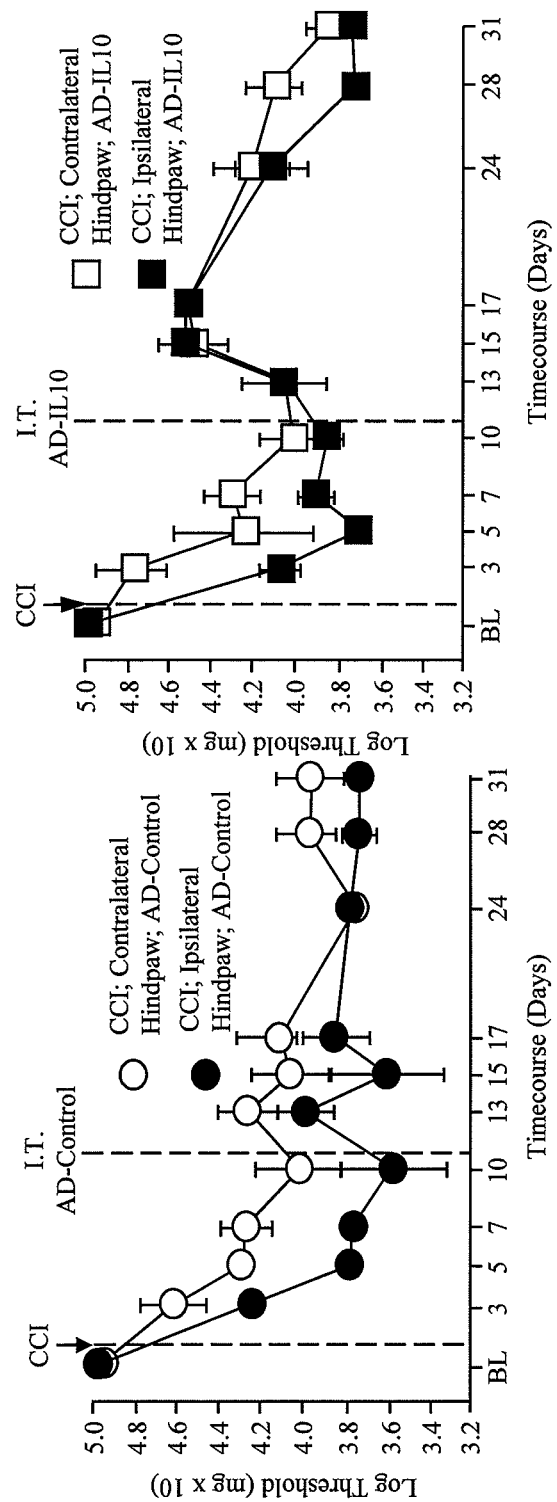
Figures 8A, 8B:
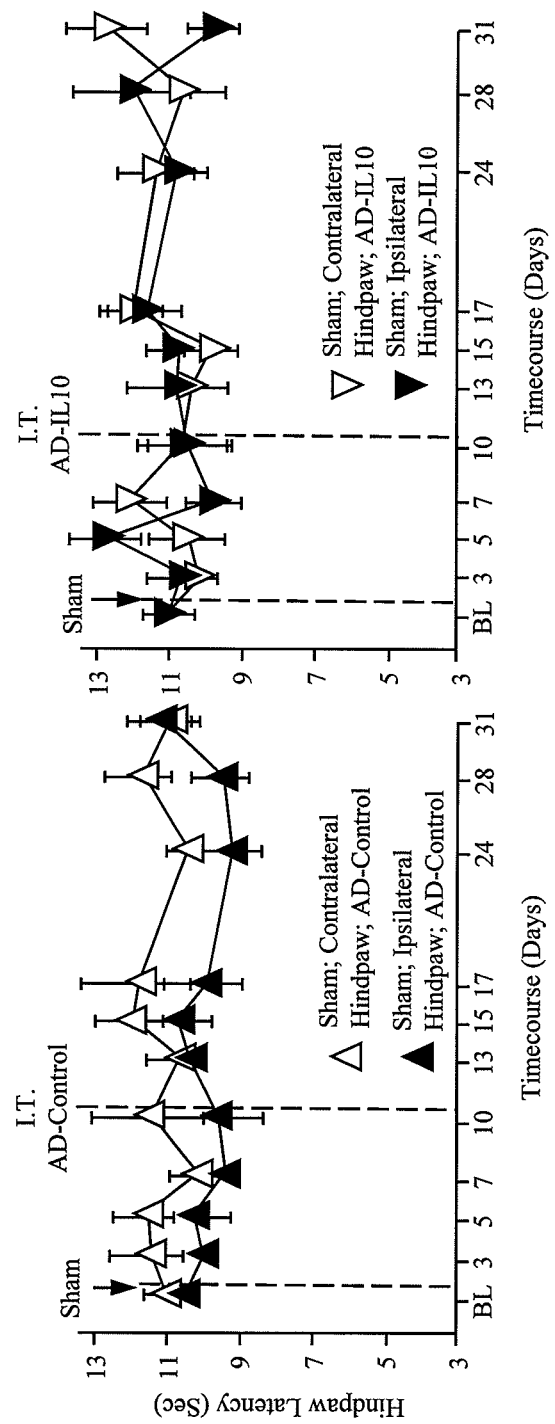
FIG. 8 shows that adenoviral IL-10 attenuates chronic constriction injury (CCI)-induced thermal hyperalgesia. After predrug (baseline; BL) assessment on the Hargreaves test, sham (Panels A and B) or CCI (Panels C and D) surgery was performed. Behavioral assessments were recorded on Days 3, 5, 7 and 10 to document the lack of thermal hyperalgesia in sham operated rats and progressive development of ipsilateral (unilateral) thermal hyperalgesia in CCI groups. After the Day 10 assessment, rats received intrathecal injections of either AD-Control (Panels A and C) or AD-IL10 (Panels B and D). Behavioral assessments were again recorded on Days 13, 15, 17, 24, 28, and 31; that is, Days 3, 5, 7, 14, 18, and 21 days after AD. While neither AD-Control nor AD-ILI0 exerted marked effects in sham operated animals, AD-IL10 transiently attenuated ipsilateral CCI thermal hyperalgesia (Panel D) compared to CCI operated AD-Control treated animals (Panel C).
Figures 8C, 8D:
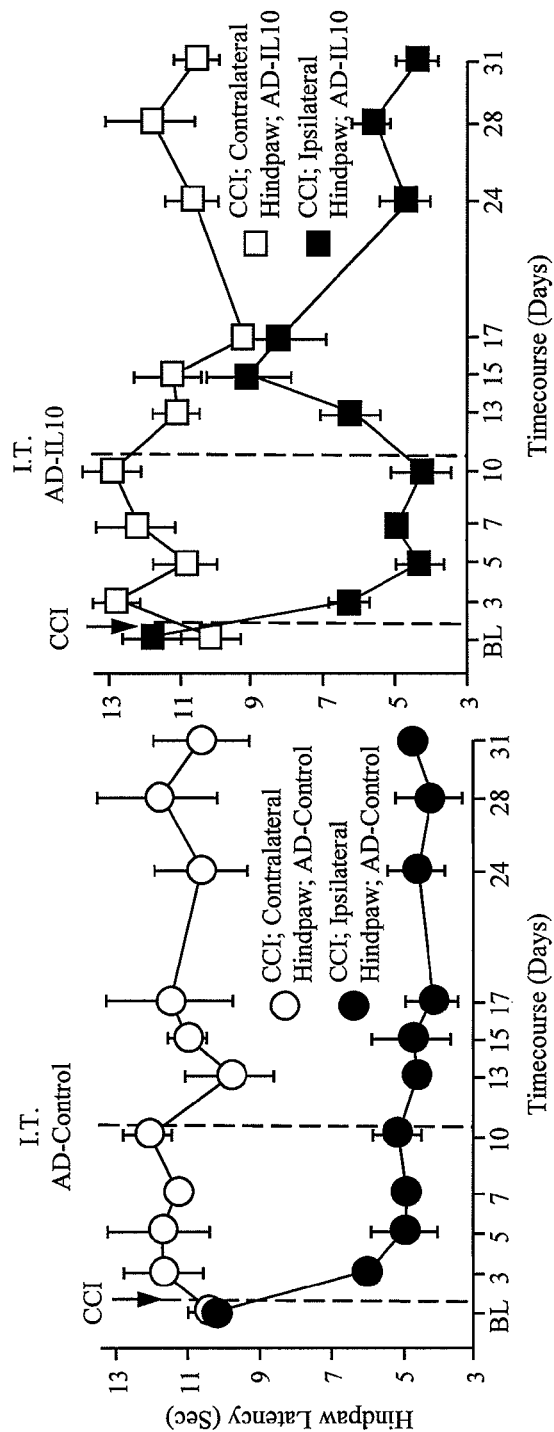

CCI produced chronic bilateral mechanical allodynia (FIG. 7) and chronic ipsilateral thermal hyperalgesia (FIG. 8).

Such a pattern of pain changes is in accord with prior publications (Paulson et al., *Pain* (2000) 84:233-245). For behavioral assessments between Days 3-10, prior to adenoviral administration, ANOVA for the von Frey test revealed reliable main effects of CCI ($F_{1,38}$=143.235, p<0.0001), laterality ($F_{1,38}$=16.797, p<0.001) and time after CCI surgery ($F_{3,114}$=15.699, p<0.0001), and interactions between CCI surgery and laterality ($F_{1,38}$=13.824, p<0.001) and time after CCI surgery and CCI ($F_{3,114}$=7.054, p<0.001). Post hoc means comparison revealed that CCI induced bilateral mechanical allodynia compared to sham operated controls (ipsilateral: p<0.0001; contralateral: p<0.0001). In addition, prior to adenoviral administration, ANOVA for the Hargreaves test revealed reliable main effects of CCI ($F_{1,38}$=239.135, p<0.0001) and laterality ($F_{1,38}$=150.902, p<0.0001), and interactions between CCI and laterality ($F_{1,38}$=103.228, p<0.0001). Post hoc means comparison revealed that CCI induced unilateral thermal hyperalgesia compared to sham operated controls (ipsilateral: p<0.0001; contralateral: p>0.49).

After intrathecal adenoviral administration, AD-IL10 reversed these ongoing pathological pain states. That is, analyzing data between Days 13-24, AD-IL10 reversed both bilateral allodynia and ipsilateral thermal hyperalgesia induced by CCI. ANOVA revealed for the von Frey test reliable main effects of CCI ($F_{1,38}$=105.832, p<0.0001), IL-10 ($F_{1,38}$=8.998, p<0.005), and time ($F_{3,114}$=5.651, p<0.01), and interactions between CCI and IL10 ($F_{1,38}$=14.301, p<0.001), time after intrathecal adenovirus and IL-10 ($F_{3,114}$=7.29, p<0.001) and time after intrathecal adenovirus, CCI and IL-10 ($F_{3,114}$=2.604, p=0.05). Posthoc means comparisons supported that IL-10 reversed the bilateral mechanical allodynic effects of CCI by Day 15 (p<0.0001 and p<0.02, respectively, comparing the ipsilateral and contralateral paw of the AD-ILI0 group vs. AD-Control on Day 15), as well as on day 17 (p<0.0001 and p<0.01, respectively, comparing the ipsilateral and contralateral paw of the AD-ILI0 group vs. AD-Control on Day 17).

ANOVA revealed for the Hargreaves test reliable main effects of CCI ($F_{1,38}$=48.069, p<0.0001), ILI0 ($F_{1,38}$=4.727, p<0.05) and laterality ($F_{1,38}$=48.466, p<0.0001) and interactions between CCI and laterality ($F_{1,38}$=30.955, p<0.0001), ILI0 and laterality ($F_{1,38}$=6.494, p<0.01) and time after intrathecal adenovirus, CCI and ILI0 ($F_{3,114}$=3.116, p<0.05). Posthoc means comparisons supported that ILI0 reversed the ipsilateral thermal hyperalgesic effects of CCI by Day 15 (p<0.002, comparing the ipsilateral paw of the AD-ILI0 group vs. AD-Control on Day 15), as well as on day 17 (p<0.01, comparing the ipsilateral paw of the AD-ILI0 group vs. AD-Control on Day 17).

Intrathecal AD-ILI0 did not permanently reverse these ongoing pathological pain states. This was expected, given that cells infected by adenovirus are readily detected and deleted by the immune system. Indeed, the literature on the adenovirus used in this study supported that it would only temporarily reverse the consequences of a proinflammatory challenge (Gudmundsson et al., *Amer. J. Resp. Cell & Molec. Biol.* (1998) 19:812-818). In support of this, AD-IL10 reversal of CCI-induced pathological pain states began dissipating by Day 24. From Day 24-31, both mechanical allodynia and thermal hyperalgesia progressively returned. By Day 28, mechanical allodynia and thermal hyperalgesia had returned to the preadenoviral levels observed at Day 10. This was supported by ANOVA that mechanical allodynia ($F_{1,38}$=0.450, p>0.50) and thermal hyperalgesia ($F_{1,38}$=0.612, p>0.43) did not differ from those at preadenoviral levels.

The above examples demonstrate that lumbosacral intrathecal delivery of replication-deficient adenovirus containing the cDNA for human IL-10 produces site-specific release of IL-10 into CSF. Neither the presence of $5-10\times10^7$ PFU of adenovirus nor virally driven IL-10 caused observable effects on basal response thresholds to calibrated touch/pressure (von Frey test) or thermal (Hargreaves test) stimuli. However, adenoviral IL10 prevented and reversed pathological pain states. Adenoviral IL-10 prevented mechanical allodynias induced by spinal immune activation with intrathecal HIV-1 gp120 and by sciatic inflammatory neuropathy (SIN). It reversed mechanical allodynias induced by SIN and sciatic traumatic neuropathy (CCI). Lastly, it reversed thermal hyperalgesia induced by CCI. Given that neuropathic pain is especially difficult to treat with currently available drugs {McQuay et al., *Brit. Med. J.* (1995) 311:1047-1052; McQuay et al., *Pain* (1996) 68:217-227; Collins et al., *J. Pain Symptom. Manage.* (2000) 20:339-457, the success of this gene therapy is dramatic.

Example 6

Prevention of Sciatic Inflammatory Neuropathy (SIN) Induced Mechanical Allodynia by Intrathecal AAV-ILI0

Given the profound results achieved with adenoviral-IL10 and in order to test whether the results were achievable with different vectors and molecules, the following experiments were conducted using (a) a different viral vector (AAV) and (b) rat IL-10 instead of human IL-10. The use of rat IL-10 eliminates potential interference from the immune system to the foreign human IL-10 protein when delivered to rats.

The dose of AAV-IL10 chosen for study was based on observations from Example 3 ($5\times10^7$ PFU of adenovirus in 5 μl). Here, it was estimated that $8.5\times10^8$ infectious particles in 5 μl would be efficacious. An equal volume of AAV-Control ($8.5\times10^8$ PFU in 5 μl) was administered to the control group. Rats were assessed for their responses to the von Frey test prior to (BL) intrathecal AAV (either AAV-10 or AAV-Control) was delivered (n=5-6/group). The second BL assessment (BL-2) was conducted 3 days after AAV injection to ensure that this dose of AAV did not alter normal threshold responses. Unilateral and bilateral chronic SIN was created as described previously (Milligan et al., *J. Neurosci.* (2003) 23:1026-1040). Peri-sciatic microinjection of zymosan (either 4 or 160 ug) was delivered immediately after BL-2 (Day 0) and 2, 4, 6 and 8 days later. Von Frey tests were again performed daily until Day 8 and on Day 10. When behavioral testing and peri-sciatic injections occurred on the same day, behavioral testing preceded the peri-sciatic injection.

Figure 9:
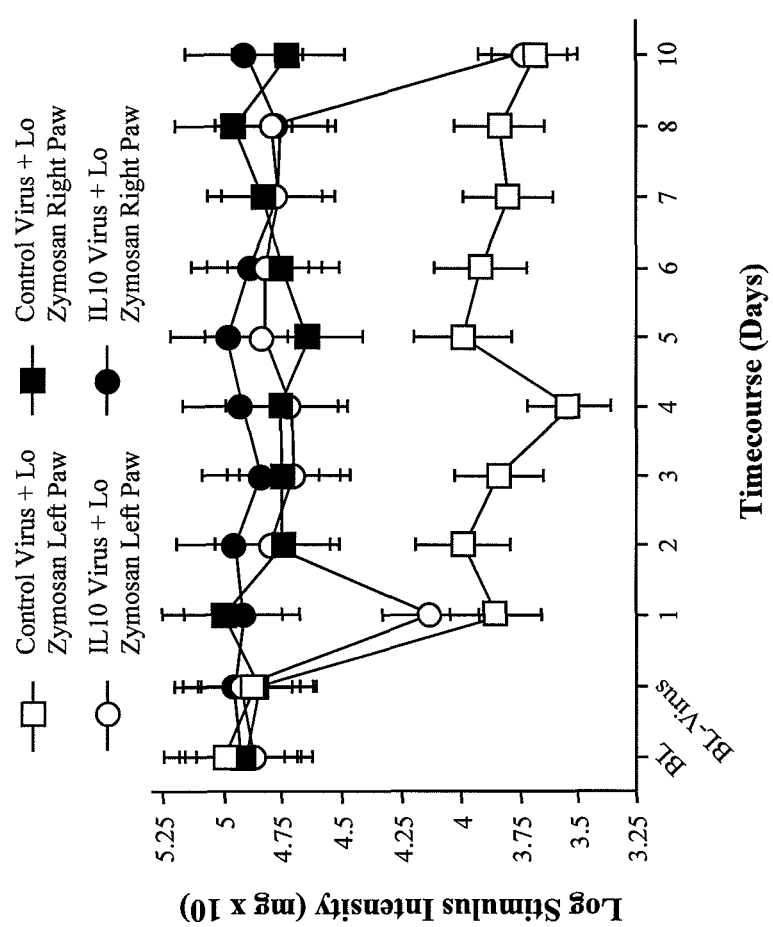
FIG. 9 shows the effect of AAV-delivered IL-10 on chronic SIN-induced allodynia. After baseline (BL) assessment, rats were injected intrathecally with either AAV-Control or AAV-IL10. After allowing the AAV to infect, rats were then chronically injected over the left sciatic nerve with zymosan (yeast cell walls) to create an inflammatory neuropathy. Profound neuropathic pain was demonstrated by SIN in rats receiving intrathecal control virus (open squares). Intrathecal AAV-IL10 blunted this neuropathic pain (open circles). Filled squares and filled circles show normal pain responses of the uninvolved hindleg (right).

As shown in FIG. 9, AAV-delivered IL-10 had no effect on the normal (right) leg pain responses but returned the neuropathic leg (left) to normal levels of pain sensitivity. ANOVA revealed that AAV-IL10 and AAV-Control had no effect on mechanical response thresholds measured 3 days after virus delivery, compared to BL ($F_{1,48}$=1.069, p>0.30). Hence neither the presence of IL-10 or AAV had measurable effects on basal pain responses. Low dose zymosan induced a unilateral allodynia while higher dose zymosan induced a bilateral allodynia, compared to BL measures. Repeated measures ANOVA revealed reliable main effects of peri-sciatic zymosan dose ($F_{2,44}$=237.795, p<0.0001), intrathecal AAV-IL10 ($F_{1,44}$=399.912, p<0.0001), laterality ($F_{1,44}$=125.122, p<0.0001) and time after peri-sciatic zymosan application ($F_{8,352}$=14.865, p<0.0001), and interactions between intrathecal AAV-IL10 and zymosan dose ($F_{2,44}$=125.975, p<0.0001), intrathecal AAV-IL10 and laterality ($F_{1,44}$=24.906, p<0.0001), zymosan dose and laterality ($F_{2,44}$=69.651, p<0.0001), intiathecal AAV-IL10, zymosan dose and laterality ($F_{2,44}$=24.323, p<0.0001) and time after peri-sciatic zymosan application, intrathecal AAV-IL10, zymosan dose and laterality ($F_{16,352}$=1.706, p<0.05).

Example 7

Full Time Course of Reversal of Chronic Constriction Injury (CCI) Induced Mechanical Allodynia and Thermal Hyperalgesia by Intrathecal AAV-IL10

In order to determine whether AAV-mediated IL-10 gene delivery was effective in reversing CCI induced mechanical allodynia and thermal hyperalgesia, the following experiments were conducted. The dose of AAV-IL10 chosen for study was $8.5\times10^8$ infectious particles of AAV in 5 µl. An equal volume of AAV-Control ($8.5\times10^8$ infectious particles in 5 µl) was administered to the control group. Rats were assessed for their responses to the von Frey test and Hargreaves test prior to (BL) and again on Days 3 and 10 after CCI or sham surgery. This latter test allowed verification of the development of chronic mechanical allodynia and thermal hyperalgesia in CCI rats, compared to controls. Immediately after the test on Day 10, all rats received intrathecal AAV-IL10 or AAV-Control (n=6/group). Von Frey and Hargreaves tests were again performed on Days 3, 5, 7, 9, 11, 14, 16 and 20 after viral administration. This corresponds to Days 13, 15, 17, 19, 21, 24, 26, and 30 after CCI or Sham surgery. These tests allowed assessment of (a) the ability of AAV-IL10 to reverse well-established traumatic neuropathy pain and (b) the duration of AAV-IL10 effectiveness.

Figure 10:
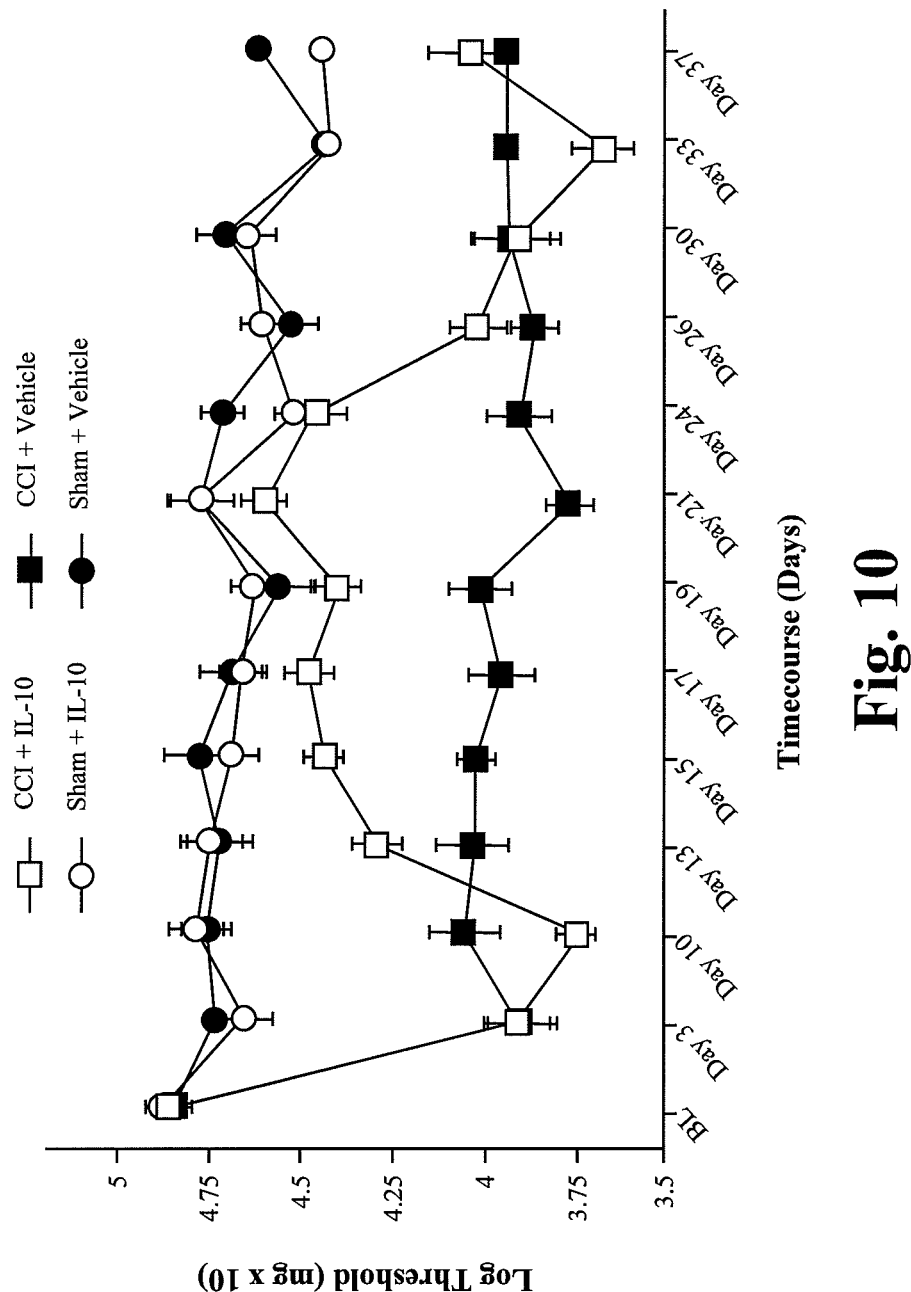
FIG. 10 shows the effect of AAV-delivered IL-10 on mechanical allodynia induced by CCI. After baseline (BL) assessment, rats were given either sham surgery or CCI of the left sciatic nerve to induce traumatic neuropathy. After behavioral assessment on Day 10, rats were injected intrathecally with either AAV-Control or AAV-IL10. Profound neuropathic pain was demonstrated by CCI in rats receiving intrathecal control virus (filled squares). Intrathecal AAV-IL10 blunted this neuropathic pain (open squares). Filled circles and open circles show normal pain responses of sham operated rats administered either AAV-Control or AAV-IL10.
Figure 11:
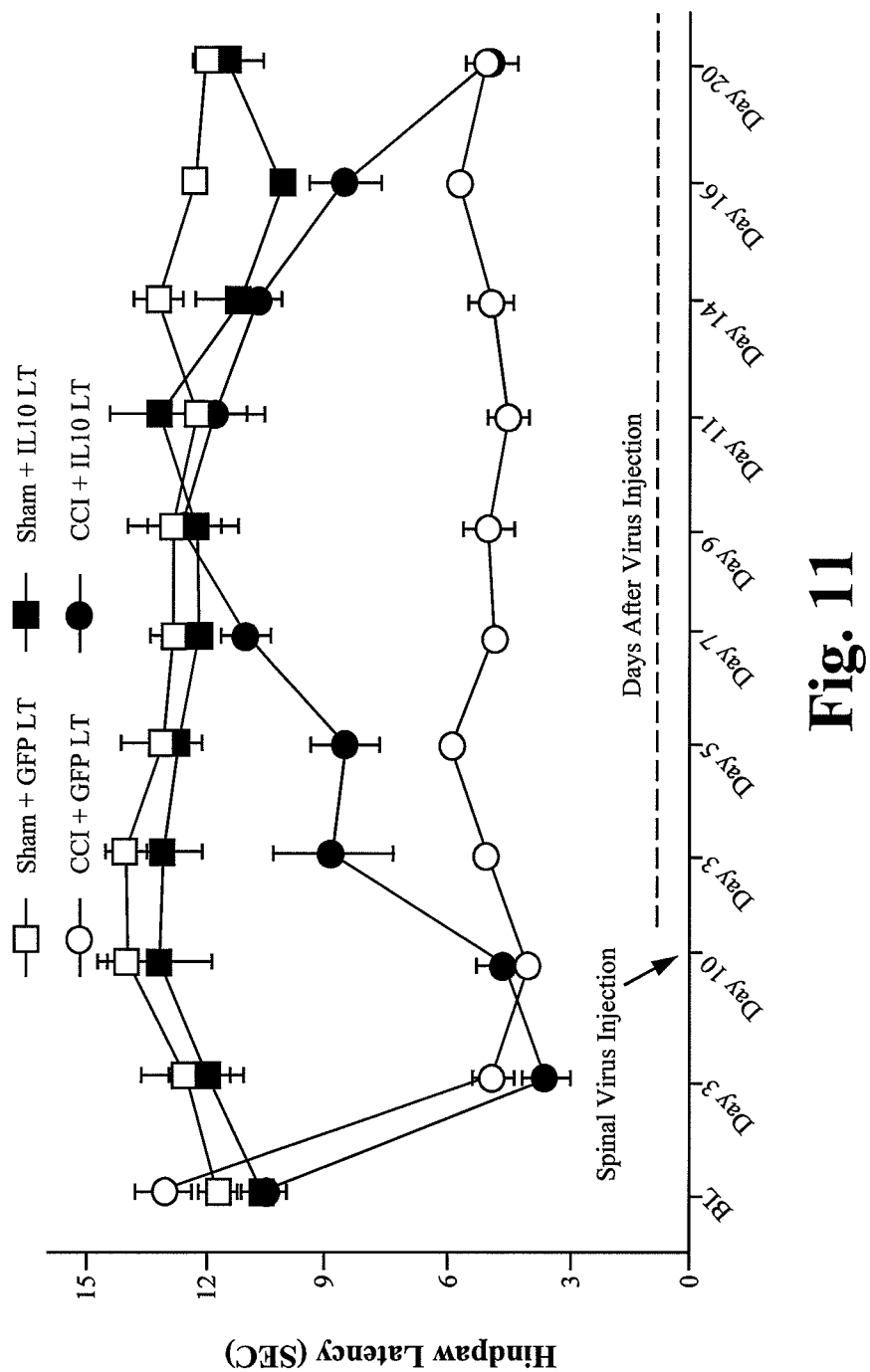
FIG. 11 shows the effect of AAV-delivered IL-10 on chronic thermal hyperalgesia induced by CCI. After baseline (BL) assessment, rats were given either sham surgery or CCI of the left sciatic nerve to induce traumatic neuropathy. After behavioral assessment on Day 10, rats were injected intrathecally with either AAV-Control or AAV-IL10. Profound neuropathic pain was demonstrated by CCI in rats receiving intrathecal control virus (open circles). Intrathecal AAV-IL10 blunted this neuropathic pain (filled circles). Filled squares and open squares show normal pain responses of sham operated rats administered either AAV-Control or AAV-IL10.

As shown in FIGS. 10 and 11, AAV-IL10 had no effect on the sham operated rats but returned the neuropathic pain back to normal levels of pain sensitivity. Prior to CCI surgery, all groups showed similar BL values ($F_{7,40}$=0.345, p>0.9). As observed in the experiments above, CCI produced chronic bilateral mechanical allodynia and chronic ipsilateral thermal hyperalgesia. For behavioral assessments at Days 3 and 10, prior to AAV intrathecal administration, ANOVA for the von Frey test revealed reliable main effects of CCI ($F_{1,40}$=197.446, p<0.0001) and laterality ($F_{1,40}$=6.356, p<0.05).

In addition, prior to CCI surgery, all groups showed no behavioral BL differences for the Hargreaves test ($F_{7,40}$=2.102, p>0.05). Before AAV intrathecal administration, ANOVA for the Hargreaves test revealed reliable main effects of CCI ($F_{1,40}$=140.740, p<0.0001) and laterality ($F_{1,38}$=48.901, p<0.0001), and an interaction between CCI and laterality ($F_{1,40}$=104.295, p<0.0001).

After intrathecal AAV administration, AAV-IL10 reversed these ongoing pathological pain states. That is, analyzing data between Days 13-30 (corresponding to days 3-20), AAV-IL10 reversed both bilateral allodynia and ipsilateral thermal hyperalgesia induced by CCI. ANOVA revealed for the von Frey test reliable main effects of CCI ($F_{1,40}$=496.336, p<0.0001), AAV-IL10 ($F_{1,40}$=59.636, p<0.0001), laterality ($F_{1,40}$=28.565, p<0.0001), and time after AAV ($F_{7,280}$=10.462, p<0.0001), and interactions between CCI and AAV-IL10 ($F_{1,40}$=72.988, p<0.0001), CCI and laterality ($F_{1,40}$=9.325, p<0.01), time after AAV and CCI ($F_{7,280}$=5.823, p<0.0001), time after AAV and AAV-IL10 ($F_{7,280}$=5.993, p<0.0001) and time after AAV, CCI and AAV-IL10 ($F_{7,280}$=4.840, p=0.0001).

ANOVA revealed for the Hargreaves test reliable main effects of CCI ($F_{1,39}$=134.036, p<0.0001), AAV-IL10 ($F_{1,39}$=12.047, p<0.01) and laterality ($F_{1,39}$=66.284, p<0.0001) and time after intrathecal AAV administration ($F_{7,273}$=12.237, p<0.005), and interactions between CCI and AAV-IL10 ($F_{1,39}$=24.486, p<0.0001), CCI and laterality ($F_{1,39}$=91.956, p<0.0001), IL-10 and laterality ($F_{1,39}$=17.392, p<0.0001) CCI, AAV-IL10 and laterality ($F_{1,39}$=35.721, p<0.0001) and time after intrathecal AAV administration and IL10 ($F_{7,273}$=3.783, p<0.005).

Example 8

Partial Time Course of Reversal of Chronic Constriction Injury (CCI) Induced Mechanical Allodynia and Thermal Hyperalgesia by Intrathecal AAV-IL10 to Collect CSF and Tissue Samples at Time of Full Reversal Example 7 was repeated with one exception. That is, the time course of intrathecal AAV-IL10 was truncated at the time of full behavioral reversal of both thermal hyperalgesia and low threshold allodynia to examine the mechanism of action of spinal AAV-IL10. The dose of AAV-IL10 was $8.5\times10^8$ infectious particles of AAV in 5 µl. An equal volume of AAV-Control ($8.5\times10^8$ infectious particles in 5 µl) was administered to the control group. Rats were assessed for their responses to the von Frey test and Hargreaves test prior to (BL) and again on Days 3, 5, 7 and 10 after CCI or sham surgery. Immediately after the test on Day 10, all rats received intrathecal AAV-IL10 or AAV-Control (n=6/group). Von Frey and Hargreaves tests were again performed on Days 3, 5 and 7 after viral administration. This corresponds to Days 13, 15 and 17 after CCI or Sham surgery. These tests allowed assessment of (a) the production and release of AAV-IL10 compared to control-AAV (b) the action AAV-IL10 on proinflammatory cytokines (IL-1, TNF-b and IL-6) and their respective receptors as well as IL10 receptors.

Figure 12A:
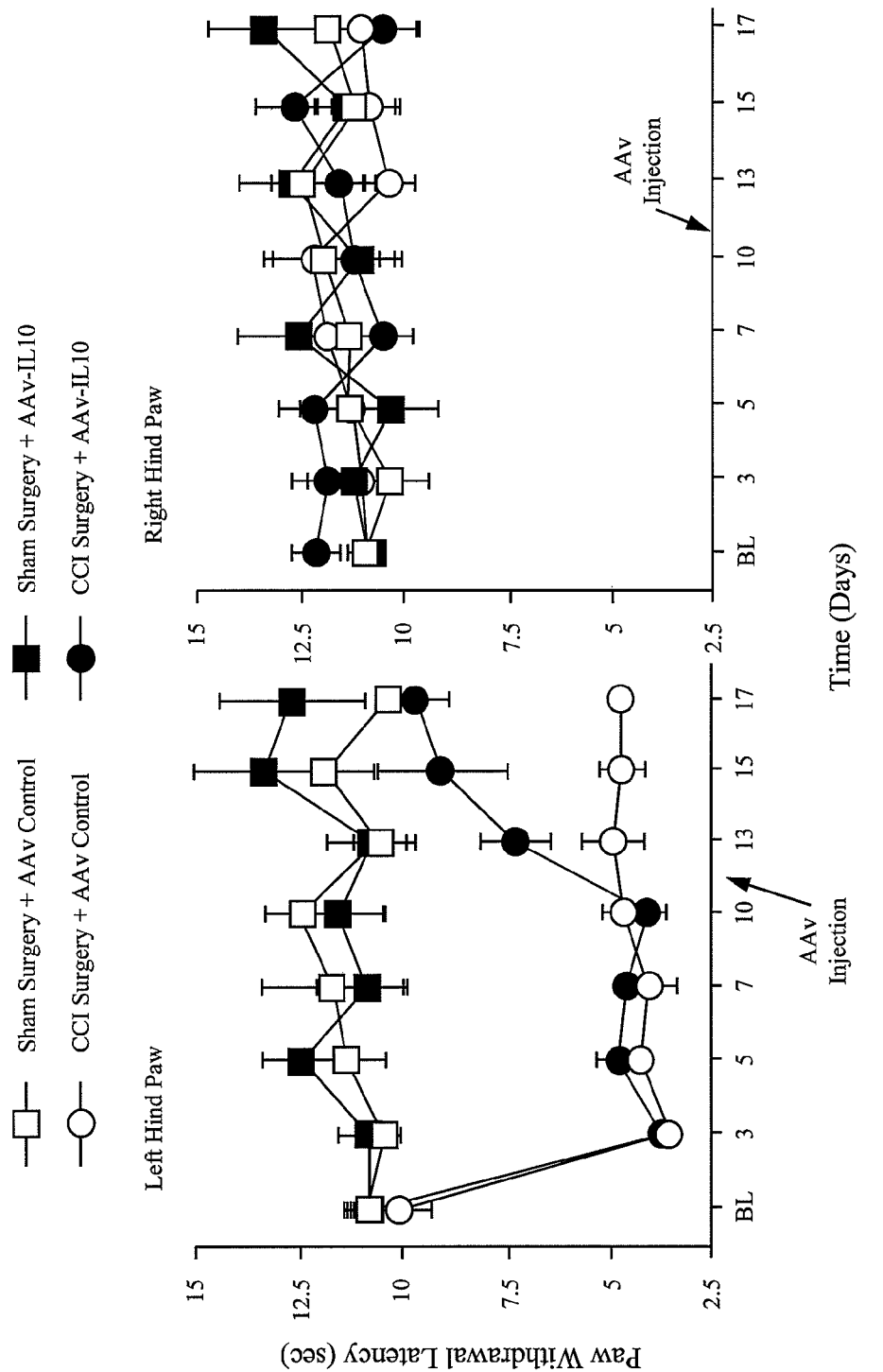
FIGS. 12A and 12B show the effects of AAV-IL10 on chronic thermal hyperalgesia induced by CCI (FIG. 12A) and chronic mechanical allodynia induced by CCI (FIG. 12B). These were partial timecourses as the experiments were stopped at the point of complete pain reversal so that tissues could be collected for analyses. After baseline (BL) assessments, rats were given either sham surgery or CCI of the left sciatic nerve to induce traumatic neuropathy. After behavioral assessment on Day 10, rats were injected intrathecally with either AAV-Control or AAV-IL10. Behavior was reassessed 3, 5 and 7 days later (corresponding to Days 13, 15 and 17 after CCI or sham surgery). Profound neuropathic pain was demonstrated in CCI rats receiving intrathecal control virus. Intrathecal AAV-IL10 blunted this neuropathic pain. Normal pain responses were observed for sham operated rats administered either AAV-Control or AAV-IL10.
Figure 12B:
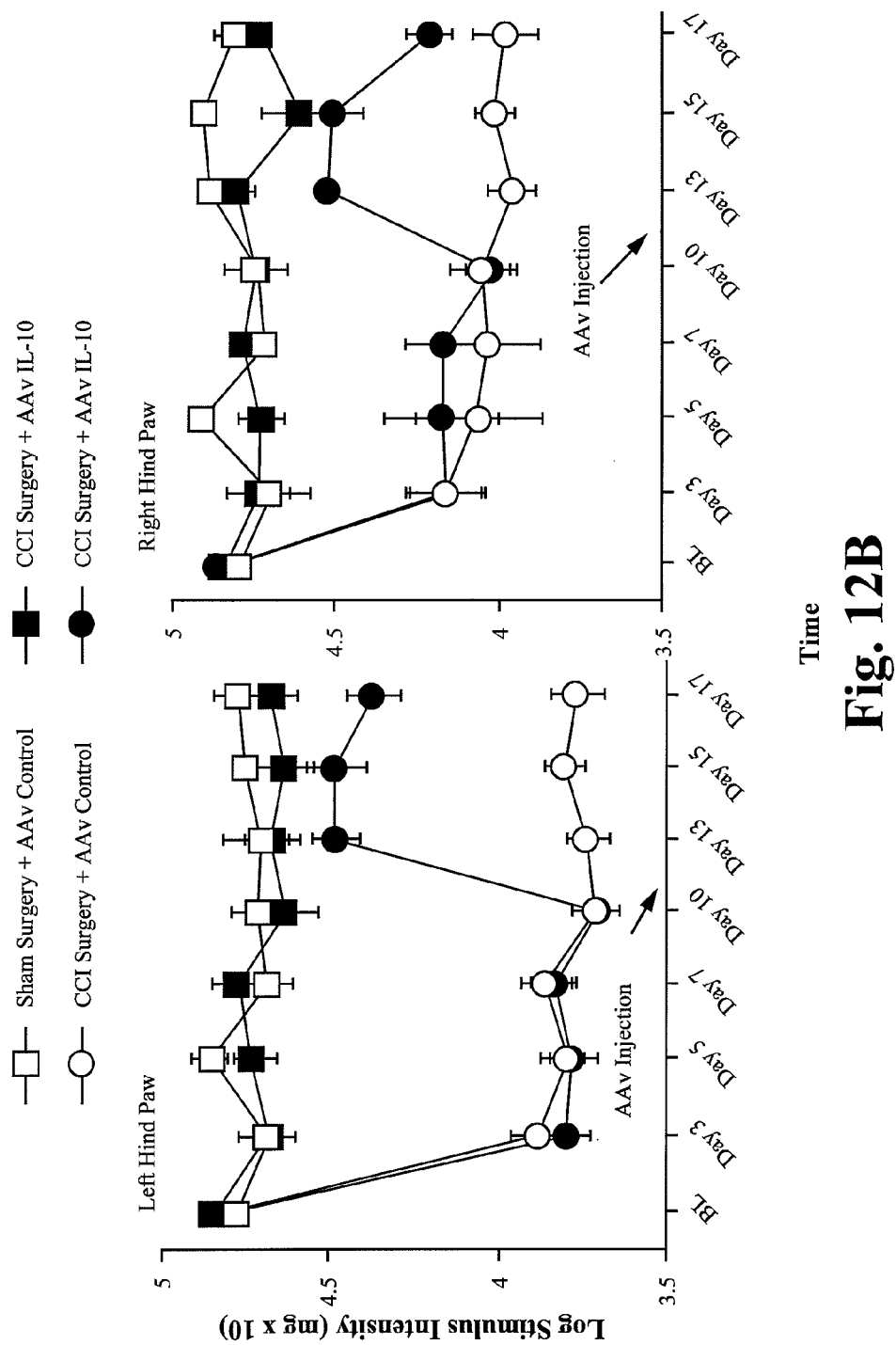

As seen in FIGS. 12A and 12B, AAV-delivered IL-10 again reversed chronic thermal hyperalgesia induced by CCI. This is a partial timecourse as the experiment was stopped at the point of complete pain reversal so that tissues could be collected for analyses. After baseline (BL) assessment, rats were given either sham surgery or CCI of the left sciatic nerve to induce traumatic neuropathy. After behavioral assessment on Day 10, rats were injected intrathecally with either AAV-Control or AAV-IL10. Behavior was reassessed 3, 5 and 7 days later (corresponding to Days 13, 15 and 17 after CCI or sham surgery). After testing on Day 17, the animals were sacrificed and tissues collected for analyses. Profound neuropathic pain was demonstrated in CCI rats receiving intrathecal control virus. Intrathecal AAV-IL10 blunted this neuropathic pain. Normal pain responses were observed for sham operated rats administered either AAV-Control or AAV-IL10.

In particular, prior to induction of CCI, all groups revealed similar BL values ($F_{7,42}$=0.497, p>0.80). For behavioral assessments between Days 3-10, after induction of CCI and prior to AAV administration, ANOVA for the von Frey test revealed reliable main effects of CCI ($F_{1,42}$=282.369, p<0.0001), laterality ($F_{1,42}$=13.119, p<0.001) and an interaction between CCI surgery and laterality ($F_{1,42}$=8.076, p<0.01).

Prior to the induction of CCI, BL values assessed from the Hargreaves test revealed no differences ($F_{7,42}$=0.957, p>0.47). However, after induction of CCI and prior to AAV administration, ANOVA for the Hargreaves test revealed reliable main effects of CCI ($F_{1,42}$=137.312, p<0.0001) and laterality ($F_{1,42}$=40.480, p<0.0001), and an interaction between CCI and laterality ($F_{1,42}$=156.562, p<0.0001).

After intrathecal AAV administration, AAV-IL10 reversed these ongoing pathological pain states. That is, analyzing data between Days 13-17, AAV-IL10 reversed both bilateral allodynia and ipsilateral thermal hyperalgesia induced by CCI. ANOVA revealed for the von Frey test reliable main effects of CCI ($F_{1,42}$=220.489, p<0.0001), AAV-IL10 ($F_{1,42}$=38.931, p<0.0001), laterality ($F_{1,42}$=86.812, p<0.0001). ANOVA revealed for the Hargreaves test reliable main effects of CCI ($F_{1,42}$=43.169, p<0.0001), AAV-IL10 ($F_{1,42}$=14.740, p<0.001) and laterality ($F_{1,42}$=31.609, p<0.0001) and interactions between CCI and laterality ($F_{1,42}$=18.402, p<0.0001) and AAV-IL10 and laterality ($F_{1,42}$=6.494, p<0.01) and time after intrathecal adeno-associated virus, CCI and IL10 ($F_{3,114}$=5.534, p<0.05).

Example 9

Reversal of Chronic Constriction Injury (CCI) Neuropathic Pain with Intrathecally Injected Plasmid DNA Encoding for IL-I0

Figure 13:
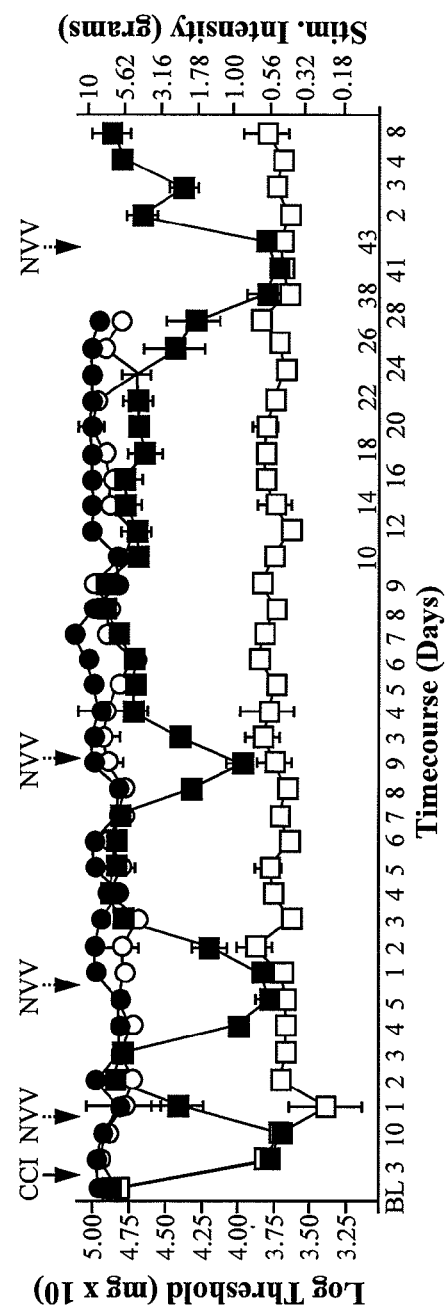
FIG. 13 shows that non-viral vector (NVV) plasmid DNA-driven IL-10 completely reverses CCI induced mechanical allodynia and that repeated intrathecal administration of plasmid IL-10 induces progressively longer pain-relieving effects. After baseline (BL), CCI was induced and rats were given intrathecal injections of either plasmid IL-10 or plasmid GFP as a control at the time-points indicated in the figure by arrows. Filled squares indicate CCI rats administered plasmid IL-10; open squares indicate CCI rats administered the GFP control plasmid; filled circles indicate sham operated rats given plasmid IL-10; open circles indicate sham operated rats administered GFP control plasmid.

In order to determine whether the effect of IL-10 could be elicited by delivery using a non-viral vector (NVV), the following experiment was conducted. 100 µg of plasmid ("naked") DNA (pDNA) encoding either rat IL-10 or GFP (as a control) was injected intrathecally 10 days, 15 days (five days after the first injection), 24 days (nine days after the second injection) and 67 days (43 days after the third injection) later. As shown in FIG. 13, the first injection completely but only briefly reversed pathological pain in the rats. The second injection, given after return to baseline, again completely reversed pain, but for a longer time. The third injection, given after return to baseline, again completely reversed pain but for an even longer time period. Remarkably, the fourth injection, given after the allodynia was fully reestablished for six days (Days 38-43 in FIG. 13), again completely reversed pain. The control plasmid had no effect in the CCI or sham operated rats. These results are remarkable. To the best of the inventors' knowledge, no published report has examined repeated plasmid injections at such short time intervals. Moreover, given that equal doses of the control GFP plasmid had no effect on CCI, the results appear specific for IL-10.

Figure 24:
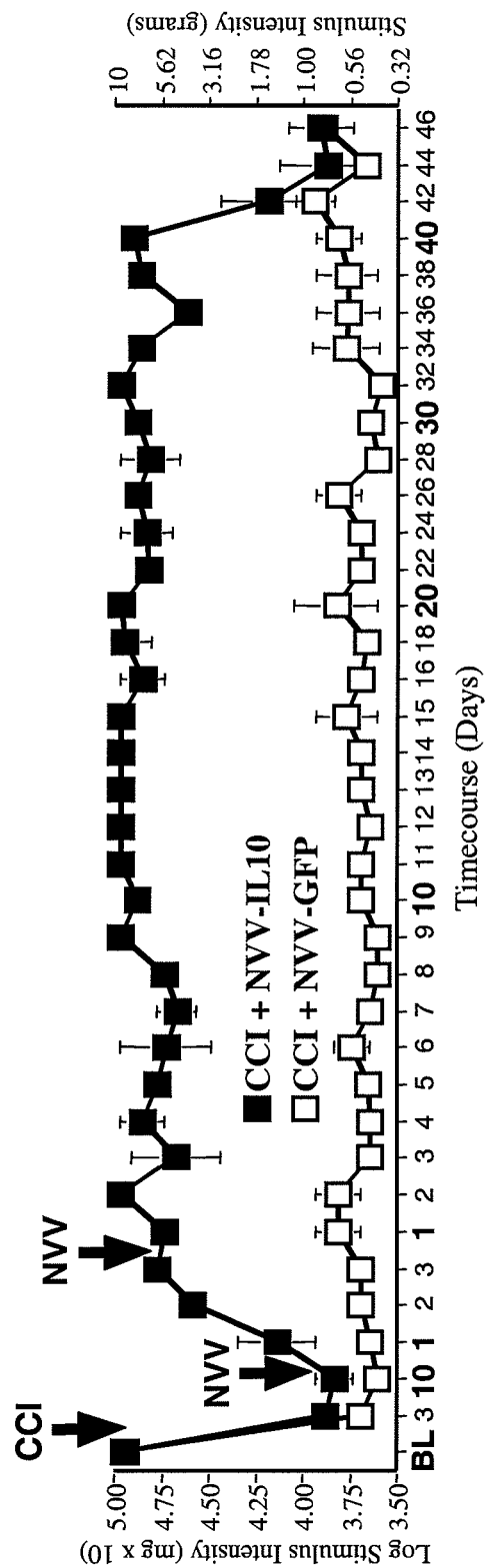
FIG. 24 shows that two doses of non-viral vector (NVV) plasmid DNA-driven IL-10 delivery three days apart induces prolonged attenuation of CCI induced mechanical allodynia. Plasmid IL-10 was injected intrathecally at Day 10 after CCI and three days later. Filled squares indicate the results using plasmid IL-10 while open squares show the results of control plasmid.

These data raised the question of what might happen if the inter-injection interval for successive plasmid administrations were further shortened. Therefore, 100 µg of pDNA encoding rat IL-10 was injected intrathecally 10 days after CCI induced mechanical allodynia (Day 10). This induced fill reversal of allodynia by Day 12 (FIG. 24). A second intrathecal injection of 100 µg of the plasmid was given on Day 13, while CCI pain-enhancement remained fully reversed, as opposed to the experiment shown in FIG. 13 and described above where the second plasmid injection was given after allodynia was allowed to reoccur. As shown in FIG. 24, when the second plasmid injection was delivered while CCI pain-enhancement remained fully reversed, the effectiveness of the second injection was remarkably enhanced.

Figure 25:
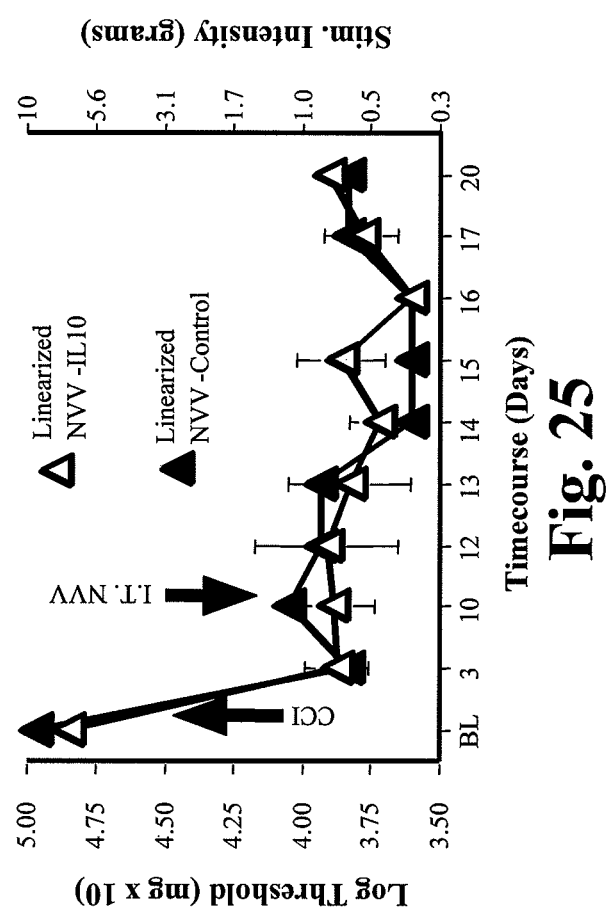
FIG. 25 shows that when the IL-10 plasmid from the experiment described in FIG. 25 is linearized, it is no longer effective in attenuating CCI induced mechanical allodynia.

As a further control, the IL-10 and GFP control plasmids were enzymatically cut to linearize them. Linearized plasmids are known to be far more susceptible to enzymatic degradation and show little to no activity. As expected, an equal dose of linearized plasmid had no effect on CCI (FIG. 25).

Example 10

Effects of AD-IL10 on Morphine Analgesia, Morphine Tolerance and Exaggerated Pain Accompanying Cessation of Chronic Opiates Morphine tolerance and pathological pain have many features in common, leading to the concept that both have common biological underpinnings. Thus, the ability of gene therapy to induce an anti-inflammatory cytokine might impact this phenomenon as well. Rats were injected intrathecally with either AD-IL10 or AD-Control at 5 days prior to the beginning of morphine challenge. They were behaviorally tested prior to and after intrathecal morphine (10 µg) vs. saline across days. On days 1, 3 and 5, the rats were tested for tactile sensitivity (von Frey test) and thermal pain sensitivity (Tail flick test). After morphine, testing followed a 6 hr timecourse.

Figure 14:
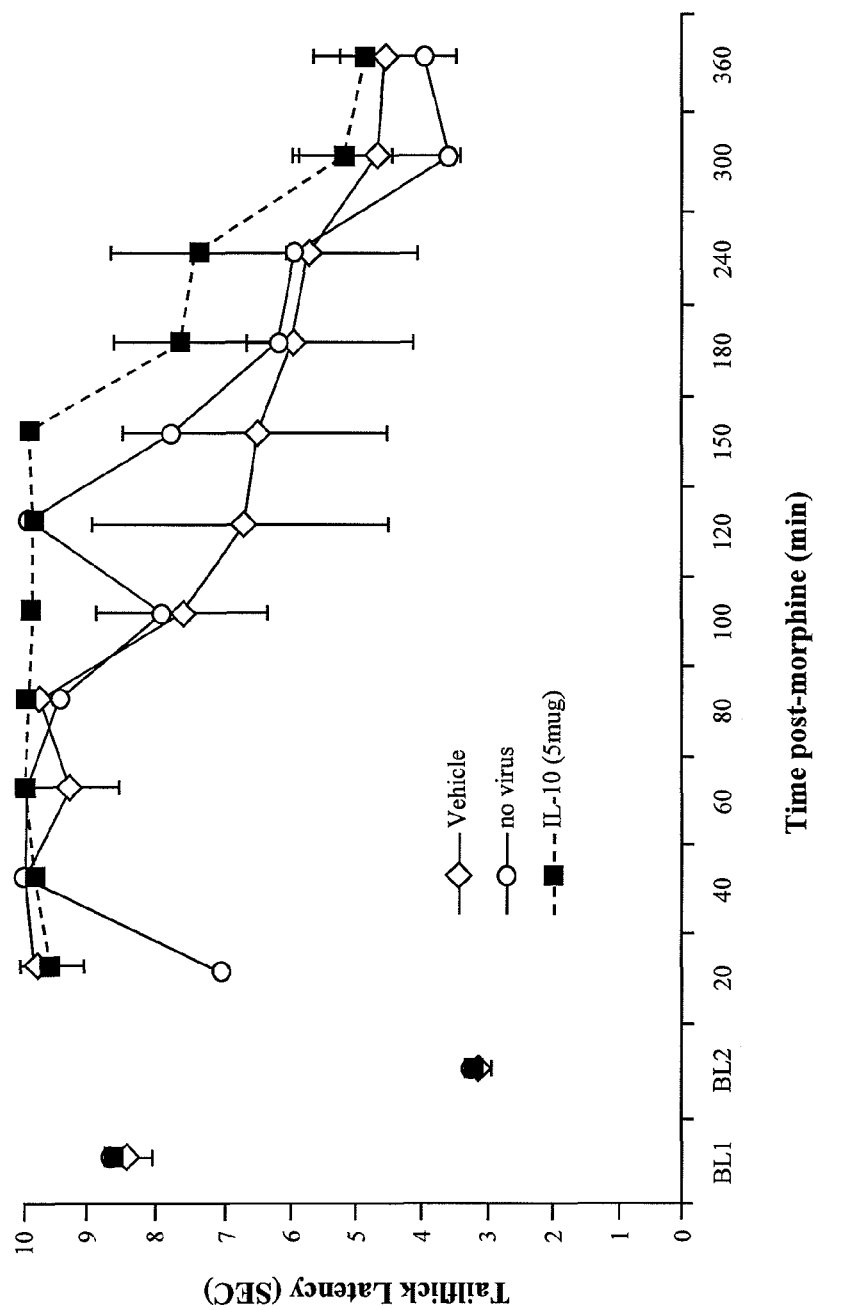
FIG. 14 shows that AD-IL10 potentiates the analgesic effects of acute morphine. To test whether IL-10 would affect the pain-relieving effects of opiates such as morphine, rats were pretreated 5 days prior to morphine with either AD-Control (open diamonds) or AD-IL10 (filled square). A single animal received no virus. As can be seen, rats expressing AD-IL10 (filled squares) showed a more prolonged analgesia than rats with AD-Control (diamonds).

As seen in FIG. 14, IL-10 expression in spinal cord caused even the first dose of morphine to have a more prolonged analgesic (i.e., pain suppressive) effect as IL-10-expressing rats had longer tailflick latencies than did controls 100-240 min later.

Figure 15:
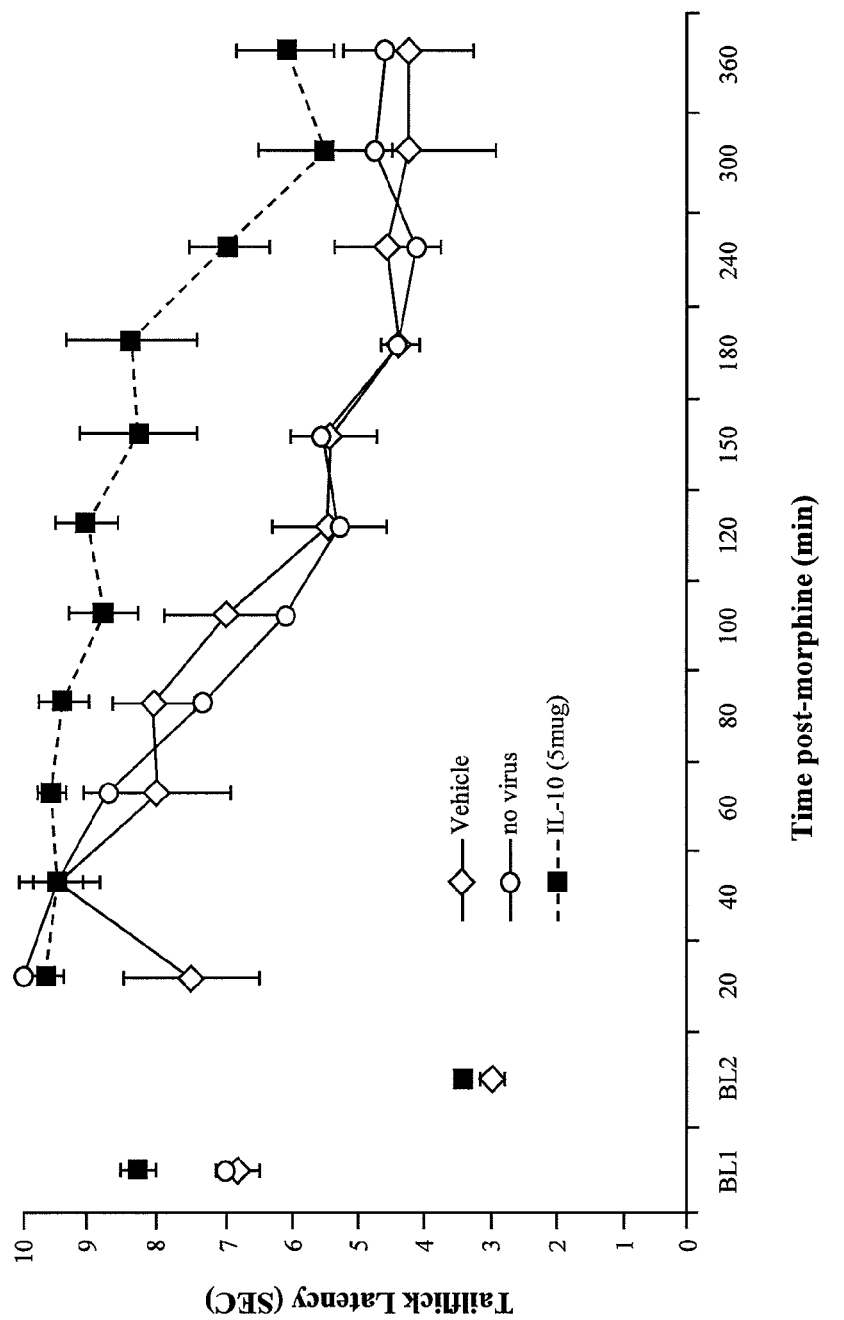
FIG. 15 shows that AD-IL10 delays development of morphine tolerance. Rats were given 10 µg intrathecal morphine daily. Even by the third day of morphine administration, it was obvious that AD-IL10 was delaying the development of morphine tolerance.
Figure 16:
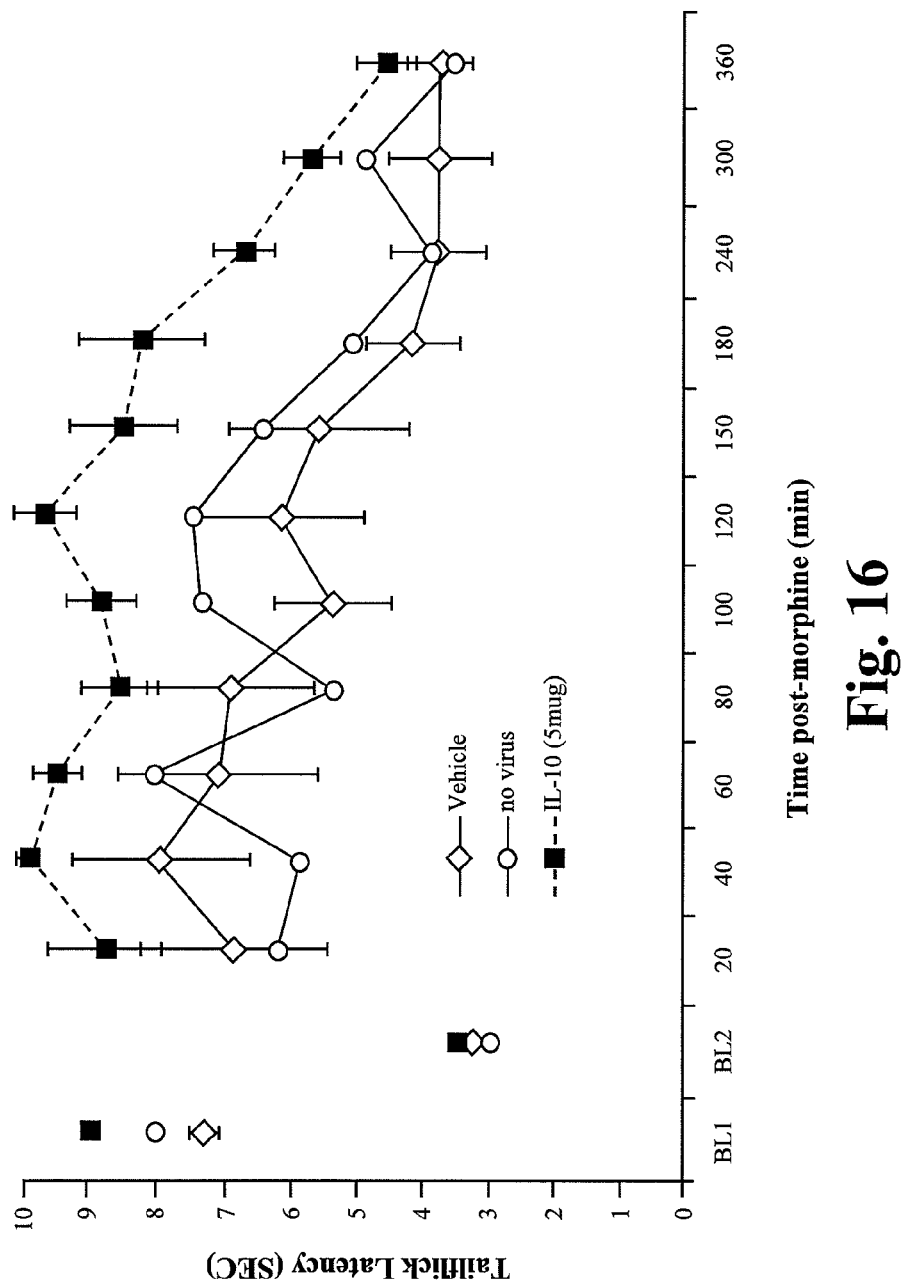
FIG. 16 shows that AD-IL10 delays development of morphine tolerance. Rats were given 10 µg intrathecal morphine daily. Again, on the fifth day of morphine administration, it was obvious that AD-IL10 was delaying the development of morphine tolerance.

As seen in FIGS. 15 and 16, IL-10 expression in spinal cord caused a delay in the development of morphine tolerance as IL-10-expressing rats showed greater morphine analgesia than did control rats.

Figure 17:
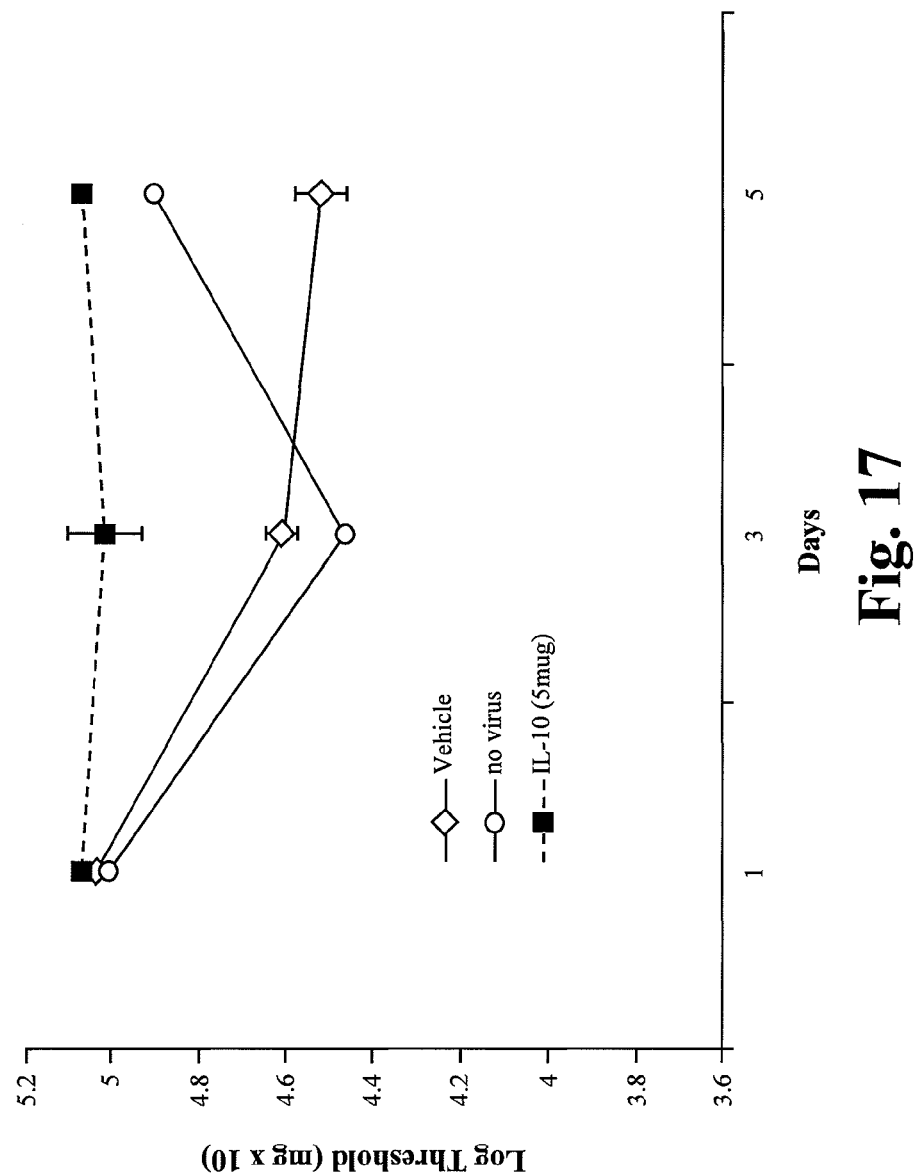
FIG. 17 shows that AD-IL10 prevents exaggerated pain which develops as a consequence of repeated opiate administration. Prior to morphine (day 1), all rats responded normally to the von Frey test for mechanical pain sensitivity. Afterwards, rats got 10 µg intrathecal morphine daily. 24 hr after the last dose of morphine, increased sensitivity (i.e. pain facilitation) was seen in rats receiving AD-Control (open diamond). AD-IL10 (filled squares) completely prevented the exaggerated pain responses created by chronic morphine.

As seen in FIG. 17, repeated morphine administration caused a decrease in pain threshold (increased in pain responsivity) in animals administered AD-Control (labeled Vehicle on the figure). This is a classic effect of chronic morphine, wherein abstinence from the opiate causes exaggerated pain responses. Here, it was recorded immediately prior to the daily dose of morphine, thus 24 hr after the last dose of morphine. AD-IL10 prevented this increase in pain sensitivity.

Example 11

Effects of IL-1ra on Morphine Analgesia, Morphine Tolerance and Exaggerated Pain Accompanying Cessation of Chronic Opiates A. To test for generality, the ability of an antagonist of proinflammatory cytokines to exert parallel effects as IL-10 was tested. Antagonists of proinflammatory cytokines are known to block and reverse various pathological pain states. Here, rats were injected intrathecally with either IL-1ra (interleukin-1 receptor antagonist) or vehicle daily, along with daily morphine or vehicle. They were behaviorally tested prior to and after these daily intrathecal injections. On days 1, 3 and 5, the rats were tested for tactile sensitivity (von Frey test) and thermal pain sensitivity (Tail flick test). After morphine, testing followed a 6 hr timecourse.

Figure 18:
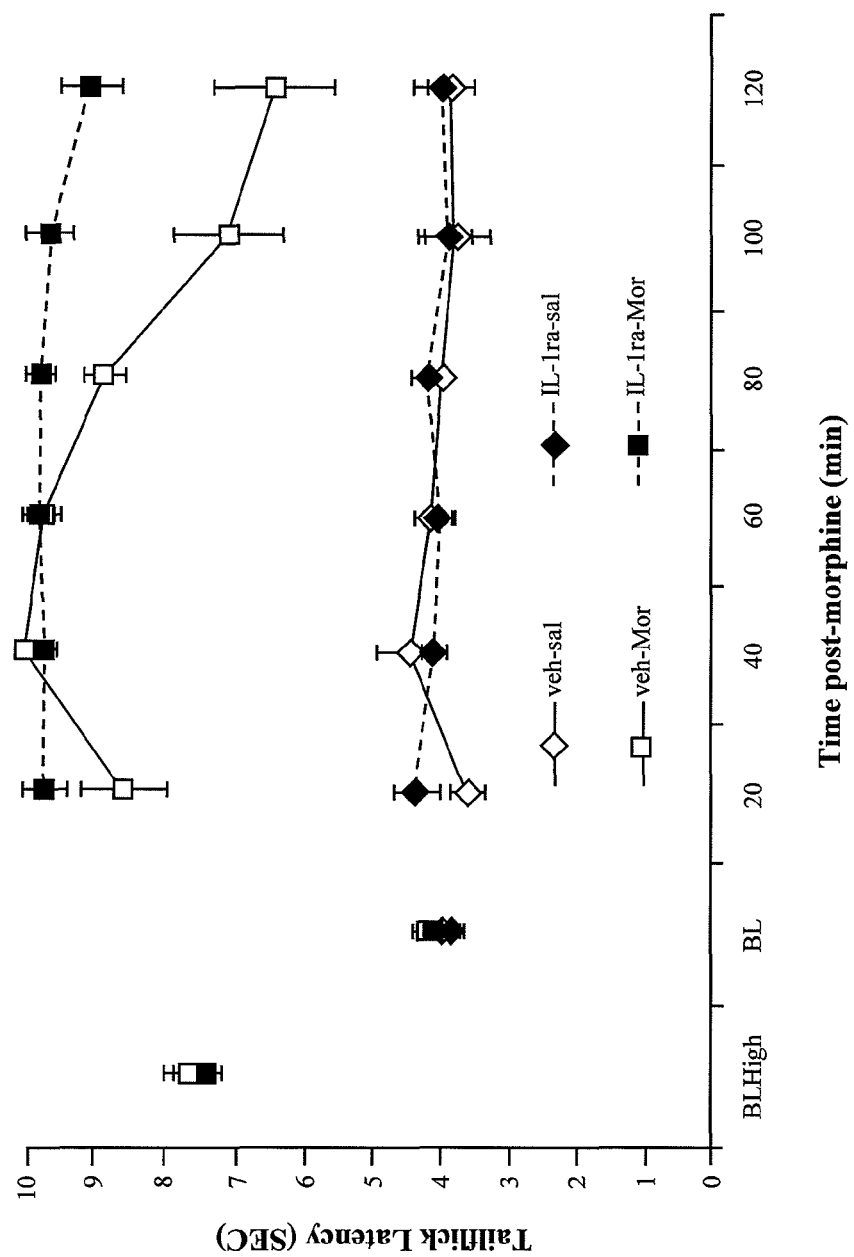
FIG. 18 shows the results of interleukin-1 receptor antagonist (IL-1ra) on morphine analgesia in rats. To test for generality of the concept, repeated injections of an endogenous proinflammatory cytokine antagonist, IL-1ra, were used instead of gene delivery of IL-10. A single injection of IL1ra, which blocks proinflammatory cytokine function, potentiated the analgesic effect of morphine (filled squares) compared to vehicle+morphine (open squares).

As seen in FIG. 18, IL-1ra injected into the cerebrospinal fluid surrounding spinal cord caused even the first dose of morphine to have a more prolonged analgesic (i.e., pain suppressive) effect as IL-1ra-injected rats had longer tailflick latencies than did controls 100-240 min later. Hence, effects on morphine and pain were again parallel.

Figure 19:
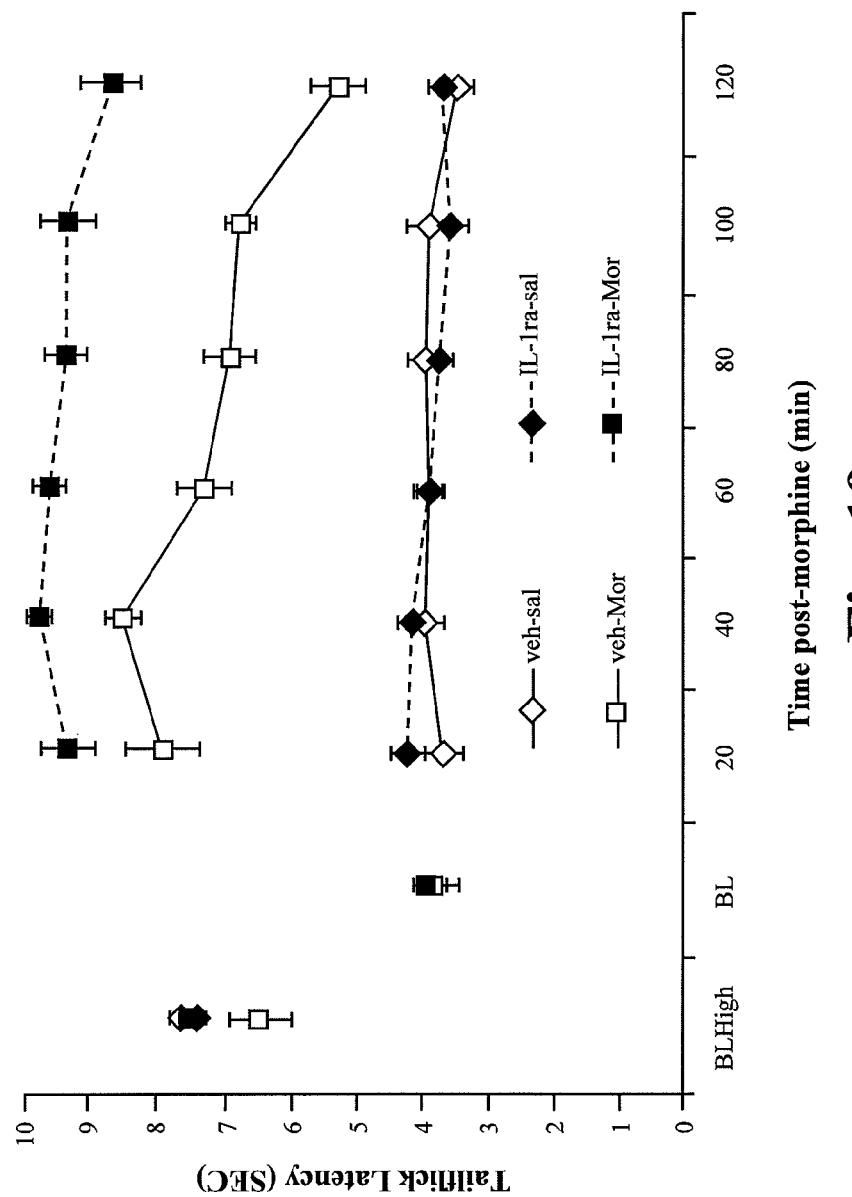
FIG. 19 shows the results of IL-1ra on the development of morphine tolerance. IL-1ra injected daily along with daily morphine injections (filled squares) delayed the development of morphine tolerance compared to rats receiving daily vehicle+morphine (open squares).
Figure 20:
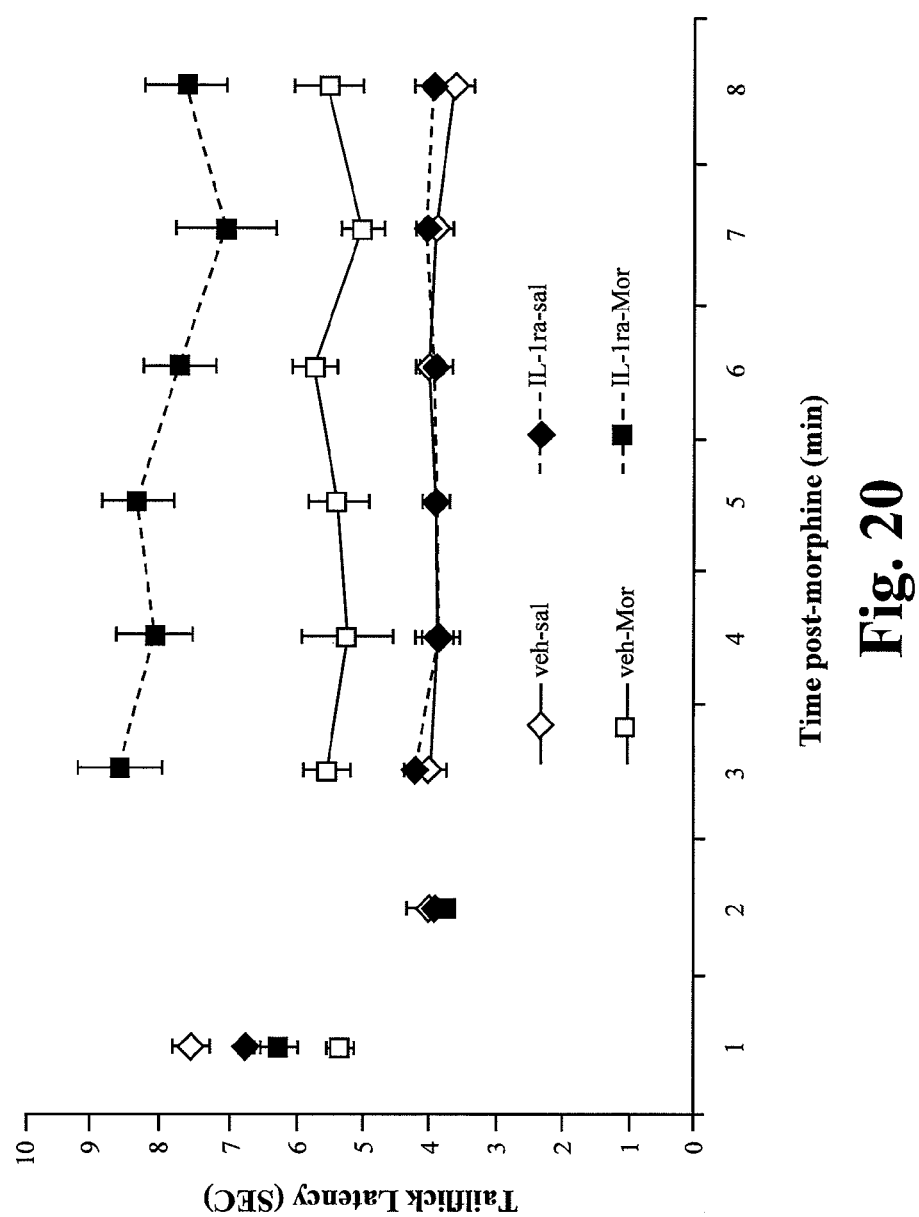
FIG. 20 shows the continued effect of IL-1ra on morphine tolerance. The continuing effect was still observed on the last day of testing, that is after 5 days of morphine.

As seen in FIGS. 19 and 20, IL-1ra injected into spinal cerebrospinal fluid caused a delay in the development of morphine tolerance as IL-1ra-injected rats showed greater morphine analgesia than did control rats.

Figure 21A:
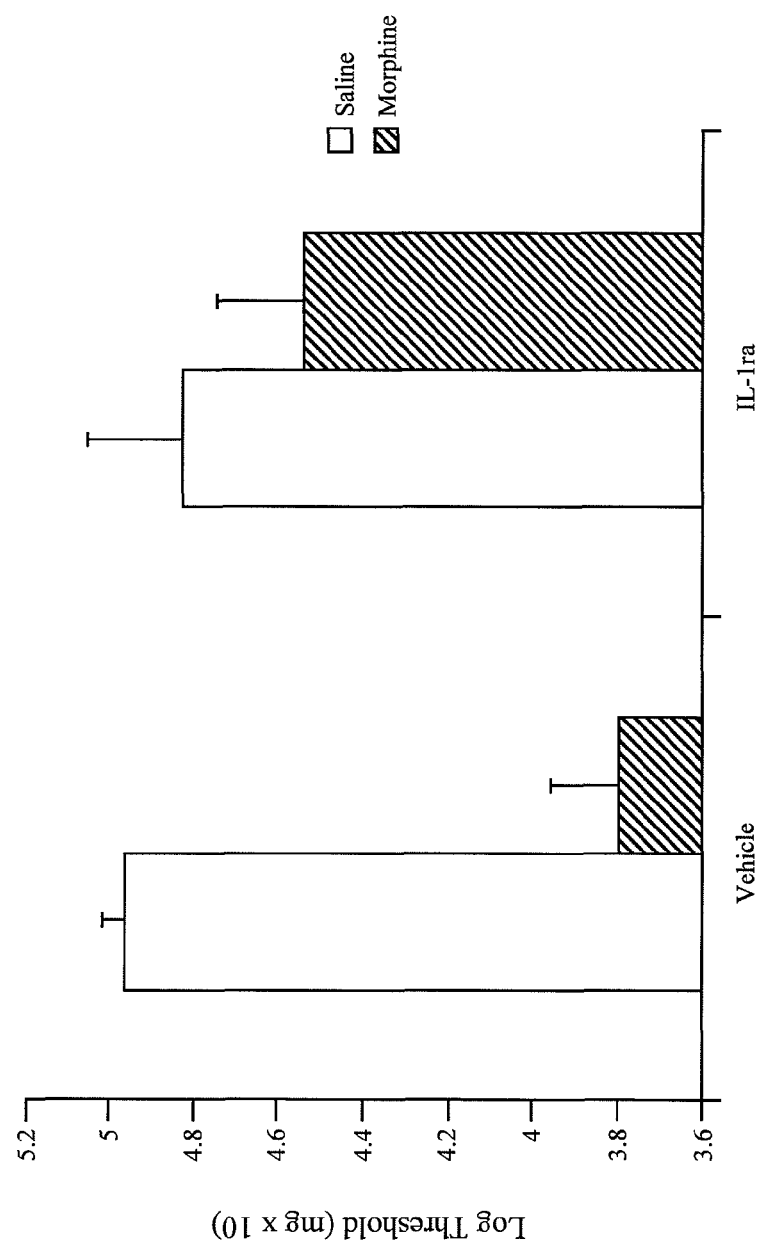

As seen in FIG. 21A, repeated morphine administration caused a decrease in pain threshold (increased in pain responsivity) in animals administered intrathecal morphine+ vehicle (left black bar). This is a classic effect of chronic morphine, wherein abstinence from the opiate causes exaggerated pain responses. Here, is it recorded immediately prior to the daily dose of morphine, thus 24 hr after the last dose of morphine. Daily intrathecal IL-1ra prevented this increase in pain sensitivity (right black bar).

B. To test whether the effects observed in Examples 10 and 11A implied that chronic morphine increased the production and release of proinflammatory cytokines, levels of IL-1 protein were assayed by ELISA from tissues collected after chronic intrathecal morphine versus vehicle administration. Hence rats either received 5 days of 10 µg morphine or equivolume of vehicle. Two hours after the last intrathecal injection (at a time when chronic morphine-induced mechanical allodynia and thermal hyperalgesia occur), rats were overdosed with sodium pentobarbital and lumbosacral CSF and dorsal spinal cord were collected. Samples were immediately flash-frozen in liquid nitrogen and stored at −80 C until assayed by ELISA.

As seen in FIGS. 21B and 21C, chronic morphine treatment increased expression of IL-1 protein in both spinal cord CSF (FIG. 21B) and in dorsal spinal cord tissue (FIG. 21C). The increase in CSF levels is important as it shows that IL-1 was not simply produced but rather was also released, thus enabling it to exert effects on neurons and other glia.

Example 12

Effects of IL-1ra on CCI Induced Mechanical Allodynia

The data presented to this point suggested that IL-10 might be blocking/reversing pathological pain states because it was suppressing proinflammatory cytokines. To test whether CCI was in fact mediated by proinflammatory cytokines, the following experiment was performed. Rats were first assessed for baseline (BL) responsivity on the von Frey test and then subjected to either CCI or sham surgery. Behaviors were reassessed 3 and 10 days later to verify surgical efficacy. One group of rats was then immediately administered either 100 µg IL-1ra or equivolume (1 µl) vehicle intrathecally, then monitored for behaviors on the von Frey test for several hours (FIG. 30A). The second group of rats was treated identically save that these intrathecal injections occurred 2 months after surgery (FIG. 30B). As shown in FIGS. 30A and 30B, in both cases, the proinflammatory cytokine antagonist transiently reversed mechanical allodynia in CCI treated animals, while having no effect on sham operated controls. These data support that proinflammatory cytokines are key players in both creating and maintaining pathological pain states over extended periods of time.

Example 13

Effect of Injected IL-10 on Chronic Constriction Injury (CCI) Induced Mechanical Allodynia The previous examples illustrate the therapeutic efficacy of delivering viral and non-viral vectors encoding IL-10 in order to treat pain. In order to compare the effect of injected IL-10 protein versus gene therapy using DNA encoding IL-10, the following experiment was conducted. Recombinant rat IL-10 protein (Sigma Chemical Co., St. Louis, Mo.; lot #101K0290) was reconstituted in sterile Dulbecco's PBS containing 0.1% rat serum albumen at a stock concentration of 0.1 mg/mL, aliquoted in sterile eppendorf tubes and stored at −80° C. until the time of injection. Animals received three injections of rat IL-10 protein. At the time of the first injection, stock IL-10 protein was thawed on ice and diluted with Dulbecco's PBS containing 0.1% rat serum albumen to a final concentration of 0.01 mg/mL. The dose of the first injection was 50 ng in 50 µl. The second and third injections of rat IL-10 protein were higher (500 ng in 5 µl), thus stock solution of IL-10 protein was thawed on ice immediately followed by an i.t. injection. Control animals received equivolume vehicle (sterile Dulbecco's PBS containing 5% bovine serum albumen and 0.1% rat serum albumen) injections.

Rats were assessed for their BL responses to the von Frey test and Hargreaves test prior to and again on Days 3 and 10 after CCI or sham surgery. In this experiment, three separate, temporally spaced i.t. injections were administered starting day 10 after the induction of CCI. Behaviors on the von Frey test and Hargreaves test were assessed at 1 and/or 2 hr and 24 hr after each injection. The dose of rat recombinant IL-10 protein was 50 ng in 5 µl for the first i.t. injection and 500 ng in 5 µl for the second and third injection. The higher dose for the second and third injection was to ensure that maximal effects of the IL-10 protein on both behavioral tests could be observed.

Figure 22A:
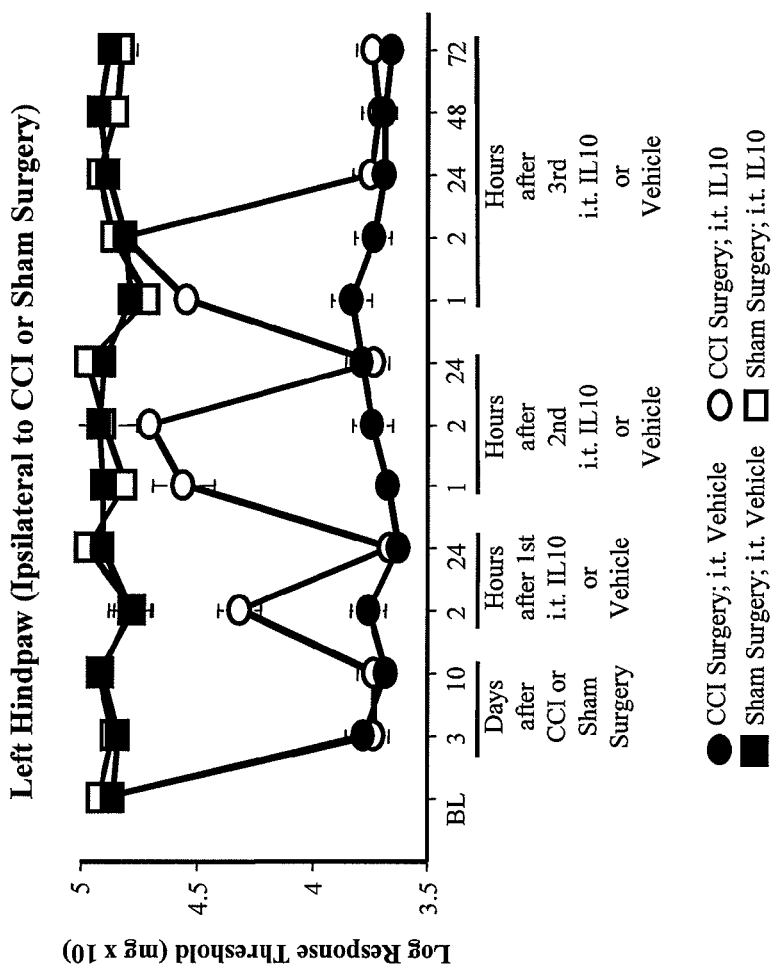
FIGS. 22A and 22B show that intrathecal injection of rat recombinant IL-10 (no plasmid; simply injection of the IL10 protein) only very briefly reverses mechanical allodynia even at very high doses.
Figure 22B:
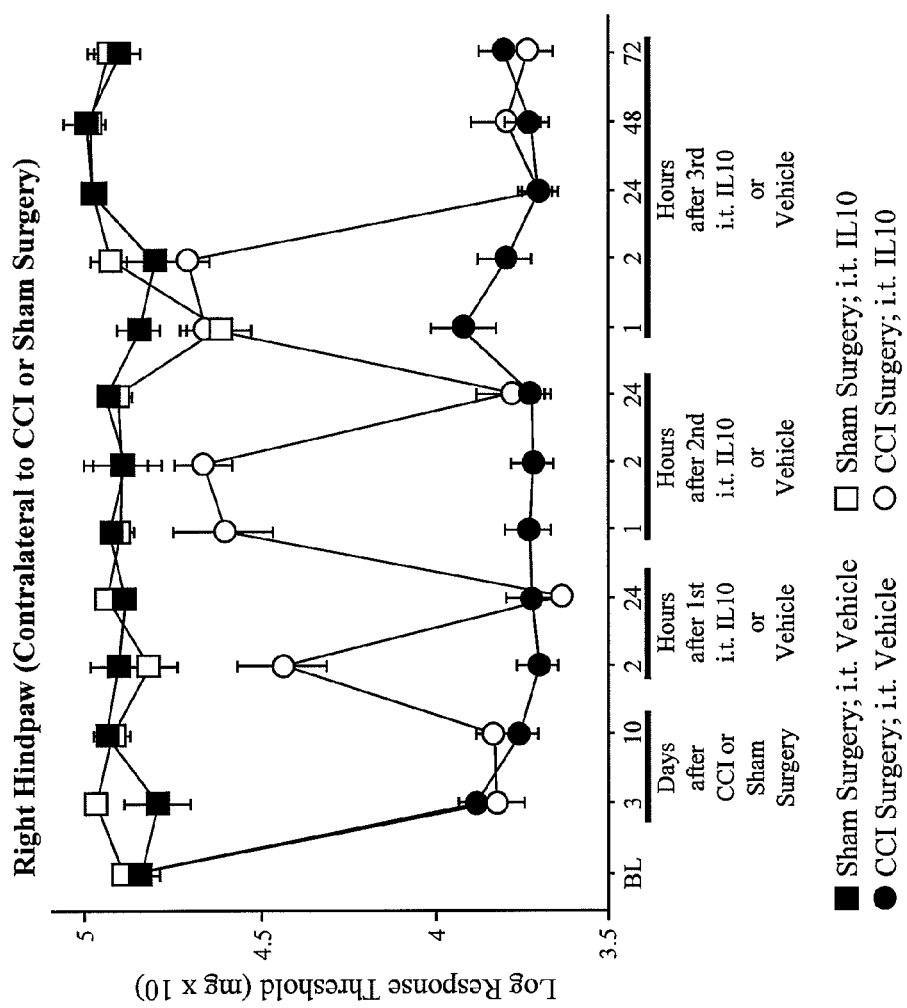
Figure 23A:
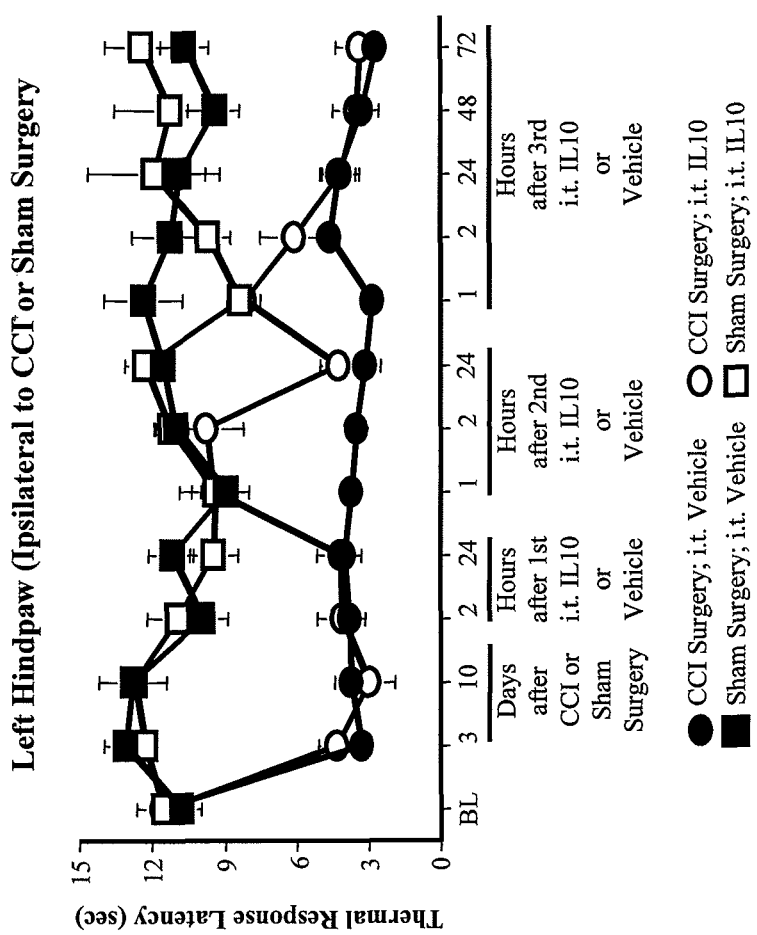
FIGS. 23A and 23B show that intrathecal injection of rat recombinant IL-10 (no plasmid; simply injection of the IL-10 protein) only very briefly reverses thermal hyperalgesia even at very high doses.
Figure 23B:
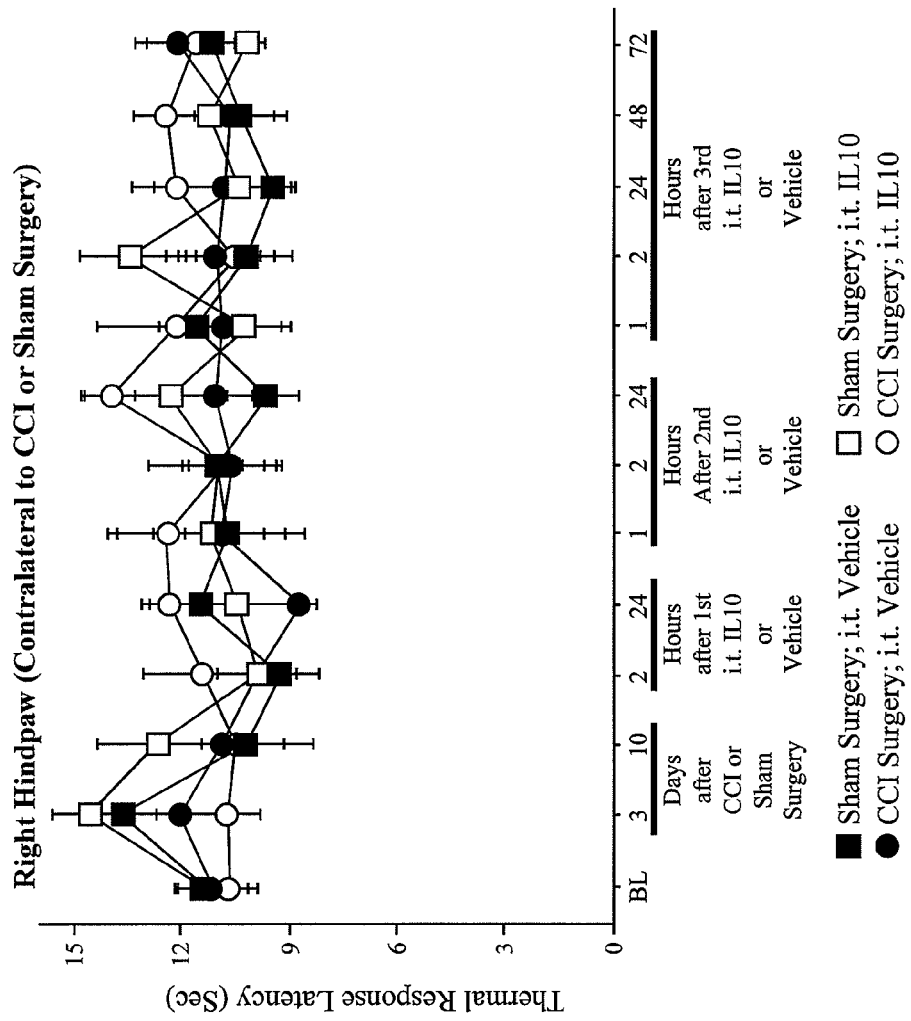

All groups showed similar BL values ($F_{7,26}=0.510$, $p>0.8$) for the von Frey test prior to CCI surgery. As observed in previous experiments and shown in FIGS. 22 and 23, CCI again produced chronic bilateral mechanical allodynia and chronic ipsilateral thermal hyperalgesia. For behavioral assessments at Days 3 and 10, prior to rat recombinant IL-10 intrathecal administration, ANOVA for the von Frey test revealed reliable main effects of CCI ($F_{1,26}=1102.390$, $p<0.0001$).

In addition, prior to CCI surgery, all groups showed no behavioral BL differences for the Hargreaves test ($F_{7,26}=0.324$, $p>0.9$). Before rat recombinant IL-10 intrathecal administration, ANOVA for the Hargreaves test revealed reliable main effects of CCI ($F_{1,26}=94.228$, $p<0.0001$) and laterality ($F_{1,26}=37.784$, $p<0.0001$), and an interaction between CCI and laterality ($F_{1,26}=42.128$, $p<0.0001$).

After the first intrathecal rat recombinant IL-10 administration, rat recombinant IL-10 reversed these ongoing pathological pain states. The lower dose of rat recombinant IL-10 (only for the first injection; 50 ng) reversed only bilateral allodynia, but not ipsilateral thermal hyperalgesia induced by CCI. ANOVA revealed for the von Frey test reliable main effects of CCI ($F_{1,26}=913.411$, $p<0.0001$), rat recombinant IL-10 ($F_{1,26}=26.744$, $p<0.0001$) and time after rat recombinant IL-10 ($F_{1,26}=11.538$, $p<0.0001$), and interactions between CCI and rat recombinant IL-10 ($F_{1,26}=17.755$, $p<0.001$), time and CCI ($F_{1,26}=48.915$, $p<0.0001$), time and rat recombinant IL-10 ($F_{1,26}=17.344$, $p<0.001$), time, CCI and rat recombinant IL-10 ($F_{1,26}=23.563$, $p<0.0001$).

ANOVA revealed for the Hargreaves test reliable main effects of CCI ($F_{1,26}=28.492$, $p<0.0001$) and laterality ($F_{1,26}=25.603$, $p<0.0001$) and an interaction between CCI and laterality ($F_{1,26}=34.857$, $p<0.0001$). There was no reliable main effect of rat recombinant IL-10 at this lower dose on the Hargreaves test.

After the second intrathecal rat recombinant IL-10 administration, which was given at the higher dose of 500 ng, rat recombinant IL-10 reversed both bilateral allodynia and ipsilateral thermal hyperalgesia induced by CCI. ANOVA revealed for the von Frey test reliable main effects of CCI ($F_{1,26}=450.175$, $p<0.0001$), rat recombinant IL-10 ($F_{1,26}=51.815$, $p<0.0001$) and time after rat recombinant IL-10 ($F_{2,52}=31.983$, $p<0.0001$), and interactions between CCI and rat recombinant IL-10 ($F_{1,26}=60.758$, $p<0.0001$), time and CCI ($F_{2,26}=38.202$, $p<0.0001$), time and rat recombinant IL-10 ($F_{2,26}=39.030$, $p<0.001$), and time, CCI and rat recombinant IL-10 ($F_{2,26}=44.300$, $p<0.0001$).

ANOVA revealed for the Hargreaves test reliable main effects of CCI ($F_{1,26}=15.957$, $p<0.001$), rat recombinant IL-10 ($F_{1,26}=11.337$, $p<0.005$), and laterality ($F_{1,26}=25.278$, $p<0.0001$) and interactions between CCI and laterality ($F_{1,26}=27.133$, $p<0.0001$) and time, rat recombinant IL-10 and laterality ($F_{2,52}=2.239$, $p<0.05$).

After the third intrathecal rat recombinant IL-10 injection, which was also given at the higher dose of 500 ng, IL-10 again reversed both bilateral allodynia and ipsilateral thermal hyperalgesia induced by CCI. ANOVA revealed for the von Frey test reliable main effects of CCI ($F_{1,26}$=1130.649, p<0.0001), rat recombinant IL-10 ($F_{1,26}$=38.190, p<0.0001) and time after rat recombinant IL-10 ($F_{4,104}$=32.709, p<0.00001), and interactions between CCI and rat recombinant IL-10 ($F_{1,26}$=45.951, p<0.0001), time and CCI ($F_{4,104}$=81.860, p<0.0001), time and rat recombinant IL-10 ($F_{4,104}$=37.044, p<0.001), and time, CCI and rat recombinant IL-10 ($F_{4,104}$=34.969, p<0.0001). Rats remained fully allodynic from 24 through 72 hrs after the third injection. ANOVA revealed a main effect of only CCI ($F_{1,26}$=1506.028, p<0.0001). All other comparisons were not reliable (p>0.10).

ANOVA revealed for the Hargreaves test reliable main effects of CCI ($F_{1,26}$=293.036, p<0.0001), and laterality ($F_{1,26}$=47.126, p<0.0001) and interactions between CCI and laterality ($F_{1,26}$=56.134, p<0.0001) and time, rat recombinant IL-10 and ($F_{4,104}$=3.396, p<0.05). Rats remained fully allodynic from 24 through 72 hrs after the third injection. ANOVA revealed a main effect of CCI ($F_{1,26}$=37.706, p<0.0001), laterality ($F_{1,26}$=44.118, p<0.0001) and an interaction between CCI and laterality ($F_{1,26}$=72.034, p<0.0001). All other comparisons were not reliable (P>0.15).

Example 14

Effect of Injected IL-10 on PLA2 Induced Mechanical Allodynia

Figure 26:
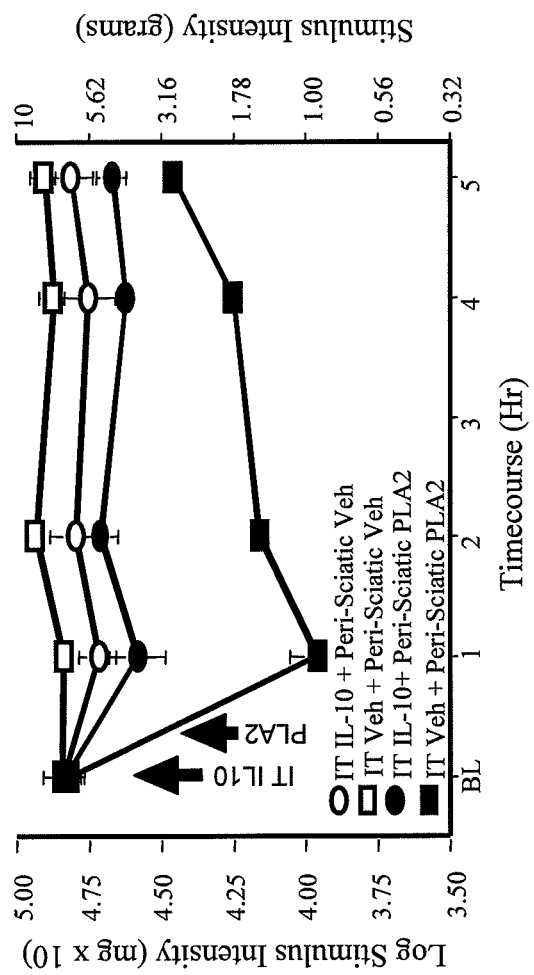
FIG. 26 shows that intrathecal administration of recombinant IL-10 protein blocked mechanical allodynia induced by peri-sciatic injection of phospholipase A2 (PLA2). Open ovals indicate results from intrathecal administration of IL-10 and peri-sciatic delivery of vehicle only. Open rectangles indicate results from intrathecal administration of vehicle only and peri-sciatic delivery of vehicle only. Filled ovals indicate results from intrathecal administration of IL-10 and peri-sciatic delivery of PLA2. Filled rectangles indicate results from intrathecal administration of vehicle only and peri-sciatic delivery of vehicle only.

Mechanical allodynia was induced in rats by peri-sciatic injection of phospholipase A2 (PLA2), an inflammatory mediator released by activated immune cells. Allodynia induced by peri-sciatic injection of PLA2 is mediated by spinal proinflammatory cytokines (Chacur et al., *Pain* (2001) 94:231-244). 10 ng of IL-10 was administered to rats intrathecally, followed by PLA2 induced allodynia. As shown in FIG. 26, intrathecal administration of 10 ng of IL-10 blocked development of allodynia, at least for five hours.

Example 15

Effect Of Fc-IL10 on Chronic Constriction Injury (CCI) Induced Mechanical Allodynia Examples 13 and 14 showed the ability of IL-10 protein to reverse enhanced pain states. Here, the efficacy of a stabilized variant of IL-10 (FcIL-10) was examined to test whether it too exerted such effects. Rats were first tested for baseline (BL) responses on the von Frey test. All rats then underwent CCI surgery. Behaviors were reassessed at Days 3 and 10 to verify that CCI surgery did produce mechanical allodynia (FIG. 27). Rats were injected i.t. with 250 ng FcIL-10 (a non-lytic recombinant human IL-10/Fc chimera, Sigma Chemical Co., St. Louis, Mo., product number I9404) plus a plasmid encoding for IL-10. Since plasmid has no effect on behavior until one day later, effects observed shortly after this injection procedure reflect actions by FcIL-10 itself. As can be seen in FIG. 27, mechanical allodynia was transiently reversed by FcIL-10 treatment.

Example 16

FcIL-10 Enhances the Effectiveness of Gene Therapy

The present experiment illustrates the therapeutic efficacy of IL-10 delivered closely in time with a gene therapy vector. After baseline (BL) testing, rats received CCI surgery. They were re-tested 3 and 10 days later to verify that CCI induced profound neuropathic pain (FIG. 28). After the Day 10 test, rats were injected i.t. with a control plasmid that did not encode IL-10; rather, it encoded for an inert intracellular protein (GFP). It can be seen that the presence of inert plasmid DNA did not affect behaviors tested the subsequent days. After the Day 13 test, rats were injected with either: (a) only plasmid encoding for IL-10 or (b) an equal amount of plasmid encoding for IL-10 plus a stabilized variant of IL-10 (FcIL-10) to test whether the presence of FcIL-10 would enhance vector efficacy. Indeed it did. Mechanical allodynia was reversed by plasmid-IL10 alone for approximately 4 days (see, the effect of the first injection of plasmid-IL10 shown in FIG. 13). In contrast, the co-treatment with FcIL-10 remarkably enhanced both the onset and duration of plasmid-IL10 efficacy on mechanical allodynia.

Example 17

Effectiveness of Lower Doses and Dose Combinations of Plasmid IL10 Gene Therapy

After baseline (BL) testing, rats received CCI surgery. They were re-tested 3 and 10 days later to verify that CCI induced profound neuropathic pain on the von Frey test (mechanical allodynia). Rats were then injected with either: (a) 100 µg plasmid encoding IL-10 (Day 10) followed by 50 µg plasmid encoding IL-10 (Day 13) (FIG. 29A); (b) 100 µg plasmid encoding IL-10 (Day 10) followed by 25 µg plasmid encoding IL-10 (Day 13) (FIG. 29B); or (c) 50 µg plasmid encoding IL-10 (Day 10) followed by 50 µg plasmid encoding IL-10 (Day 13) (FIG. 29C). As shown in the figures, each led to reversal of mechanical allodynia over time.

Thus, methods for delivering anti-inflammatory cytokines to the CNS for the treatment of pathological pain are described. Although preferred embodiments of the subject invention have been described in some detail, it is understood that obvious variations can be made without departing from the spirit and the scope of the invention as defined herein.

The invention claimed is:

1. A method of treating existing neuropathic pain in a mammalian subject comprising intrathecally administering to the central nervous system of said subject with existing neuropathic pain a recombinant virus or plasmid comprising a polynucleotide encoding interleukin-10 (IL-10) operably linked to expression control elements, wherein expression of said polynucleotide in the central nervous system reduces neuropathic pain for at least 24 hours.

2. The method of claim 1, wherein said subject is a human and said IL-10 is human IL-10.

3. The method of claim 1, wherein said subject is administered a recombinant virus.

4. The method of claim 3, wherein said recombinant virus is a recombinant adenovirus.

5. The method of claim 3, wherein said recombinant virus is a recombinant adeno-associated virion.

* * * * *

SEQUENCE LISTING

<160> NUMBER OF SEQ ID NOS: 5

<210> SEQ ID NO 1
<211> LENGTH: 160
<212> TYPE: PRT
<213> ORGANISM: Homo sapiens

<400> SEQUENCE: 1

| Ser | Pro | Gly | Gln | Gly | Thr | Gln | Ser | Glu | Asn | Ser | Cys | Thr | His | Phe | Pro |
| 1 | | | | 5 | | | | | 10 | | | | | 15 | |
| Gly | Asn | Leu | Pro | Asn | Met | Leu | Arg | Asp | Leu | Arg | Asp | Ala | Phe | Ser | Arg |
| | | | 20 | | | | | 25 | | | | | 30 | | |
| Val | Lys | Thr | Phe | Phe | Gln | Met | Lys | Asp | Gln | Leu | Asp | Asn | Leu | Leu | Leu |
| | | 35 | | | | | 40 | | | | | 45 | | | |
| Lys | Glu | Ser | Leu | Leu | Glu | Asp | Phe | Lys | Gly | Tyr | Leu | Gly | Cys | Gln | Ala |
| | 50 | | | | | 55 | | | | | 60 | | | | |
| Leu | Ser | Glu | Met | Ile | Gln | Phe | Tyr | Leu | Glu | Glu | Val | Met | Pro | Gln | Ala |
| 65 | | | | | 70 | | | | | 75 | | | | | 80 |
| Glu | Asn | Gln | Asp | Pro | Asp | Ile | Lys | Ala | His | Val | Asn | Ser | Leu | Gly | Glu |
| | | | | 85 | | | | | 90 | | | | | 95 | |
| Asn | Leu | Lys | Thr | Leu | Arg | Leu | Arg | Leu | Arg | Arg | Cys | His | Arg | Phe | Leu |
| | | | 100 | | | | | 105 | | | | | 110 | | |
| Pro | Cys | Glu | Asn | Lys | Ser | Lys | Ala | Val | Glu | Gln | Val | Lys | Asn | Ala | Phe |
| | | | 115 | | | | | 120 | | | | | 125 | | |
| Asn | Lys | Leu | Gln | Glu | Lys | Gly | Ile | Tyr | Lys | Ala | Met | Ser | Glu | Phe | Asp |
| | | | 130 | | | | | 135 | | | | | 140 | | |
| Ile | Phe | Ile | Asn | Tyr | Ile | Glu | Ala | Tyr | Met | Thr | Met | Lys | Ile | Arg | Asn |
| 145 | | | | | 150 | | | | | 155 | | | | | 160 |

<210> SEQ ID NO 2
<211> LENGTH: 160
<212> TYPE: PRT
<213> ORGANISM: Artificial
<220> FEATURE:
<223> OTHER INFORMATION: mouse IL-10 (mIL-10)

<400> SEQUENCE: 2

| Ser | Arg | Gly | Gln | Tyr | Ser | Arg | Glu | Asp | Asn | Asn | Cys | Thr | His | Phe | Pro |
| 1 | | | | 5 | | | | | 10 | | | | | 15 | |
| Val | Gly | Gln | Ser | His | Met | Leu | Leu | Glu | Leu | Arg | Thr | Ala | Phe | Ser | Gln |
| | | | 20 | | | | | 25 | | | | | 30 | | |
| Val | Lys | Thr | Phe | Phe | Gln | Thr | Lys | Asp | Gln | Leu | Asp | Asn | Ile | Leu | Leu |
| | | 35 | | | | | 40 | | | | | 45 | | | |
| Thr | Asp | Ser | Leu | Met | Gln | Asp | Phe | Lys | Gly | Tyr | Leu | Gly | Cys | Gln | Ala |
| | 50 | | | | | 55 | | | | | 60 | | | | |
| Leu | Ser | Glu | Met | Ile | Gln | Phe | Tyr | Leu | Val | Glu | Val | Met | Pro | Gln | Ala |
| 65 | | | | | 70 | | | | | 75 | | | | | 80 |
| Glu | Lys | His | Gly | Pro | Glu | Ile | Lys | Glu | His | Leu | Asn | Ser | Leu | Gly | Glu |
| | | | | 85 | | | | | 90 | | | | | 95 | |
| Lys | Leu | Lys | Thr | Leu | Arg | Met | Arg | Leu | Arg | Arg | Cys | His | Arg | Phe | Leu |
| | | | 100 | | | | | 105 | | | | | 110 | | |
| Pro | Cys | Glu | Asn | Lys | Ser | Lys | Ala | Val | Glu | Gln | Val | Lys | Ser | Asp | Phe |
| | | | 115 | | | | | 120 | | | | | 125 | | |
| Asn | Lys | Leu | Gln | Asp | Gln | Gly | Val | Tyr | Lys | Ala | Met | Asn | Glu | Phe | Asp |
| | | | 130 | | | | | 135 | | | | | 140 | | |
| Ile | Phe | Ile | Asn | Cys | Ile | Glu | Ala | Tyr | Met | Met | Ile | Lys | Met | Lys | Ser |
| 145 | | | | | 150 | | | | | 155 | | | | | 160 |

<210> SEQ ID NO 3
<211> LENGTH: 145
<212> TYPE: PRT
<213> ORGANISM: Artificial
<220> FEATURE:
<223> OTHER INFORMATION: viral form of IL-10 (vIL-10)

```
<400> SEQUENCE: 3

Gln Cys Asp Asn Phe Pro Gln Met Leu Arg Asp Leu Arg Asp Ala Phe
1               5                   10                  15

Ser Arg Val Lys Thr Phe Phe Gln Thr Lys Asp Glu Val Asp Asn Leu
            20                  25                  30

Leu Leu Lys Glu Ser Leu Leu Glu Asp Phe Lys Gly Tyr Leu Gly Cys
        35                  40                  45

Gln Ala Leu Ser Glu Met Ile Gln Phe Tyr Leu Glu Glu Val Met Pro
    50                  55                  60

Gln Ala Glu Asn Gln Asp Pro Glu Ala Lys Asp His Val Asn Ser Leu
65                  70                  75                  80

Gly Glu Asn Leu Lys Thr Leu Arg Leu Arg Leu Arg Arg Cys His Arg
                85                  90                  95

Phe Leu Pro Cys Glu Asn Lys Ser Lys Ala Val Glu Gln Ile Lys Asn
            100                 105                 110

Ala Phe Asn Lys Leu Gln Glu Lys Gly Ile Tyr Lys Ala Met Ser Glu
        115                 120                 125

Phe Asp Ile Phe Ile Asn Tyr Ile Glu Ala Tyr Met Thr Ile Lys Ala
    130                 135                 140

Arg
145

<210> SEQ ID NO 4
<211> LENGTH: 9
<212> TYPE: PRT
<213> ORGANISM: Artificial
<220> FEATURE:
<223> OTHER INFORMATION: IL-10 fragment

<400> SEQUENCE: 4

Ala Tyr Met Thr Met Lys Ile Arg Asn
1               5

<210> SEQ ID NO 5
<211> LENGTH: 9
<212> TYPE: PRT
<213> ORGANISM: Artificial
<220> FEATURE:
<223> OTHER INFORMATION: IL-10 variants
<220> FEATURE:
<221> NAME/KEY: MISC_FEATURE
<222> LOCATION: (1)..(1)
<223> OTHER INFORMATION: Xaa = Ala or Gly
<220> FEATURE:
<221> NAME/KEY: MISC_FEATURE
<222> LOCATION: (2)..(2)
<223> OTHER INFORMATION: Xaa = Tyr or Phe
<220> FEATURE:
<221> NAME/KEY: MISC_FEATURE
<222> LOCATION: (3)..(3)
<223> OTHER INFORMATION: Xaa = Met, Ile, Leu or Val
<220> FEATURE:
<221> NAME/KEY: MISC_FEATURE
<222> LOCATION: (5)..(5)
<223> OTHER INFORMATION: Xaa = Met, Ile, Leu or Val
<220> FEATURE:
<221> NAME/KEY: MISC_FEATURE
<222> LOCATION: (7)..(7)
<223> OTHER INFORMATION: Xaa = Met, Ile, Leu or Val
<220> FEATURE:
<221> NAME/KEY: MISC_FEATURE
<222> LOCATION: (9)..(9)
<223> OTHER INFORMATION: Xaa = Asp, Gln or Gly
```

```
<400> SEQUENCE: 5

Xaa Xaa Xaa Thr Xaa Lys Xaa Arg Xaa
1               5
```